(12) United States Patent
Hariton et al.

(10) Patent No.: US 11,318,014 B2
(45) Date of Patent: May 3, 2022

(54) PROSTHETIC VALVE DELIVERY SYSTEM WITH MULTI-PLANAR STEERING

(71) Applicant: CARDIOVALVE LTD., Or Yehuda (IL)

(72) Inventors: Ilia Hariton, Zichron Yaackov (IL); Meni Iamberger, Kfar Saba (IL); Aviram Baum, Tel Aviv (IL); Boaz Harari, Ganey Tikva (IL)

(73) Assignee: CARDIOVALVE LTD., Or Yehuda (IL)

( * ) Notice: Subject to any disclaimer, the term of this patent is extended or adjusted under 35 U.S.C. 154(b) by 16 days.

(21) Appl. No.: 16/135,619

(22) Filed: Sep. 19, 2018

(65) Prior Publication Data

US 2019/0083263 A1 Mar. 21, 2019

Related U.S. Application Data

(60) Provisional application No. 62/560,384, filed on Sep. 19, 2017.

(51) Int. Cl.
*A61F 2/24* (2006.01)

(52) U.S. Cl.
CPC ............ *A61F 2/2427* (2013.01); *A61F 2/243* (2013.01); *A61F 2/2436* (2013.01); *A61F 2/2445* (2013.01); *A61F 2/2454* (2013.01); *A61F 2/2463* (2013.01); *A61F 2/246* (2013.01); *A61F 2/2409* (2013.01); *A61F 2/2418* (2013.01);
(Continued)

(58) Field of Classification Search
CPC ....... A61F 2/2427; A61F 2/243; A61F 2/2436
See application file for complete search history.

(56) References Cited

U.S. PATENT DOCUMENTS

| 3,874,388 A | 4/1975 | King et al. |
| 4,222,126 A | 9/1980 | Boretos et al. |

(Continued)

FOREIGN PATENT DOCUMENTS

| CA | 2822801 A1 | 8/2006 |
| CN | 103974674 A | 8/2014 |

(Continued)

OTHER PUBLICATIONS

International Search Report dated Dec. 5, 2011, by the United States Patent and Trademark Office in PCT/IL2011/000582 (3 pages).

(Continued)

*Primary Examiner* — Melanie R Tyson
(74) *Attorney, Agent, or Firm* — Finnegan, Henderson, Farabow, Garrett & Dunner, LLP

(57) ABSTRACT

A prosthetic valve delivery system may be provided. The prosthetic valve delivery system may include a first catheter and a first steering mechanism configured to bend the first catheter within a first steering plane. The prosthetic valve delivery system may also include a second catheter coaxially arranged within the first catheter and a second steering mechanism configured to bend the second catheter within a second steering plane, different from the first steering plane. Moreover, the prosthetic valve delivery system may include a capsule positioned distal to both the first catheter and the second catheter. The capsule may be configured to retain a prosthetic valve therein during transvascular advancement of the capsule.

21 Claims, 21 Drawing Sheets

(52) U.S. Cl.
CPC ..... *A61F 2/2466* (2013.01); *A61F 2210/0014* (2013.01); *A61F 2220/0008* (2013.01); *A61F 2250/007* (2013.01)

(56) References Cited

U.S. PATENT DOCUMENTS

| | | |
|---|---|---|
| 4,340,091 A | 7/1982 | Skelton et al. |
| 4,972,494 A | 11/1990 | White et al. |
| 5,201,757 A | 4/1993 | Heyn et al. |
| 5,713,948 A | 2/1998 | Uflacker |
| 5,716,417 A | 2/1998 | Girard et al. |
| 5,741,297 A | 4/1998 | Simon |
| 5,776,140 A | 7/1998 | Cottone |
| 5,957,949 A | 9/1999 | Leonhardt et al. |
| 5,961,549 A | 10/1999 | Nguyen et al. |
| 6,010,530 A | 1/2000 | Goicoechea |
| 6,126,686 A | 10/2000 | Badylak et al. |
| 6,165,183 A | 12/2000 | Kuehn et al. |
| 6,254,609 B1 | 7/2001 | Vrba et al. |
| 6,312,465 B1 | 11/2001 | Griffin et al. |
| 6,346,074 B1 | 2/2002 | Roth |
| 6,402,780 B2 | 6/2002 | Williamson, IV et al. |
| 6,458,153 B1 | 10/2002 | Bailey et al. |
| 6,669,724 B2 | 12/2003 | Park et al. |
| 6,733,525 B2 | 5/2004 | Yang et al. |
| 6,752,813 B2 | 6/2004 | Goldfarb et al. |
| 6,755,857 B2 | 6/2004 | Peterson et al. |
| 6,926,715 B1 | 8/2005 | Hauck et al. |
| 6,939,370 B2 | 9/2005 | Hartley et al. |
| 7,074,236 B2 | 7/2006 | Rabkin et al. |
| 7,201,772 B2 | 4/2007 | Schwammenthal et al. |
| 7,226,467 B2 | 6/2007 | Lucatero et al. |
| 7,261,686 B2 | 8/2007 | Couvillon, Jr. |
| 7,288,097 B2 | 10/2007 | Séguin |
| 7,442,204 B2 | 10/2008 | Schwammenthal et al. |
| 7,556,632 B2 | 7/2009 | Zadno |
| 7,563,267 B2 | 7/2009 | Goldfarb et al. |
| 7,563,273 B2 | 7/2009 | Goldfarb et al. |
| 7,608,091 B2 | 10/2009 | Goldfarb et al. |
| 7,635,329 B2 | 12/2009 | Goldfarb et al. |
| 7,655,015 B2 | 2/2010 | Goldfarb et al. |
| 7,736,388 B2 | 6/2010 | Goldfarb et al. |
| 7,753,949 B2 | 7/2010 | Lamphere et al. |
| 7,811,296 B2 | 10/2010 | Goldfarb et al. |
| 7,837,727 B2 | 11/2010 | Goetz et al. |
| 7,959,672 B2 | 6/2011 | Salahieh et al. |
| 8,052,592 B2 | 11/2011 | Goldfarb et al. |
| 8,057,493 B2 | 11/2011 | Goldfarb et al. |
| 8,070,802 B2 | 12/2011 | Lamphere et al. |
| D652,927 S | 1/2012 | Braido et al. |
| D653,341 S | 1/2012 | Braido et al. |
| 8,109,996 B2 | 2/2012 | Stacchino et al. |
| D660,433 S | 5/2012 | Braido et al. |
| D660,967 S | 5/2012 | Braido et al. |
| 8,216,256 B2 | 7/2012 | Raschdorf, Jr. et al. |
| 8,313,525 B2 | 11/2012 | Tuval et al. |
| 8,403,983 B2 | 3/2013 | Quadri et al. |
| 8,414,644 B2 | 4/2013 | Quadri et al. |
| 8,449,599 B2 | 5/2013 | Chau et al. |
| 8,568,475 B2 | 10/2013 | Nguyen et al. |
| 8,582,672 B2 | 10/2013 | Bonhoeffer et al. |
| 8,579,964 B2 | 11/2013 | Lane et al. |
| 8,585,755 B2 | 11/2013 | Chau et al. |
| 8,628,571 B1 | 1/2014 | Hacohen et al. |
| 8,652,203 B2 | 2/2014 | Quadri et al. |
| 8,657,872 B2 | 2/2014 | Seguin |
| 8,728,155 B2 | 5/2014 | Montorfano et al. |
| 8,747,460 B2 | 6/2014 | Tuval et al. |
| 8,784,481 B2 | 7/2014 | Alkhatib et al. |
| 8,852,272 B2 | 10/2014 | Gross et al. |
| 8,870,948 B1 | 10/2014 | Erzberger et al. |
| 8,870,950 B2 | 10/2014 | Hacohen |
| 8,961,595 B2 | 2/2015 | Alkhatib |
| 8,986,375 B2 | 3/2015 | Garde et al. |
| 8,992,604 B2 | 3/2015 | Gross et al. |
| 8,998,982 B2 | 4/2015 | Richter et al. |
| 9,017,399 B2 | 4/2015 | Gross et al. |
| D730,520 S | 5/2015 | Braido et al. |
| D730,521 S | 5/2015 | Braido et al. |
| 9,023,100 B2 | 5/2015 | Quadri et al. |
| D732,666 S | 6/2015 | Nguyen et al. |
| 9,050,188 B2 | 6/2015 | Schweich, Jr. et al. |
| 9,060,858 B2 | 6/2015 | Thornton et al. |
| 9,072,603 B2 | 7/2015 | Tuval et al. |
| 9,095,434 B2 | 8/2015 | Rowe |
| 9,119,719 B2 | 9/2015 | Zipory et al. |
| 9,125,740 B2 | 9/2015 | Morriss et al. |
| 9,132,009 B2 | 9/2015 | Hacohen et al. |
| 9,173,659 B2 | 11/2015 | Bodewadt et al. |
| 9,180,009 B2 | 11/2015 | Majkrzak et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,792 B2 | 1/2016 | Benichou et al. |
| 9,248,014 B2 | 2/2016 | Lane et al. |
| 9,277,994 B2 | 3/2016 | Miller et al. |
| 9,295,551 B2 | 3/2016 | Straubinger et al. |
| 9,295,552 B2 | 3/2016 | McLean et al. |
| 9,320,591 B2 | 4/2016 | Bolduc |
| D755,384 S | 5/2016 | Pesce et al. |
| 9,345,573 B2 | 5/2016 | Nyuli et al. |
| 9,358,107 B2 | 6/2016 | Nguyen et al. |
| 9,387,078 B2 | 7/2016 | Gross et al. |
| 9,393,110 B2 | 7/2016 | Levi et al. |
| 9,439,757 B2 | 9/2016 | Wallace et al. |
| 9,445,893 B2 | 9/2016 | Vaturi |
| 9,463,102 B2 | 10/2016 | Kelly |
| 9,492,273 B2 | 11/2016 | Wallace et al. |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweich, Jr. et al. |
| 9,572,665 B2 | 2/2017 | Lane et al. |
| 9,597,182 B2 | 3/2017 | Straubinger et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,763,657 B2 | 9/2017 | Hacohen et al. |
| 9,770,256 B2 | 9/2017 | Cohen et al. |
| D800,908 S | 10/2017 | Hariton et al. |
| 9,788,941 B2 | 10/2017 | Hacohen |
| 9,895,226 B1 | 2/2018 | Harari et al. |
| 9,974,651 B2 | 5/2018 | Hariton et al. |
| 10,010,414 B2 | 7/2018 | Cooper et al. |
| 10,076,415 B1 | 9/2018 | Metchik et al. |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,143,552 B2 | 12/2018 | Wallace et al. |
| 10,149,761 B2 | 12/2018 | Granada et al. |
| 10,154,906 B2 | 12/2018 | Granada et al. |
| 10,159,570 B1 | 12/2018 | Metchik et al. |
| 10,182,908 B2 | 1/2019 | Tubishevitz et al. |
| 10,226,341 B2 | 3/2019 | Gross et al. |
| 10,231,837 B1 | 3/2019 | Metchik et al. |
| 10,238,493 B1 | 3/2019 | Metchik et al. |
| 10,245,143 B2 | 4/2019 | Gross et al. |
| 10,245,144 B1 | 4/2019 | Metchik et al. |
| 10,299,927 B2 | 5/2019 | McLean et al. |
| 10,321,995 B1 | 6/2019 | Christianson et al. |
| 10,322,020 B2 | 6/2019 | Lam et al. |
| 10,327,895 B2 | 6/2019 | Lozonschi et al. |
| 10,335,278 B2 | 7/2019 | McLean et al. |
| 10,357,360 B2 | 7/2019 | Hariton et al. |
| 10,376,361 B2 | 8/2019 | Gross et al. |
| 10,390,952 B2 | 8/2019 | Hariton et al. |
| 10,426,610 B2 | 10/2019 | Hariton et al. |
| 10,463,487 B2 | 11/2019 | Hariton et al. |
| 10,463,488 B2 | 11/2019 | Hariton et al. |
| 10,507,105 B2 | 12/2019 | Hariton et al. |

(56) References Cited

U.S. PATENT DOCUMENTS

| | | |
|---|---|---|
| 10,507,108 B2 | 12/2019 | Delgado et al. |
| 10,507,109 B2 | 12/2019 | Metchik et al. |
| 10,512,456 B2 | 12/2019 | Hacohen et al. |
| 10,517,719 B2 | 12/2019 | Miller et al. |
| 10,524,792 B2 | 1/2020 | Hernandez et al. |
| 10,524,903 B2 | 1/2020 | Hariton et al. |
| 10,531,872 B2 | 1/2020 | Hacohen et al. |
| 10,548,731 B2 | 2/2020 | Lashinski et al. |
| 10,575,948 B2 | 3/2020 | Iamberger et al. |
| 10,595,992 B2 | 3/2020 | Chambers |
| 10,595,997 B2 | 3/2020 | Metchik et al. |
| 10,610,358 B2 | 4/2020 | Vidlund et al. |
| 10,646,342 B1 | 5/2020 | Marr et al. |
| 10,667,908 B2 | 6/2020 | Hariton et al. |
| 10,682,227 B2 | 6/2020 | Hariton et al. |
| 10,695,177 B2 | 6/2020 | Hariton et al. |
| 10,702,385 B2 | 7/2020 | Hacohen |
| 10,722,360 B2 | 7/2020 | Hariton et al. |
| 10,758,342 B2 | 9/2020 | Chau et al. |
| 10,758,344 B2 | 9/2020 | Hariton et al. |
| 10,799,345 B2 | 10/2020 | Hariton et al. |
| 10,813,760 B2 | 10/2020 | Metchik et al. |
| 10,820,998 B2 | 11/2020 | Marr et al. |
| 10,842,627 B2 | 11/2020 | Delgado et al. |
| 10,849,748 B2 | 12/2020 | Hariton et al. |
| 10,856,972 B2 | 12/2020 | Hariton et al. |
| 10,856,975 B2 | 12/2020 | Hariton et al. |
| 10,856,978 B2 | 12/2020 | Straubinger et al. |
| 10,864,078 B2 | 12/2020 | Hariton et al. |
| 10,874,514 B2 | 12/2020 | Dixon et al. |
| 10,881,511 B2 | 1/2021 | Hariton et al. |
| 10,888,422 B2 | 1/2021 | Hariton et al. |
| 10,888,644 B2 | 1/2021 | Ratz et al. |
| 10,905,548 B2 | 2/2021 | Hariton et al. |
| 10,905,549 B2 | 2/2021 | Hariton et al. |
| 10,905,552 B2 | 2/2021 | Dixon et al. |
| 10,905,554 B2 | 2/2021 | Cao |
| 10,918,483 B2 | 2/2021 | Metchik et al. |
| 10,925,595 B2 | 2/2021 | Hacohen et al. |
| 10,945,844 B2 | 3/2021 | McCann et al. |
| 10,973,636 B2 | 4/2021 | Hariton et al. |
| 10,993,809 B2 | 5/2021 | McCann et al. |
| 11,083,582 B2 | 8/2021 | McCann et al. |
| 11,147,672 B2 | 10/2021 | McCann et al. |
| 2001/0005787 A1 | 6/2001 | Oz et al. |
| 2001/0021872 A1 | 9/2001 | Bailey et al. |
| 2002/0013571 A1 | 1/2002 | Goldfarb et al. |
| 2002/0032481 A1 | 3/2002 | Gabbay |
| 2003/0050694 A1 | 3/2003 | Yang et al. |
| 2003/0074059 A1 | 4/2003 | Nguyen et al. |
| 2004/0030382 A1 | 2/2004 | St. Goar et al. |
| 2004/0186558 A1 | 9/2004 | Pavcnik et al. |
| 2004/0210304 A1 | 10/2004 | Seguin et al. |
| 2004/0236354 A1 | 11/2004 | Seguin |
| 2004/0249433 A1 | 12/2004 | Freitag |
| 2005/0027348 A1 | 2/2005 | Case et al. |
| 2005/0080474 A1 | 4/2005 | Andreas et al. |
| 2005/0085900 A1 | 4/2005 | Case et al. |
| 2005/0137681 A1 | 6/2005 | Shoemaker et al. |
| 2005/0137691 A1 | 6/2005 | Salahieh et al. |
| 2005/0137692 A1 | 6/2005 | Haug et al. |
| 2005/0137697 A1 | 6/2005 | Salahieh et al. |
| 2005/0203618 A1 | 9/2005 | Sharkawy et al. |
| 2005/0240200 A1 | 10/2005 | Bergheim |
| 2005/0256566 A1 | 11/2005 | Gabbay |
| 2006/0004469 A1 | 1/2006 | Sokel |
| 2006/0020275 A1 | 1/2006 | Goldfarb et al. |
| 2006/0020327 A1 | 1/2006 | Lashinski et al. |
| 2006/0030863 A1 | 2/2006 | Fields et al. |
| 2006/0052867 A1 | 3/2006 | Revuelta et al. |
| 2006/0184203 A1 | 8/2006 | Martin et al. |
| 2006/0195183 A1 | 8/2006 | Navia et al. |
| 2006/0216404 A1 | 9/2006 | Seyler et al. |
| 2006/0229708 A1 | 10/2006 | Powell et al. |
| 2006/0259137 A1 | 11/2006 | Artof et al. |
| 2006/0282150 A1 | 12/2006 | Olson et al. |
| 2007/0016286 A1 | 1/2007 | Herrmann et al. |
| 2007/0038293 A1 | 2/2007 | St.Goar et al. |
| 2007/0056346 A1 | 3/2007 | Spenser et al. |
| 2007/0078510 A1 | 4/2007 | Ryan |
| 2007/0197858 A1 | 8/2007 | Goldfarb et al. |
| 2007/0198077 A1 | 8/2007 | Cully et al. |
| 2007/0213810 A1 | 9/2007 | Newhauser et al. |
| 2007/0219630 A1 | 9/2007 | Chu |
| 2007/0239273 A1 | 10/2007 | Allen |
| 2007/0244546 A1 | 10/2007 | Francis |
| 2008/0065011 A1* | 3/2008 | Marchand ......... A61M 25/0662 604/103.02 |
| 2008/0071361 A1 | 3/2008 | Tuval et al. |
| 2008/0071369 A1 | 3/2008 | Tuval et al. |
| 2008/0082166 A1 | 4/2008 | Styrc et al. |
| 2008/0132989 A1 | 6/2008 | Snow et al. |
| 2008/0147182 A1 | 6/2008 | Righini et al. |
| 2008/0200980 A1 | 8/2008 | Robin et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2009/0005863 A1 | 1/2009 | Goetz et al. |
| 2009/0125098 A1 | 5/2009 | Chuter |
| 2009/0157175 A1 | 6/2009 | Benichou |
| 2009/0259306 A1 | 10/2009 | Rowe |
| 2009/0281619 A1 | 11/2009 | Le et al. |
| 2010/0022823 A1 | 1/2010 | Goldfarb et al. |
| 2010/0023120 A1 | 1/2010 | Holecek et al. |
| 2010/0049313 A1 | 2/2010 | Alon et al. |
| 2010/0100167 A1 | 4/2010 | Bortlein et al. |
| 2010/0161036 A1 | 6/2010 | Pintor et al. |
| 2010/0256737 A1 | 10/2010 | Pollock et al. |
| 2010/0312333 A1 | 12/2010 | Navia et al. |
| 2010/0331971 A1 | 12/2010 | Keränen et al. |
| 2011/0004227 A1 | 1/2011 | Goldfarb et al. |
| 2011/0004299 A1 | 1/2011 | Navia et al. |
| 2011/0029072 A1 | 2/2011 | Gabbay |
| 2011/0066233 A1 | 3/2011 | Thornton et al. |
| 2011/0137397 A1 | 6/2011 | Chau et al. |
| 2011/0144742 A1 | 6/2011 | Madrid et al. |
| 2011/0208283 A1 | 8/2011 | Rust |
| 2011/0224785 A1 | 9/2011 | Hacohen |
| 2011/0245911 A1 | 10/2011 | Quill et al. |
| 2011/0264196 A1 | 10/2011 | Savage et al. |
| 2011/0282439 A1 | 11/2011 | Thill et al. |
| 2011/0306916 A1 | 12/2011 | Nitzan et al. |
| 2011/0307049 A1 | 12/2011 | Kao |
| 2011/0313515 A1 | 12/2011 | Quadri et al. |
| 2011/0319989 A1 | 12/2011 | Lane et al. |
| 2012/0016468 A1 | 1/2012 | Robin et al. |
| 2012/0022629 A1 | 1/2012 | Perera et al. |
| 2012/0022639 A1 | 1/2012 | Hacohen et al. |
| 2012/0059458 A1 | 3/2012 | Buchbinder |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0089223 A1 | 4/2012 | Nguyen et al. |
| 2012/0101571 A1 | 4/2012 | Thambar et al. |
| 2012/0165930 A1 | 6/2012 | Gifford, III et al. |
| 2012/0296418 A1 | 11/2012 | Bonyuet et al. |
| 2012/0300063 A1 | 11/2012 | Majkrzak et al. |
| 2012/0310328 A1 | 12/2012 | Olson et al. |
| 2012/0323316 A1 | 12/2012 | Chau et al. |
| 2013/0018458 A1 | 1/2013 | Yohanan et al. |
| 2013/0046373 A1 | 2/2013 | Cartledge et al. |
| 2013/0066342 A1 | 3/2013 | Dell et al. |
| 2013/0144381 A1 | 6/2013 | Quadri et al. |
| 2013/0178930 A1 | 7/2013 | Straubinger et al. |
| 2013/0190861 A1 | 7/2013 | Chau et al. |
| 2013/0231735 A1* | 9/2013 | Deem ............... A61F 2/243 623/2.11 |
| 2013/0253643 A1 | 9/2013 | Rolando et al. |
| 2013/0261738 A1 | 10/2013 | Clague et al. |
| 2013/0274870 A1 | 10/2013 | Lombardi et al. |
| 2013/0282059 A1 | 10/2013 | Ketai et al. |
| 2013/0289711 A1 | 10/2013 | Liddy et al. |
| 2013/0289740 A1 | 10/2013 | Liddy et al. |
| 2013/0304200 A1 | 11/2013 | McLean et al. |

(56) References Cited

U.S. PATENT DOCUMENTS

| | | |
|---|---|---|
| 2014/0000112 A1 | 1/2014 | Braido et al. |
| 2014/0018915 A1 | 1/2014 | Biadillah et al. |
| 2014/0067050 A1 | 3/2014 | Costello et al. |
| 2014/0142688 A1 | 5/2014 | Duffy et al. |
| 2014/0172077 A1 | 6/2014 | Bruchman et al. |
| 2014/0172082 A1 | 6/2014 | Bruchman et al. |
| 2014/0194981 A1 | 7/2014 | Menk et al. |
| 2014/0207231 A1 | 7/2014 | Hacohen et al. |
| 2014/0222136 A1 | 8/2014 | Geist et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0249622 A1 | 9/2014 | Carmi et al. |
| 2014/0257467 A1 | 9/2014 | Lane et al. |
| 2014/0277409 A1 | 9/2014 | Bortlein et al. |
| 2014/0277411 A1 | 9/2014 | Bortlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296969 A1 | 10/2014 | Tegels et al. |
| 2014/0324164 A1 | 10/2014 | Gross et al. |
| 2014/0343670 A1 | 11/2014 | Bakis et al. |
| 2014/0358222 A1 | 12/2014 | Gorman, III et al. |
| 2014/0358224 A1 | 12/2014 | Tegels et al. |
| 2015/0018944 A1 | 1/2015 | O'Connell et al. |
| 2015/0032205 A1 | 1/2015 | Matheny |
| 2015/0142100 A1 | 5/2015 | Morriss et al. |
| 2015/0142103 A1 | 5/2015 | Vidlund |
| 2015/0157457 A1 | 6/2015 | Hacohen |
| 2015/0157458 A1 | 6/2015 | Thambar et al. |
| 2015/0173896 A1 | 6/2015 | Richter et al. |
| 2015/0173897 A1 | 6/2015 | Raanani et al. |
| 2015/0196390 A1 | 7/2015 | Ma et al. |
| 2015/0196393 A1 | 7/2015 | Vidlund et al. |
| 2015/0216661 A1 | 8/2015 | Hacohen et al. |
| 2015/0238313 A1 | 8/2015 | Spence et al. |
| 2015/0245934 A1* | 9/2015 | Lombardi ............ A61F 2/2436 623/2.11 |
| 2015/0250588 A1 | 9/2015 | Yang et al. |
| 2015/0272730 A1 | 10/2015 | Melnick et al. |
| 2015/0272734 A1 | 10/2015 | Sheps et al. |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0351903 A1 | 12/2015 | Morriss et al. |
| 2015/0351904 A1 | 12/2015 | Cooper et al. |
| 2015/0351906 A1 | 12/2015 | Hammer et al. |
| 2015/0359629 A1 | 12/2015 | Ganesan et al. |
| 2015/0359631 A1 | 12/2015 | Sheahan et al. |
| 2016/0030169 A1 | 2/2016 | Shahriari |
| 2016/0030171 A1 | 2/2016 | Quijano et al. |
| 2016/0089482 A1 | 3/2016 | Siegenthaler |
| 2016/0100939 A1 | 4/2016 | Amstrong et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0158497 A1 | 6/2016 | Tran et al. |
| 2016/0175095 A1 | 6/2016 | Dienno et al. |
| 2016/0184098 A1 | 6/2016 | Vaturi |
| 2016/0262885 A1 | 9/2016 | Sandstrom et al. |
| 2016/0270911 A1 | 9/2016 | Ganesan et al. |
| 2016/0310268 A1 | 10/2016 | Oba et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0331525 A1 | 11/2016 | Straubinger et al. |
| 2016/0331526 A1 | 11/2016 | Schweich, Jr. et al. |
| 2016/0338706 A1 | 11/2016 | Rowe |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0049435 A1 | 2/2017 | Sauer et al. |
| 2017/0056166 A1 | 3/2017 | Ratz et al. |
| 2017/0056171 A1 | 3/2017 | Cooper et al. |
| 2017/0065411 A1 | 3/2017 | Grundeman et al. |
| 2017/0128205 A1* | 5/2017 | Tamir .................... A61F 2/2436 |
| 2017/0135816 A1 | 5/2017 | Lashinski et al. |
| 2017/0189174 A1 | 7/2017 | Braido et al. |
| 2017/0209264 A1 | 7/2017 | Chau et al. |
| 2017/0224323 A1 | 8/2017 | Rowe et al. |
| 2017/0231757 A1 | 8/2017 | Gassier |
| 2017/0231759 A1 | 8/2017 | Geist et al. |
| 2017/0231766 A1 | 8/2017 | Hariton et al. |
| 2017/0239048 A1 | 8/2017 | Goldfarb et al. |
| 2017/0325948 A1 | 11/2017 | Wallace et al. |
| 2017/0333183 A1 | 11/2017 | Backus |
| 2017/0333187 A1 | 11/2017 | Hariton et al. |
| 2017/0367823 A1 | 12/2017 | Hariton et al. |
| 2018/0000580 A1 | 1/2018 | Wallace et al. |
| 2018/0021129 A1 | 1/2018 | Peterson et al. |
| 2018/0028215 A1 | 2/2018 | Cohen |
| 2018/0049873 A1 | 2/2018 | Manash et al. |
| 2018/0055630 A1 | 3/2018 | Patel et al. |
| 2018/0098850 A1 | 4/2018 | Rafiee et al. |
| 2018/0116843 A1 | 5/2018 | Schreck et al. |
| 2018/0125644 A1 | 5/2018 | Conklin |
| 2018/0153689 A1 | 6/2018 | Maimon et al. |
| 2018/0206983 A1 | 7/2018 | Noe et al. |
| 2018/0214263 A1 | 8/2018 | Rolando et al. |
| 2018/0250126 A1 | 9/2018 | O'Connor et al. |
| 2018/0250130 A1 | 9/2018 | Hariton et al. |
| 2018/0250147 A1 | 9/2018 | Syed |
| 2018/0256323 A1 | 9/2018 | Hariton et al. |
| 2018/0256325 A1 | 9/2018 | Hariton et al. |
| 2018/0271654 A1 | 9/2018 | Hariton et al. |
| 2018/0271655 A1 | 9/2018 | Hariton et al. |
| 2018/0289479 A1 | 10/2018 | Hariton et al. |
| 2018/0296336 A1 | 10/2018 | Cooper et al. |
| 2018/0338829 A1 | 11/2018 | Hariton et al. |
| 2018/0338830 A1 | 11/2018 | Hariton et al. |
| 2018/0338831 A1 | 11/2018 | Hariton et al. |
| 2018/0344457 A1 | 12/2018 | Gross et al. |
| 2018/0353294 A1 | 12/2018 | Calomeni et al. |
| 2018/0360457 A1 | 12/2018 | Ellis et al. |
| 2019/0015093 A1 | 1/2019 | Hacohen et al. |
| 2019/0053896 A1 | 2/2019 | Adamek-Bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0083242 A1 | 3/2019 | Hariton et al. |
| 2019/0083243 A1 | 3/2019 | Hariton et al. |
| 2019/0083246 A1 | 3/2019 | Hariton et al. |
| 2019/0083247 A1 | 3/2019 | Hariton et al. |
| 2019/0105153 A1 | 4/2019 | Barash et al. |
| 2019/0117391 A1 | 4/2019 | Humair |
| 2019/0175339 A1 | 6/2019 | Vidlund |
| 2019/0183639 A1 | 6/2019 | Moore |
| 2019/0192295 A1 | 6/2019 | Spence et al. |
| 2019/0328519 A1 | 10/2019 | Hariton et al. |
| 2019/0336280 A1 | 11/2019 | Naor et al. |
| 2019/0343627 A1 | 11/2019 | Hariton et al. |
| 2019/0350701 A1 | 11/2019 | Adamek-Bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2019/0388223 A1 | 12/2019 | Hariton et al. |
| 2020/0000449 A1 | 1/2020 | Goldfarb et al. |
| 2020/0000579 A1 | 1/2020 | Manash et al. |
| 2020/0015964 A1 | 1/2020 | Noe et al. |
| 2020/0030098 A1 | 1/2020 | Delgado et al. |
| 2020/0046497 A1 | 2/2020 | Hariton et al. |
| 2020/0054335 A1 | 2/2020 | Hernandez et al. |
| 2020/0054451 A1 | 2/2020 | Hariton et al. |
| 2020/0060818 A1 | 2/2020 | Geist et al. |
| 2020/0069424 A1 | 3/2020 | Hariton et al. |
| 2020/0113677 A1 | 4/2020 | McCann et al. |
| 2020/0113689 A1 | 4/2020 | McCann et al. |
| 2020/0113692 A1 | 4/2020 | McCann et al. |
| 2020/0129294 A1 | 4/2020 | Hariton et al. |
| 2020/0138567 A1 | 5/2020 | Marr et al. |
| 2020/0146671 A1 | 5/2020 | Hacohen et al. |
| 2020/0163761 A1 | 5/2020 | Hariton et al. |

(56) References Cited

U.S. PATENT DOCUMENTS

| | | | |
|---|---|---|---|
| 2020/0214832 A1 | 7/2020 | Metchik et al. |
| 2020/0237512 A1 | 7/2020 | McCann et al. |
| 2020/0246136 A1 | 8/2020 | Marr et al. |
| 2020/0246140 A1 | 8/2020 | Hariton et al. |
| 2020/0253600 A1 | 8/2020 | Darabian |
| 2020/0261094 A1 | 8/2020 | Goldfarb et al. |
| 2020/0315786 A1 | 10/2020 | Metchik et al. |
| 2020/0337842 A1 | 10/2020 | Metchik et al. |
| 2021/0085455 A1 | 3/2021 | Bateman et al. |
| 2021/0093449 A1 | 4/2021 | Hariton et al. |
| 2021/0113331 A1 | 4/2021 | Quadri et al. |

FOREIGN PATENT DOCUMENTS

| | | | | |
|---|---|---|---|---|
| EP | 1264582 A2 | 12/2002 | | |
| EP | 1637092 A2 | 3/2006 | | |
| EP | 2349124 B1 | 10/2018 | | |
| EP | 3583922 A1 | 12/2019 | | |
| EP | 3270825 B1 | 4/2020 | | |
| EP | 2485795 B1 | 9/2020 | | |
| WO | WO 2003/020179 A1 | 3/2003 | | |
| WO | WO 2004/028399 A2 | 4/2004 | | |
| WO | WO 2006/007389 A1 | 1/2006 | | |
| WO | WO 2006/086434 A1 | 8/2006 | | |
| WO | WO 2006/116558 A2 | 11/2006 | | |
| WO | WO 2006/128193 A3 | 11/2006 | | |
| WO | WO 2007/047488 A2 | 4/2007 | | |
| WO | WO 2008/029296 A2 | 3/2008 | | |
| WO | WO 2009/091509 A1 | 7/2009 | | |
| WO | WO 2010/006627 A1 | 1/2010 | | |
| WO | WO 2010/027485 A1 | 3/2010 | | |
| WO | WO 2010/045297 A2 | 4/2010 | | |
| WO | WO 2010/057262 A1 | 5/2010 | | |
| WO | WO 2011/069048 A2 | 6/2011 | | |
| WO | WO 2011/144351 A2 | 11/2011 | | |
| WO | WO 2012/011108 A2 | 1/2012 | | |
| WO | WO 2012/036740 A2 | 3/2012 | | |
| WO | WO 2012/048035 A2 | 4/2012 | | |
| WO | WO 2013/059747 A1 | 4/2013 | | |
| WO | WO 2013/072496 A1 | 5/2013 | | |
| WO | WO 2013/078497 A1 | 6/2013 | | |
| WO | WO 2013/114214 A2 | 8/2013 | | |
| WO | WO 2013/175468 A2 | 11/2013 | | |
| WO | WO 2014/115149 A2 | 7/2014 | | |
| WO | WO 2014/144937 A2 | 9/2014 | | |
| WO | WO 2014/164364 A1 | 10/2014 | | |
| WO | WO 2016/016899 A1 | 2/2016 | | |
| WO | WO 2016/098104 A2 | 6/2016 | | |
| WO | WO 2016/125160 | * | 8/2016 | ........... A61F 2/2409 |
| WO | WO 2016/125160 A1 | 8/2016 | | |
| WO | WO 2016/150806 A1 | 9/2016 | | |
| WO | WO 2018/025260 A1 | 2/2018 | | |
| WO | WO 2018/025263 A2 | 2/2018 | | |
| WO | WO 2018/029680 A1 | 2/2018 | | |
| WO | WO 2018/039631 A1 | 3/2018 | | |
| WO | WO 2018/112429 A1 | 6/2018 | | |
| WO | WO 2018/118717 A1 | 6/2018 | | |
| WO | WO 2018/131042 A1 | 7/2018 | | |
| WO | WO 2018/131043 A1 | 7/2018 | | |
| WO | WO 2019/027507 A1 | 2/2019 | | |
| WO | WO 2019/195860 A2 | 10/2019 | | |
| WO | WO 2020/167677 A1 | 8/2020 | | |

OTHER PUBLICATIONS

International Search Report dated Mar. 27, 2018, by the European Patent Office in PCT/IL2017/050849 (5 pages).
International Search Report dated May 30, 2016, by the European Patent Office in PCT/IL2016/050125 (6 pages).
International Search Report dated Nov. 24, 2017, by the European Patent Office in PCT/IL2017/050873 (5 pages).
International Search Report dated Oct. 27, 2015, by the European Patent Office in PCT/IL2015/050792 (3 pages).
International Search Report dated Sep. 4, 2014, by the European Patent Office in PCT/IL2014/050087 (6 pages).
Written Opinion of the International Searching Authority issued by the United States Patent and Trademark Office in PCT/IL2011/000582 (12 pages).
Written Opinion of the International Searching Authority issued by the European Patent Office in PCT/IL2017/050849 (10 pages).
Written Opinion of the International Searching Authority issued by the European Patent Office in PCT/IL2016/050125 (7 pages).
Written Opinion of the International Searching Authority issued by the European Patent Office in PCT/IL2014/050087 (10 pages).
Written Opinion of the International Searching Authority issued by the European Patent Office in PCT/IL2015/050792 (5 pages).
Written Opinion of the International Searching Authority issued by the European Patent Office in PCT/IL2017/050873 (12 pages).
Sundermann, Simon H. et al., *Feasibility of the Engager™ aortic transcatheter valve system using a flexible over-the-wire design*, 42 European Journal of Cardio-Thoracic Surgery, Jun. 27, 2012, at e48 (5 pages).
Symetis S.A., Clinical Investigation Plan for ACURATE Neo™ TA Delivery System, Protocol Jan. 2015, ver. 2, ClinicalTrials.gov Identifier NCT02950428, Sep. 8, 2015 (76 pages).
Tchetche, Didier et al., *New-generation TAVI devices: description and specifications*, 10 EuroIntervention (Supplement), Sep. 2014, at U90 (11 pages).
Batista, Randas J. V. et al., *Partial Left Ventriculectomy to Treat End-Stage Heart Disease*, 64 Annals Thoracic Surgery 634-38 (1997) (5 pages).
Beall, Jr., Arthur C. et al., *Clinical Experience with a Dacron Velour-Covered Teflon-Disc Mitral-Valve Prosthesis*, 5 Annals Thoracic Surgery 402-10 (1968) (9 pages).
Fucci, Carlo et al., *Improved Results with Mitral Valve Repair Using New Surgical Techniques*, 9 Eur. J. Cardiothoracic Surgery 621-27 (1995) (7 pages).
Maisano, Francesco et al., *The Edge-To-Edge Technique: A Simplified Method to Correct Mitrel Insufficiency*, 13 Eur. J. Cardiothoracic Surgery 240-46 (1998) (7 pages).
Stone, Gregg W. et al., *Clinical Trial Design Principles and Endpoint Definitions for Transcatheter Mitrel Valve Repair and Replacement: Part 1: Clinical Trial Design Principles*, 66 J. Am. C. Cardiology 278-307 (2015) (30 pages).
Poirier, Nancy et al., *A Novel Repair for Patients with Atrioventricular Septal Defect Requiring Reoperation for Left Atrioventricular Valve Regurgitation*, 18 Eur. J. Cardiothoracic Surgery 54-61 (2000) (8 pages).
Ando, Tomo et al., *Iatrogenic Ventricular Septal Defect Following Transcatheter Aortic Valve Replacement: A Systematic Review*, 25 Heart, Lung, and Circulation 968-74 (2016) (7 pages).
Urina, Marina et al., *Transseptal Transcatheter Mitral Valve Replacement Using Balloon-Expandable Transcatheter Heart Valves*, JACC: Cardiovascular Interventions 1905-19 (2017) (15 pages).
*Edwards Lifesciences Corp.v. Cardiovalve Ltd.*, IPR2021-00383, Exhibit 1014: Transcript of proceedings held May 20, 2021 (May 26, 2021) (21 pages).
*Edwards Lifesciences Corp.v. Cardiovalve Ltd.*, IPR2021-00383, Exhibit 1015: Facilitate, Merriam-Webster.com, https://www.www.merriam-webster.com/dictionary/facilitate (accessed May 27, 2021) (5 pages).
*Edwards Lifesciences Corp.v. Cardiovalve Ltd.*, IPR2021-00383, Paper 12: Petitioners' Authorized Reply to Patent Owner's Preliminary Response (May 27, 2021) (9 pages).
*Edwards Lifesciences Corp.v. Cardiovalve Ltd.*, IPR2021-00383, Paper 13: Patent Owner's Authorized Surreply to Petitioner's Reply to Patent Owner's Preliminary Response (Jun. 4, 2021) (8 pages).
*Edwards Lifesciences Corp.v. Cardiovalve Ltd.*, IPR2021-00383, Paper 16: Institution Decision (Jul. 20, 2021) (51 pages).
*Edwards Lifesciences Corporation and Edwards Lifesciences LLC*, Petitioner v. *Cardiovalve Ltd.*, Patent Owner, Case No. IPR2021-00383, U.S. Pat. No. 10,226,341, Deposition of Dr. Ivan Vesely, Ph D., Washington, D.C., Sep. 22, 2021, reported by Mary Ann Payonk, Job No. 199935, TSG Reporting-Worldwide, Cardiovalve Exhibit 2010, 170 pgs.

(56) References Cited

OTHER PUBLICATIONS

Fann, James I., et al., "Beating Heart Catheter-Based Edge-to-Edge Mitral Valve Procedure in a Porcine Model, Efficacy and Hearing Response," Circulation, 110:988-993, originally published Aug. 9, 2004, 6 pgs.

Feldman, Ted et al., "Percutaneous Mitral Valve Repair Using the Edge-to-Edge Technique, Six-Month Results of the EVEREST Phase I Clinical Trial," *J Am Coll Cardiol, 2005; vol. 46, No. 11, 2134-40*, available online Oct. 19, 2005, 7 pgs.

Feldman, Ted et al., "Percutaneous Mitral Repair With the MitraClip System, Safety and Midterm Durability in the Initial EVEREST (Endovascular Valve Edge-to-Edge REpair Study) Cohort," *J Am Coll Cardiol*, 2009;54:686-94, available online Aug. 11, 2009, 9 pgs.

Feldman, Ted et al., "Percutaneous Mitral Leaflet Repair: MitraClip® Therapy for Mitral Regurgitation," *Informa Healthcare, ©2012, ISBN: 13:978-1-84184-966-9*, Version Date Jan. 16, 2005, 8 pgs.

Fucci, C. et al., "Improved Results with Mitral Valve Repair Using New Surgical Techniques," EurJ Cardio-thorac Surg, © Springer-Verlag 1995, *EurJ Cardio-thorac Surg*, (1995) 9: 621-627, published Nov. 1, 1995, 7 pgs.

Maisano, Francesco et al., "The Evolution From Surgery to Percutaneous Mitral Valve Interventions, The Role of the Edge-to-Edge Technique," *J Am Coll Cardiol*, 2011;58:2174-82, available online Nov. 8, 2011, 9 pgs.

Maisano, F. et al., "The Edge-to-Edge Technique: A Simplified Method to Correct Mitral Insufficiency," *European Journal of Cardio-thoracic Surgery 13* (1998) 240-246, published Mar. 1, 1998, 7 pgs.

*Edwards Lifesciences Corporation and Edwards Lifesciences LLC*, Petitioner v. *Cardiovalve Ltd.* , Patent Owner, IPR2021-00383, U.S. Pat. No. 10,226,341, Patent Owner's Response Pursuant to 37 C.F.R. § 42.120, 75 pgs.

*Edwards Lifesciences Corporation and Edwards Lifesciences LLC*, Petitioner v. *Cardiovalve Ltd.* , Patent Owner, IPR2021-00383, U.S. Pat. No. 10,226,341, Second Declaration of Dr. Michael Sacks, Cardiovalve Exhibit 2014, 28 pgs.

*Edwards Lifesciences Corporation and Edwards Lifesciences LLC*, Petitioner v. *Cardiovalve Ltd.* , Patent Owner, IPR2021-00383, U.S. Pat. No. 10,226,341, Patent Owner's Contingent Motion to Amend under 37 C.F.R. §42.121, 35 pgs.

*Edwards Lifesciences Corp.v. Cardiovalve Ltd.* , IPR2021-00383, Paper 10: Decision Granting Institution Of Inter Partes Review (Dec. 10, 2021) (42 pages).

*Edwards Lifesciences Corp.v. Cardiovalve Ltd.* , IPR2021-00383, Petitioners' Opposition to Patent Owner's Contingent Motion to Amend (Jan. 5, 2022) (32 pages).

*Edwards Lifesciences Corp.v. Cardiovalve Ltd.* , IPR2021-00383, Petitioners' Reply to Patent Owner's Response (Jan. 5, 2022) (41 pages).

* cited by examiner

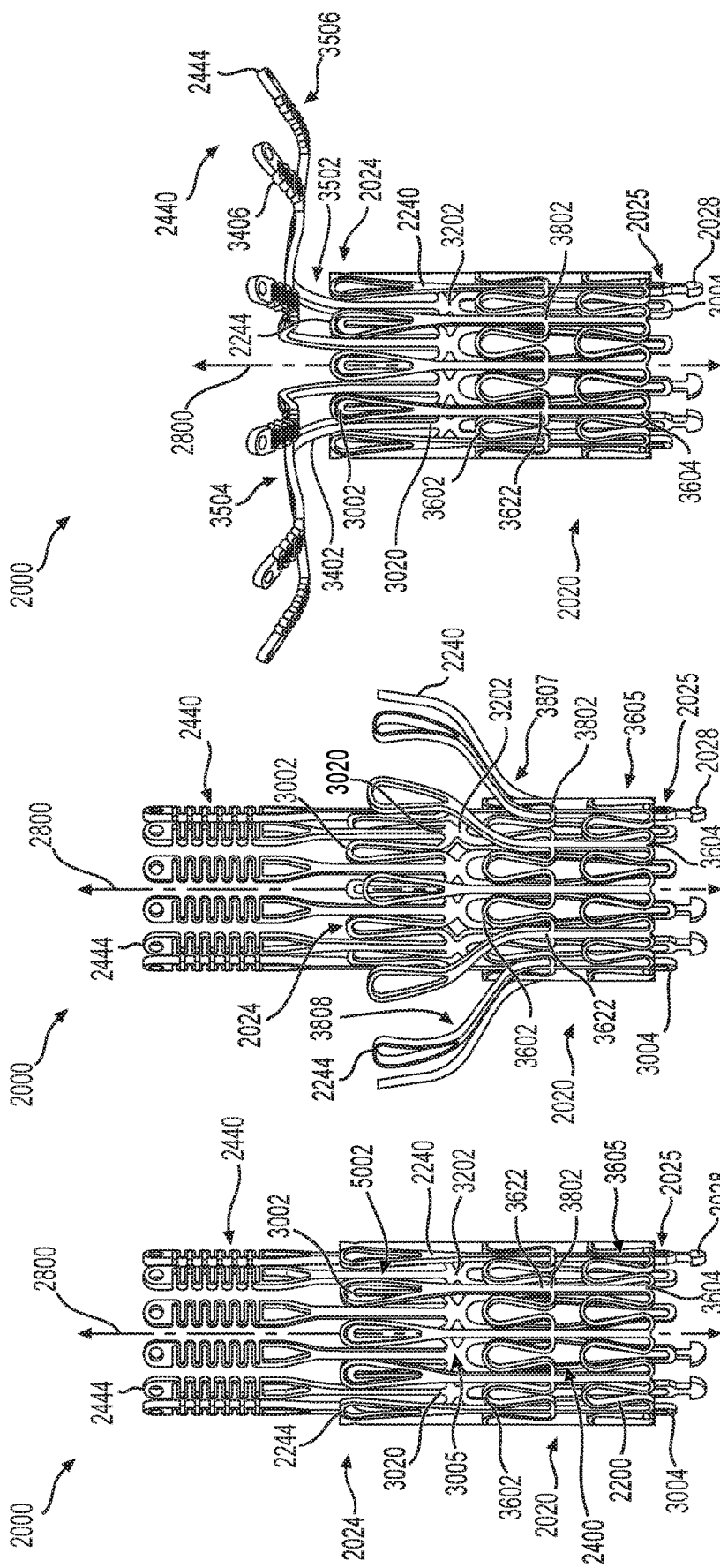

PROSTHETIC VALVE DELIVERY SYSTEM WITH MULTI-PLANAR STEERING

CROSS-REFERENCE TO RELATED APPLICATION

This application claims priority from U.S. Provisional Patent Application No. 62/560,384, filed Sep. 19, 2017, which is hereby incorporated by reference in its entirety.

TECHNICAL FIELD

This disclosure relates generally to prosthetic valves and delivery systems for prosthetic valves. More specifically, this disclosure relates to delivery systems for implantation of prosthetic valves and methods thereof.

BACKGROUND

The native heart valves (the tricuspid valve, pulmonary valve, mitral valve, and aortic valve) play an important role in regulating flow of blood through the cardiovascular system. However, the native heart valves may become damaged or impaired, such as due to cardiovascular diseases, infections, or congenital malformations, thus limiting the ability of the native heart valves to regulate blood flow. This deficiency may result in reduced cardiovascular function or even death.

To treat these conditions, prosthetic heart valves may be implanted at or near the site of a damaged or impaired native valve. A prosthetic heart valve may assist or replace the functionality of an impaired native valve, leading to better regulation of blood flow and improved cardiovascular function. However, many existing prosthetic heart valves require implantation via an open heart procedure, which is highly-invasive and may cause life-threatening complications. Other prosthetic valves may be collapsed within a prosthetic valve delivery system and advanced into the heart, at which point the prosthetic valve may be removed from the delivery system and expanded at the native valve site. However, many of these prosthetic valves are large in size and therefore difficult to deliver into the heart without causing damage to healthy tissue along the implantation route. In addition, once these prosthetic valves are situated within the heart, they may be difficult to securely implant at the native valve site due to their complex structure and the limited maneuverability of existing prosthetic valve delivery systems within the heart. Moreover, many prosthetic valves are so large that they may protrude several centimeters into surrounding heart chambers once they are implanted, impairing cardiac filling and causing injury to the anatomy within the heart.

Thus, there remains a need for prosthetic heart valves that are smaller in size yet still configured to assist or replace the functionality of a diseased or damaged native heart valve. In addition, there remains a need for prosthetic heart valves that are more easily maneuvered into the heart and securely implanted at the site of a native heart valve. Moreover, there remains a need for improved prosthetic heart valve delivery systems that are configured to securely implant a prosthetic heart valve at an implantation site. The present disclosure provides prosthetic heart valves with a reduced axial length such that the prosthetic heart valves may be more easily delivered into the heart and may exhibit lower protrusion into the chambers of the heart. The present disclosure also provides improved prosthetic heart valve delivery systems and methods of implanting prosthetic heart valves therewith, such that prosthetic heart valves may be securely anchored at the implantation site.

SUMMARY

Disclosed herein are systems and methods for implantation of prosthetic valves by prosthetic valve delivery systems. Particular examples of the disclosure may pertain to a prosthetic valve delivery system configured for multi-planar steering and having a delivery capsule configured to retain a prosthetic valve therein.

According to an exemplary embodiment of the present disclosure, a prosthetic valve delivery system is provided. The prosthetic valve delivery system includes a first catheter, a first steering mechanism, a second catheter, a second steering mechanism, and a capsule. The first steering mechanism is configured to bend the first catheter within a first steering plane. The second catheter is coaxially arranged within the first catheter. The second steering mechanism is configured to bend the second catheter within a second steering plane. The second steering plane is different from the first steering plane. The capsule is positioned distal to both the first catheter and the second catheter. The capsule is configured to retain a prosthetic valve therein during transvascular advancement.

The first steering plane is orthogonal to the second steering plane. The first catheter is configured to remain substantially straightened while the second catheter bends within the second steering plane. The first catheter and the second catheter are each configured to bend by an angle greater than 90°. The first catheter and the second catheter are each configured to bend by an angle no greater than 120°. The prosthetic valve delivery system additionally includes a third catheter coaxially arranged within the second catheter. The capsule is connected to the third catheter. At least a portion of the capsule is configured for longitudinal movement relative to the third catheter. The first catheter, the second catheter, and the third catheter are all configured for relative longitudinal movement. The first catheter and the second catheter are configured to bend the third catheter by an angle greater than 180°. The capsule includes a distal capsule portion and a proximal capsule portion. The distal capsule portion and the proximal capsule portion are configured for movement in opposing directions. The distal capsule portion is configured to retain a ventricular portion of the prosthetic valve therein. The proximal capsule portion is configured to retain an atrial portion of the prosthetic valve therein. The distal capsule portion is configured to retain an annular valve body of the prosthetic valve and a plurality of ventricular anchoring legs of the prosthetic valve therein. The proximal capsule portion is configured to retain a plurality of atrial anchoring arms of the prosthetic valve therein. The distal capsule portion is configured to release the ventricular anchoring legs while the annular valve body remains retained therein. The capsule further includes a valve anchor configured to secure the prosthetic valve during movement of one or more of the distal capsule portion and the proximal capsule portion. The prosthetic valve delivery system additionally includes a first capsule actuator and a second capsule actuator. The first capsule actuator is configured to effect longitudinal movement of the distal capsule portion relative to the valve anchor. The second capsule actuator is configured to effect longitudinal movement of the proximal capsule portion relative to the valve anchor. The first capsule actuator is configured to move the distal capsule portion to a first position in which a portion of the prosthetic valve is released from the capsule while the prosthetic valve remains secured relative to the capsule. The first capsule actuator is also configured to move the distal capsule portion to a second position in which the prosthetic valve is released from the capsule. The prosthetic valve delivery system additionally includes a handle configured to enable rotation of the first catheter and the second catheter. The prosthetic valve delivery system additionally includes a first catheter actuator and a second catheter actuator. The first catheter actuator is configured to effect bending of the first catheter within the first steering plane. The second catheter actuator is configured to effect longitudinal movement of the second catheter and bending of the second catheter within the second steering plane. The first catheter actuator and second catheter actuator are configured for relative longitudinal movement. The prosthetic valve delivery system additionally includes a catheter lock configured to prevent relative longitudinal movement of the first catheter and the second catheter. The first catheter and the second catheter are configured to advance the capsule through vasculature and across a fossa to position the prosthetic valve within a heart chamber.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIGS. 5A-5E illustrate structural changes in the exemplary frame of FIG. 2A during transitioning of the frame between a radially-contracted configuration and a radially-expanded configuration, consistent with various embodiments of the present disclosure.

DETAILED DESCRIPTION

Figure 1A:
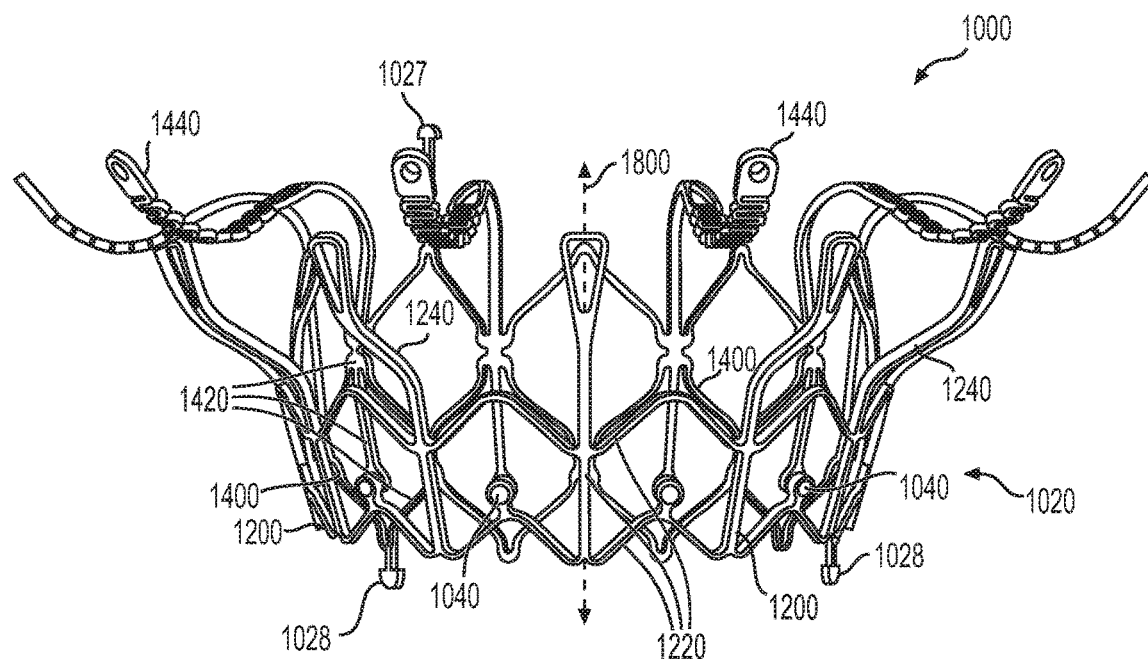
FIG. 1A illustrates a front elevation view of an exemplary frame for a prosthetic valve, consistent with various embodiments of the present disclosure.

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used in the present disclosure and in the appended claims, the singular forms "a," "an," and "the" include plural references unless the context clearly dictates otherwise.

In some embodiments of the present disclosure, an "atrial direction" may refer to a direction extending towards an atrium of the heart. For example, from a location within the left ventricle or the mitral valve, an atrial direction may refer to a direction extending towards the left atrium. Additionally, from a location within an atrium (e.g., the left atrium), an atrial direction may refer to a direction extending away from an adjacent atrioventricular valve (e.g., the mitral valve) and further into the atrium. For example, in FIGS. 10G and 10H, an atrial direction may refer to a direction extending upwards from prosthetic valve 6000 towards atrium 9010. In some exemplary embodiments, an atrial direction need not necessarily be parallel to a longitudinal axis of a prosthetic valve (e.g., longitudinal axis 2800 illustrated in FIG. 2A), so long as the direction is angled towards an atrium. The atrial direction may be parallel to a longitudinal axis of a prosthetic valve in some cases. In some embodiments, a "non-ventricular direction" may refer to a direction that does not extend towards a ventricle of the heart. A "non-ventricular direction" may extend in an atrial direction, or it may extend laterally in a direction perpendicular to a ventricular direction.

In some exemplary embodiments of the present disclosure, a "ventricular direction" may refer to a direction extending towards a ventricle of the heart. From a location within the left atrium or the mitral valve, a ventricular direction may refer to a direction extending towards the left ventricle. Additionally, from a location within a ventricle (e.g., the left ventricle), a ventricular direction may refer to a direction extending away from an adjacent atrioventricular valve (e.g., the mitral valve) and further into the ventricle. For example, in FIGS. 10G and 10H, a ventricular direction may refer to a direction extending downwards from prosthetic valve 6000 towards ventricle 9020. In some exemplary embodiments, a ventricular direction need not necessarily be parallel to a longitudinal axis of a prosthetic valve (e.g., longitudinal axis 2800 illustrated in FIG. 2A), so long as the direction is angled towards a ventricle. The ventricular direction may be parallel to a longitudinal axis of a prosthetic valve in some cases. In some embodiments, a "non-atrial direction" may refer to a direction that does not extend towards an atrium of the heart. A non-atrial direction may extend in a ventricular direction, or it may extend laterally in a direction perpendicular to an atrial direction.

Exemplary embodiments generally relate to prosthetic valves for implantation within a native valve and methods for implanting prosthetic valves within a native valve. In addition, exemplary embodiments generally relate to systems and methods for implantation of prosthetic valves by prosthetic valve delivery systems. While the present disclosure provides examples relating to prosthetic heart valves, and in particular prosthetic mitral valves, as well as delivery systems for prosthetic heart valves, it should be noted that aspects of the disclosure in their broadest sense are not limited to a prosthetic heart valve. Rather, the foregoing principles may be applied to other prosthetic valves as well. In various embodiments in accordance with the present disclosure, the term prosthetic valve refers generally to an implantable valve configured to restore and/or replace the functionality of a native valve, such as a diseased or otherwise impaired native heart valve.

An exemplary prosthetic valve may include a prosthetic valve configured to render a native valve structure non-functional, and may thus replace the function of the native valve. For example, an exemplary prosthetic valve may have a size and shape similar to the valve being replaced and may include a number of leaflet-like structures to regulate fluid flow and prevent backflow of blood through the valve. Additionally, or alternatively, an exemplary prosthetic valve may also include a prosthetic valve configured to leave the native valve structure intact and functional. An exemplary prosthetic valve may include a mitral valve, tricuspid valve, aortic valve, or pulmonary valve, as well as a valve outside of the heart, such as a venous valve, lymph node valve, ileocecal valve, or any other structure configured to control and/or regulate fluid flow in the body. An exemplary prosthetic valve may additionally or alternatively be configured to replace a failed bioprosthesis, such as a failed heart valve prosthesis.

Figure 1B:
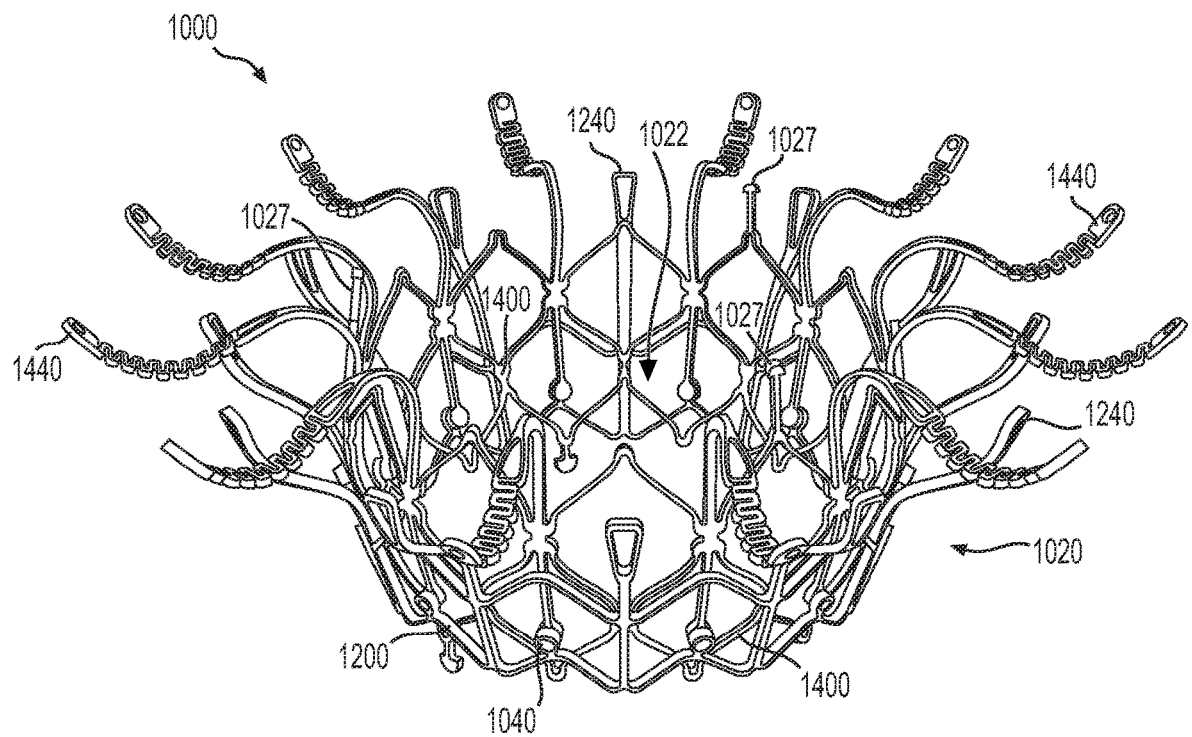
FIG. 1B illustrates a perspective view of the exemplary frame of FIG. 1A, consistent with various embodiments of the present disclosure.

FIG. 1A illustrates a front elevation view of an exemplary frame 1000 for a prosthetic valve. FIG. 1B illustrates a perspective view of frame 1000. Frame 1000 may be constructed of a shape memory material such as nickel titanium alloy (Nitinol) and may be configured to support other components of the prosthetic valve, such as prosthetic leaflets and protective cover layers. Frame 1000 may include an annular outer frame 1200 and an inner frame 1400 situated at least partially within the outer frame 1200. Annular outer frame 1200 and inner frame 1400 may be secured together by pins, screws, welding, soldering, adhesive, magnets, and/or any other suitable mechanism. For example, FIGS. 1A and 1B depict annular outer frame 1200 and inner frame 1400 connected by a plurality of connector pins 1040.

Annular outer frame 1200 may include an outer frame tubular portion 1220, which may be formed of a plurality of struts intersecting at junctions to form a wire mesh, stent-like, or cage-like structure of the outer frame tubular portion 1220. Annular outer frame 1200 may also include at least one ventricular anchoring leg 1240, which may be configured to extend radially outward from the outer frame tubular portion and which may contact, or otherwise engage, tissue within or near the native valve to anchor the prosthetic valve within the native valve. In some embodiments, exemplary valve frame 1000 may include twelve ventricular anchoring legs 1240, which may be configured to engage ventricular tissue of a native atrioventricular valve.

Inner frame 1400 may include an inner frame tubular portion 1420, which may be formed of a plurality of struts intersecting at junctions to form a wire mesh, stent-like, or cage-like structure of the inner frame tubular portion 1420. Inner frame 1400 may also include at least one atrial anchoring arm 1440, which may be configured to extend radially outward from the inner frame tubular portion and which may contact, or otherwise engage, tissue within or near the native valve to anchor the prosthetic valve within the native valve. In some embodiments, exemplary valve frame 1000 may include twelve atrial anchoring arms 1440, which may be configured to engage atrial tissue of a native atrioventricular valve.

Outer frame tubular portion 1220 and inner frame tubular portion 1420 may together form an annular valve body 1020 of the prosthetic valve, which may have at least one opening and from which the ventricular anchoring legs 1240 and atrial anchoring arms 1440 may extend. Annular valve body 1020 may include an axial lumen 1022 extending through the annular valve body 1020 along a longitudinal axis 1800 of the prosthetic valve. In some embodiments, annular valve body 1020 may be configured to receive a flow control device, such as one or more prosthetic leaflets, within axial lumen 1022. Optionally, annular valve body 1020 may include one or more atrial end delivery posts 1027 along an atrial end (i.e., top end) of the annular valve body and/or one or more ventricular end delivery posts 1028 along a ventricular end (i.e., bottom end) of the annular valve body. Delivery posts 1027 and 1028 may be configured to removably engage a delivery device of the prosthetic valve, for example, to assist with placement of frame 1000 within or near a native valve.

Figure 2A:
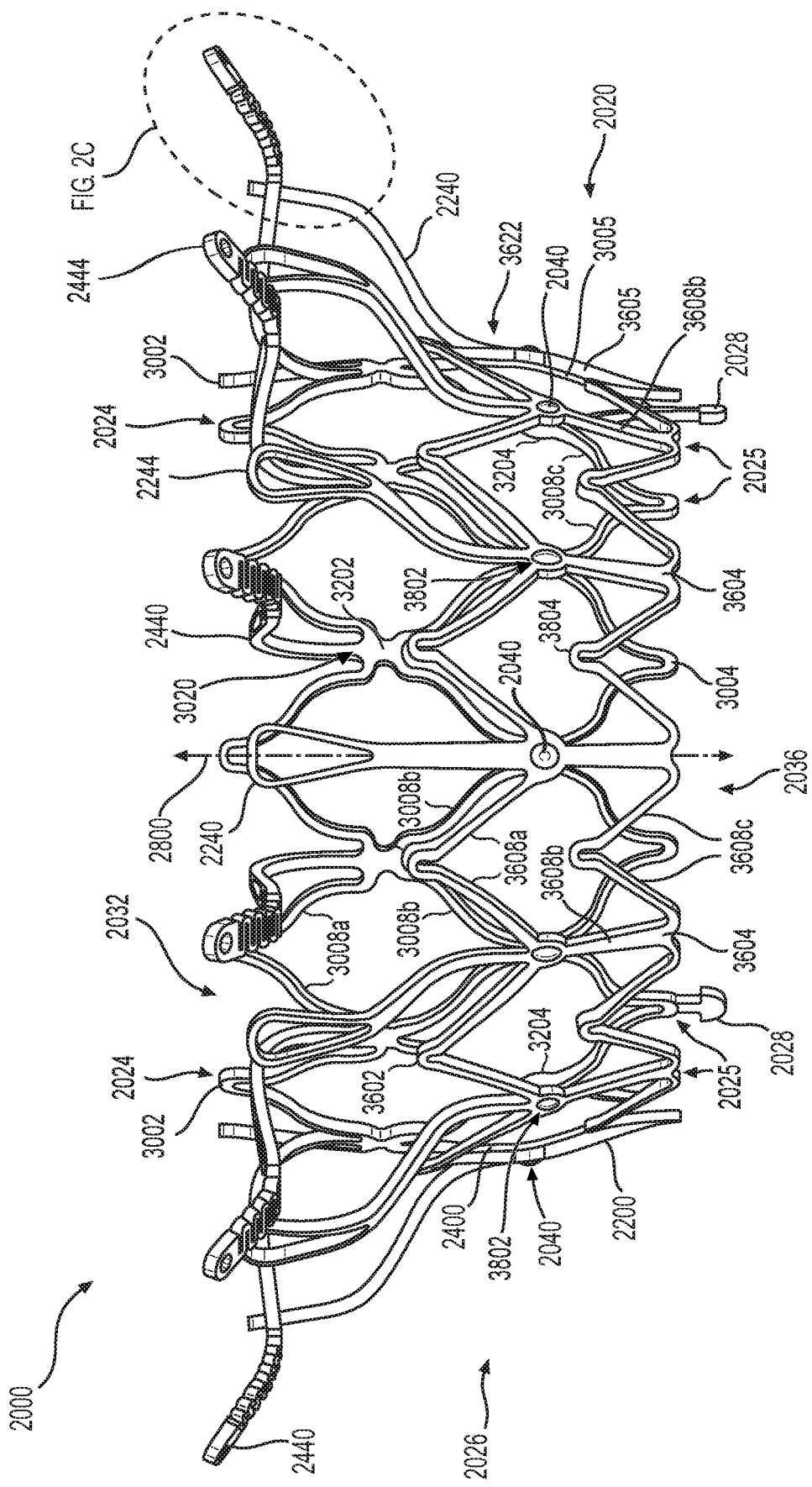
FIG. 2A illustrates a front elevation view of another exemplary frame for a prosthetic valve, consistent with various embodiments of the present disclosure.
Figure 2B:
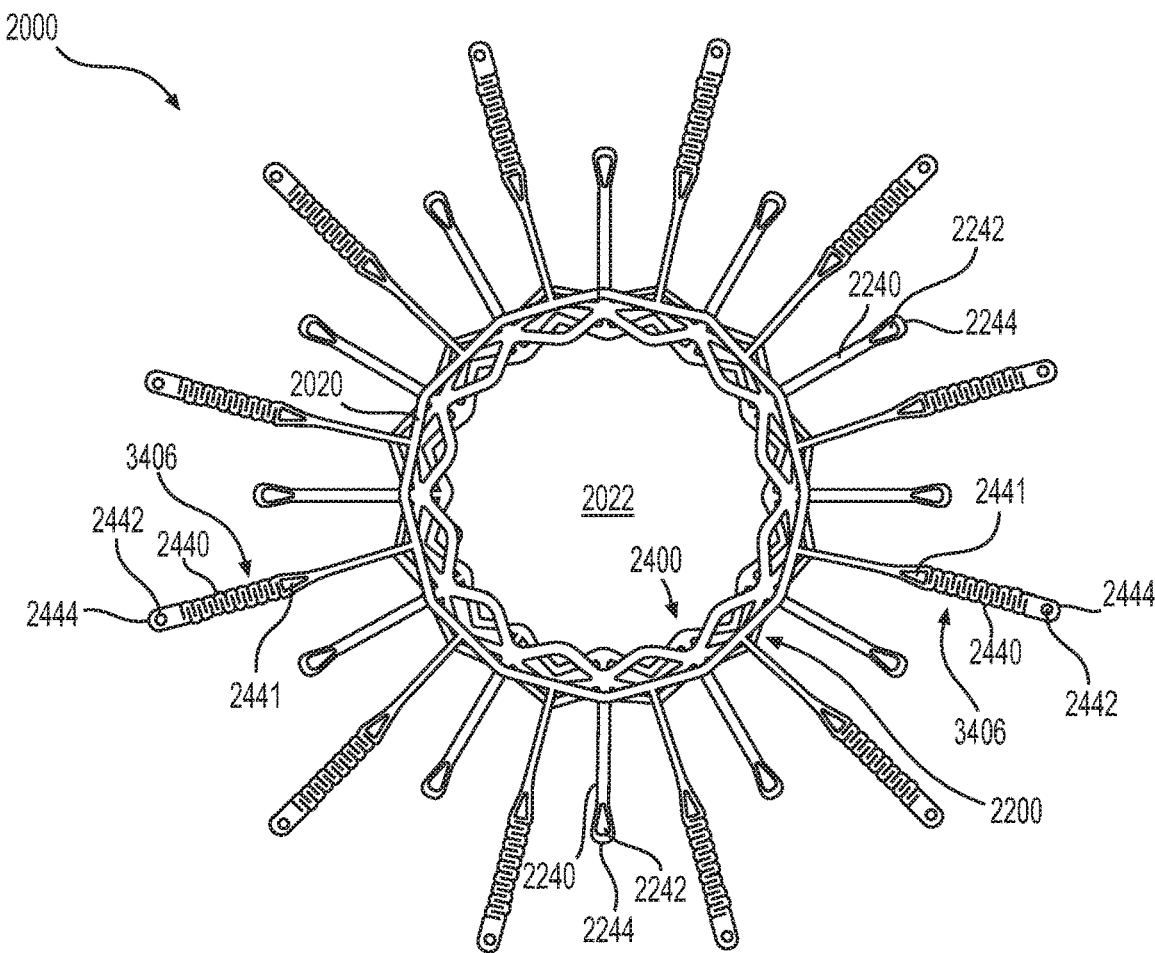
FIG. 2B illustrates a top plan view of the exemplary frame of FIG. 2A, consistent with various embodiments of the present disclosure.

FIG. 2A illustrates a front view of another exemplary frame 2000 for a prosthetic valve. FIG. 2B illustrates a top plan view of the frame 2000. Frame 2000 may include an annular outer frame 2200 and an inner frame 2400 situated at least partially within the annular outer frame 2200. Annular outer frame 2200 and inner frame 2400 may be secured together by pins, screws, welding, soldering, adhesive, magnets, and/or any other suitable mechanism. For example, FIGS. 2A and 2B depict annular outer frame 2200 and inner frame 2400 connected by a plurality of connector pins 2040.

Annular outer frame 2200 may include an outer frame tubular portion 3605, which may be formed of a plurality of struts intersecting at junctions to form a wire mesh, stent-like, or cage-like structure of the outer frame tubular portion 3605. For example, as illustrated in FIG. 2A, annular outer frame 2200 may include outer frame atrial circumferential struts 3608a, outer frame leg base struts 3608b, and outer frame ventricular circumferential struts 3608c intersecting at atrial end outer frame junctions 3602, leg attachment junctions 3802, outer frame junctions 3804, and ventricular end outer frame junctions 3604 to form outer frame tubular portion 3605. Annular outer frame 2200 may also include at least one ventricular anchoring leg 2240, which may extend from leg attachment junction 3802 of the outer frame tubular portion 3605 and which may be configured to engage ventricular tissue of a native valve to anchor the prosthetic valve in the native valve. The at least one ventricular anchoring leg 2240 may include a proximal leg end 3622, which may be the end of the leg connected to the outer frame tubular portion, and a distal leg end 2244, which may be situated radially outward from the outer frame tubular portion. As shown in FIG. 2B, the at least one ventricular anchoring leg 2240 may include at least one opening 2242.

Inner frame 2400 may include an inner frame tubular portion 3005, which may be formed of a plurality of struts intersecting at junctions to form a wire mesh, stent-like, or cage-like structure of the inner frame tubular portion 3005. For example, as illustrated in FIG. 2A, inner frame 2400 may include inner frame atrial struts 3008a, inner frame intermediate struts 3008b, and inner frame ventricular struts 3008c intersecting at atrial end inner frame junctions 3002, arm attachment junctions 3202, inner frame strut junctions 3204, and ventricular end inner frame junctions 3004 to form inner frame tubular portion 3005. Inner frame 2400 may also include at least one atrial anchoring arm 2440, which may extend from arm attachment junction 3202 of the inner frame tubular portion 3005 and which may be configured to engage atrial tissue of a native valve to anchor the prosthetic valve in the native valve. The at least one atrial anchoring arm 2440 may include a proximal arm end 3020, which may be the end of the arm connected to the inner frame tubular portion, and a distal arm end 2444, which may be situated radially outward from the inner frame tubular portion. As shown in FIG. 2B, the at least one atrial anchoring arm 2440 may include a proximal arm opening 2441 and a distal arm opening 2442.

Outer frame tubular portion 3605 and inner frame tubular portion 3005 may together form an annular valve body 2020 of the prosthetic valve, which may have at least one opening and from which the ventricular anchoring legs 2240 and atrial anchoring arms 2440 may extend. Annular valve body 2020 may include an axial lumen 2022 extending through the annular valve body 2020 along a longitudinal axis 2800 of the prosthetic valve. Annular valve body 2020 may have an atrial end 2024, a ventricular end 2025 opposite the atrial end, and an intermediate portion 2026 extending between the atrial and ventricular ends. In some embodiments, the atrial end may refer to the portion of the annular valve body configured to be situated at a location within the atrium that is furthest from an adjacent ventricle, when the prosthetic valve is implanted in a native valve. Similarly, the ventricular end may refer to the portion of the annular valve body configured to be situated at a location within the ventricle that is furthest from an adjacent atrim, when the prosthetic valve is implanted in a native valve. The intermediate portion 2026 may extend between the atrial end 2024 and ventricular end 2025. In some embodiments, annular valve body 2020 may include one or more ventricular end delivery posts 1028 along the ventricular end 2025 of the annular valve body. Axial lumen 2022 may include an inlet opening 2032 at the atrial end of the annular valve body, as well as an outlet opening 2036 at the ventricular end of the annular valve body.

Figure 2C:
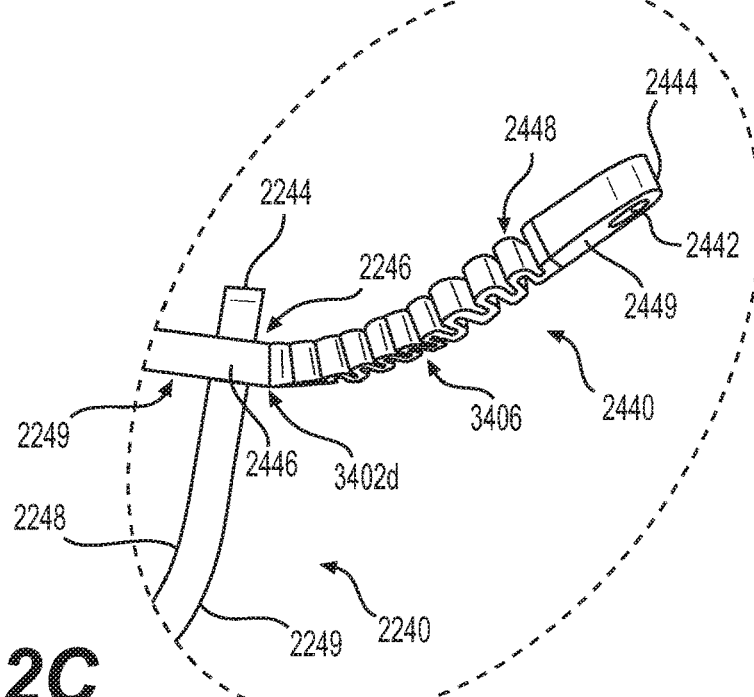
FIG. 2C illustrates an enlarged view of an atrial anchoring arm and a ventricular anchoring leg of the exemplary frame of FIG. 2A, consistent with various embodiments of the present disclosure.

FIG. 2C illustrates an enlarged view of an atrial anchoring arm 2440 and a ventricular anchoring leg 2240 of frame 2000. Ventricular anchoring leg 2240 may include an inner, atrially-facing leg surface 2248 and an outer, ventricularly-facing leg surface 2249. Atrial anchoring arm 2440 may include an atrially-facing arm surface 2448 and a ventricularly-facing arm surface 2449. In some embodiments, atrial anchoring arm 2440 may include an arm portion 2446 configured to be arranged in a common lateral plane with leg portion 2246 of the ventricular anchoring leg 2240. That is, leg portion 2246 and arm portion 2446 may be positioned at the same axial position along longitudinal axis 2800.

Figure 2D:
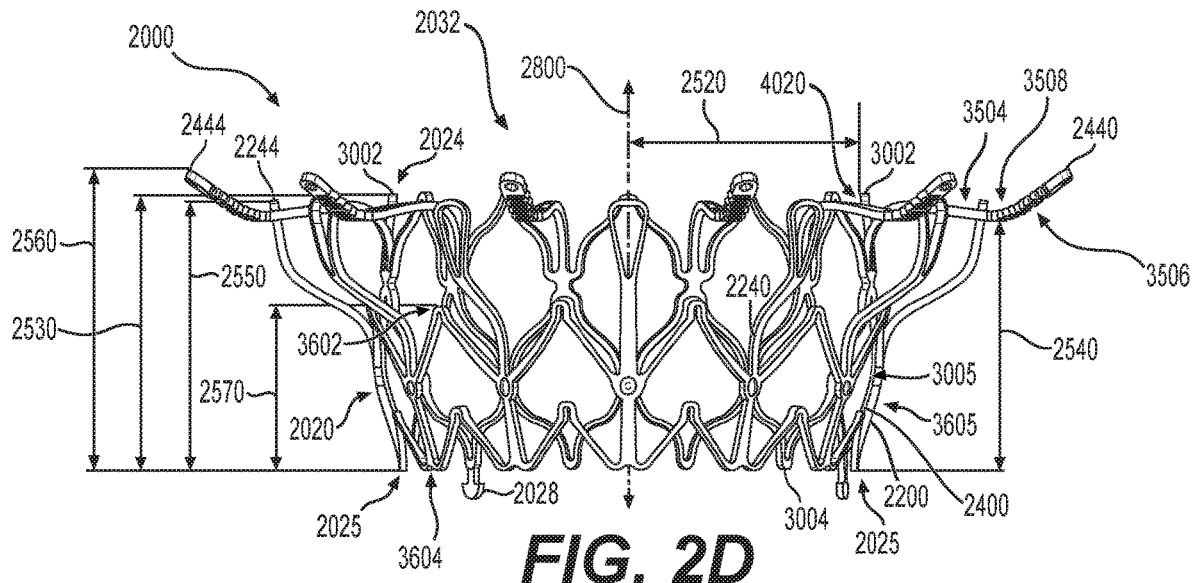
FIG. 2D illustrates another front elevation view of the exemplary frame of FIG. 2A, consistent with various embodiments of the present disclosure.

FIG. 2D illustrates another front elevation view of frame 2000. The exemplary prosthetic valve, as well as frame 2000, may have an axial height 2560, which may extend between terminal arm ends 2444 and ventricular end 2025 of the annular valve body. Inner frame tubular portion 3005 may have an axial height 2530, which may extend between atrial end inner frame junctions 3002 and ventricular end inner frame junctions 3004. Annular outer frame 2200 may have an axial height 2550, which may extend between terminal leg ends 2244 and ventricular end 2025 of the annular valve body. Outer frame tubular portion 3605 may have an axial height 2570, which may extend between atrial end outer frame junctions 3602 and ventricular end outer frame junctions 3604. In some embodiments, frame 2000 may have a ventricular device protrusion distance 2540, which may represent the distance over which the prosthetic valve protrudes into a left ventricle when the prosthetic valve is implanted in a native mitral valve. Annular valve body 2020 may include a valve inlet radius 2520, which may be the radius of atrial inlet opening 2032.

Figure 2E:
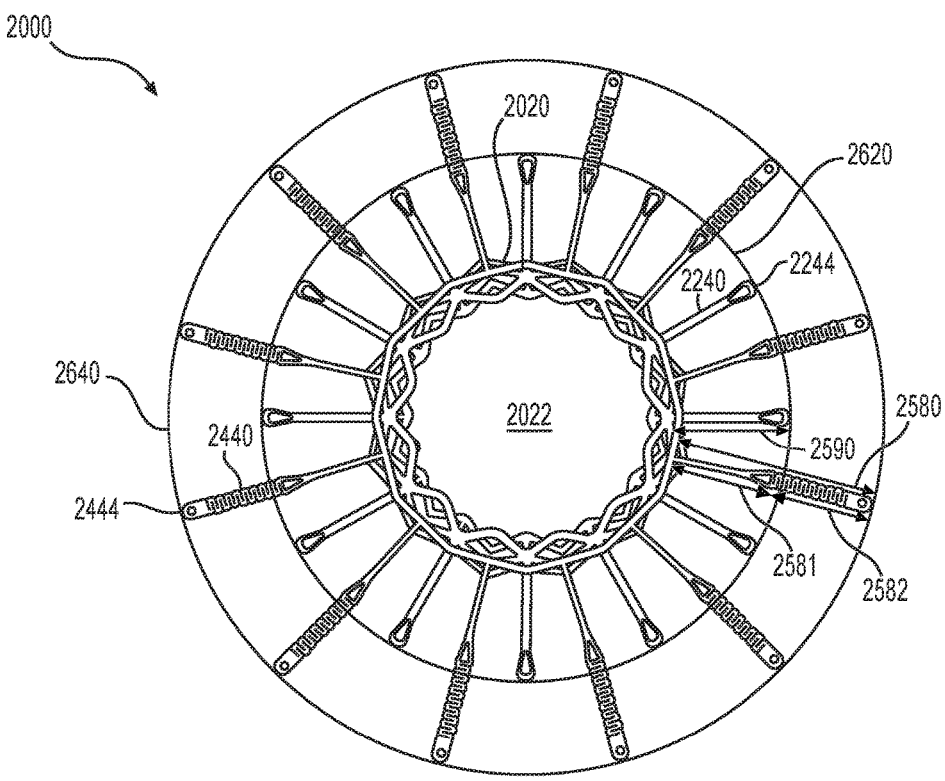
FIG. 2E illustrates another top plan view of the exemplary frame of FIG. 2A, consistent with various embodiments of the present disclosure.

FIG. 2E illustrates another top plan view of frame 2000. The atrial anchoring arms 2440 may have a length 2580, and the ventricular anchoring legs 2240 may have a length 2590. The terminal arm ends 2444 may define an atrial anchoring arm circumference 2640. The terminal leg ends 2244 may define a ventricular anchoring leg circumference 2620, which may be concentric with atrial anchoring arm circumference 2640. Inflexible portions 3402 of the atrial anchoring arms (illustrated in FIG. 3B) may have a length 2581. Serpentine structures 3406 of the atrial anchoring arms (illustrated in FIG. 3B) may have a length 2582.

Figure 3A:
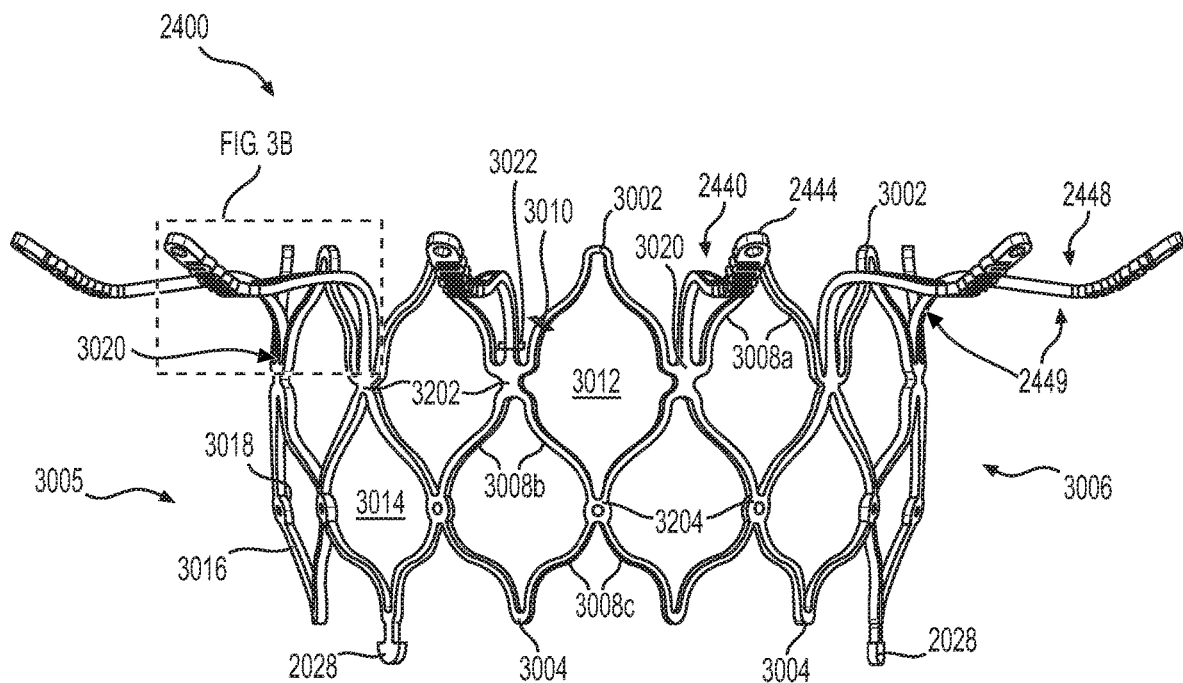
FIG. 3A illustrates a front elevation view of an inner frame of the exemplary frame of FIG. 2A, consistent with various embodiments of the present disclosure.

FIG. 3A illustrates a front elevation view of inner frame 2400. The atrial end inner frame junctions 3002 and ventricular end inner frame junctions 3004 may form the atrial end and ventricular end, respectively, of inner frame 2400. Inner frame intermediate portion 3006 may extend between atrial end inner frame junctions 3002 and ventricular end inner frame junctions 3004. Inner frame tubular portion 3005 may have a radially inner surface 3018 and a radially outer surface 3016. Inner frame atrial struts 3008a and inner frame intermediate struts 3008b may intersect at atrial end inner frame junctions 3002, arm attachment junctions 3202, and strut junctions 3204 to form a first, atrial row of closed cells 3012. Inner frame intermediate struts 3008b and inner frame ventricular struts 3008c may intersect at arm attachment junctions 3202, strut junctions 3204, and ventricular end inner frame junctions 3004 to form a second, ventricular row of closed cells 3014. At least one inner frame atrial strut 3008a may have a cross-sectional area 3010. At least one atrial anchoring arm 2440 may have a cross-sectional area 3022.

Figure 3B:
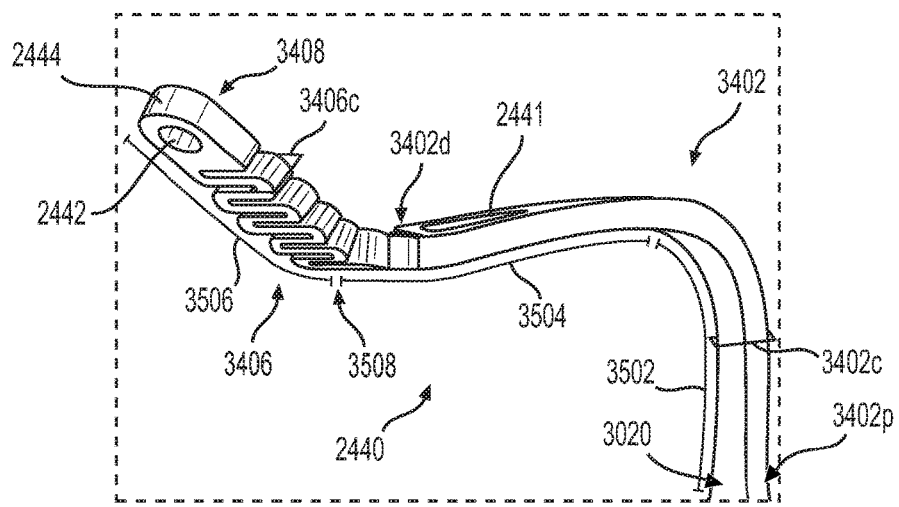
FIG. 3B illustrates an enlarged view of an atrial anchoring arm of the exemplary inner frame of FIG. 3A, consistent with various embodiments of the present disclosure.

FIG. 3B illustrates an enlarged view of an atrial anchoring arm 2440 of inner frame 2400. Atrial anchoring arm 2440 may include a proximal arm portion 3502 configured to extend in an atrial direction, intermediate arm portion 3504 configured to extend in a ventricular direction, and distal arm portion 3506 configured to extend in an atrial direction. Arm transition portion 3508 may represent the transition between intermediate arm portion 3504 and distal arm portion 3506. Atrial anchoring arm 2440 may also include an inflexible portion 3402 extending to proximal arm end 3020, as well as a serpentine structure 3406, which may be situated radially external to the inflexible portion 3402. Inflexible portion 3402 may have a proximal end 3402p, a distal end 3402d, and a cross-sectional area 3402c. Serpentine structure 3406 may have a cross-sectional area 3406c. In some embodiments, atrial anchoring arm 2440 may include a terminal arm region 3408 situated radially external to serpentine structure 3406. Distal arm opening 2442 may be situated within terminal arm region 3408.

Figure 3C:
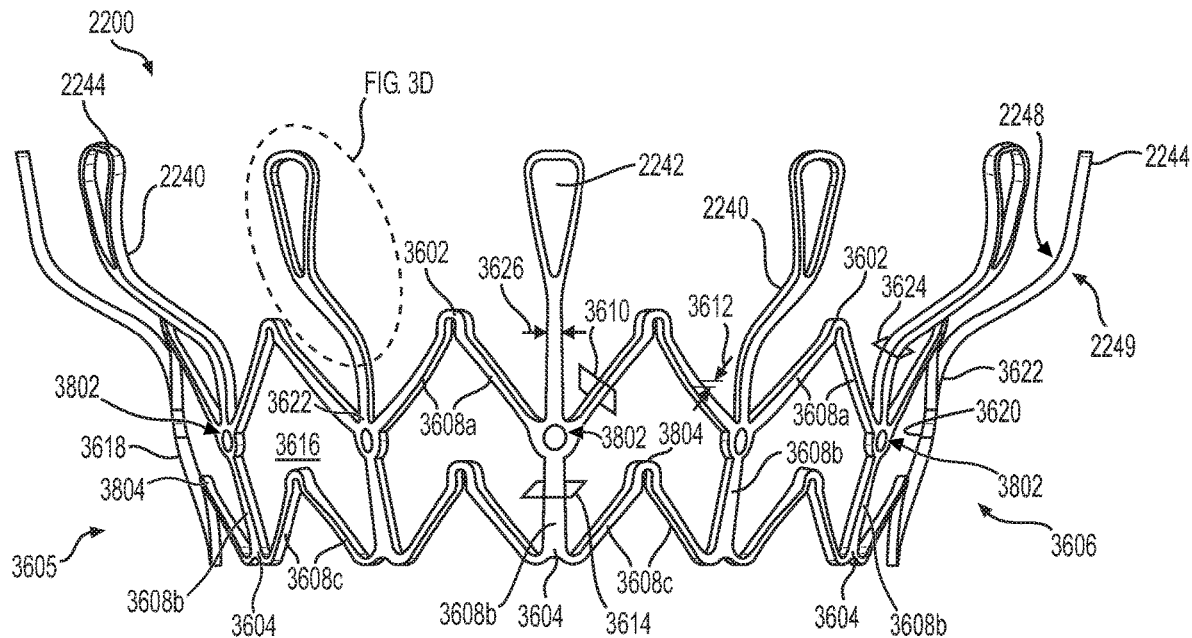
FIG. 3C illustrates a front elevation view of an outer frame of the exemplary frame of FIG. 2A, consistent with various embodiments of the present disclosure.

FIG. 3C illustrates a front elevation view of outer frame 2200. The atrial end outer frame junctions 3602 and ventricular end outer frame junctions 3604 may form the atrial end and ventricular end, respectively, of annular outer frame 2200. Outer frame intermediate portion 3606 may extend between atrial end outer frame junctions 3602 and ventricular end outer frame junctions 3604. Outer frame tubular portion 3605 may have a radially outer surface 3618 and a radially inner surface 3620. The outer frame atrial circumferential struts 3608a, outer frame leg base struts 3608b, and outer frame ventricular circumferential struts 3608c may intersect at the atrial end outer frame junctions 3602, leg attachment junctions 3802, outer frame junctions 3804, and ventricular end outer frame junctions 3604 to form closed cells 3616. At least one outer frame atrial circumferential strut 3608a may have a cross-sectional area 3610 and a width 3612. At least one outer frame leg base strut 3608b may have a cross-sectional area 3614. At least one ventricular anchoring leg may have a cross-sectional area 3624 and a radially outer surface width 3626.

Figure 3D:
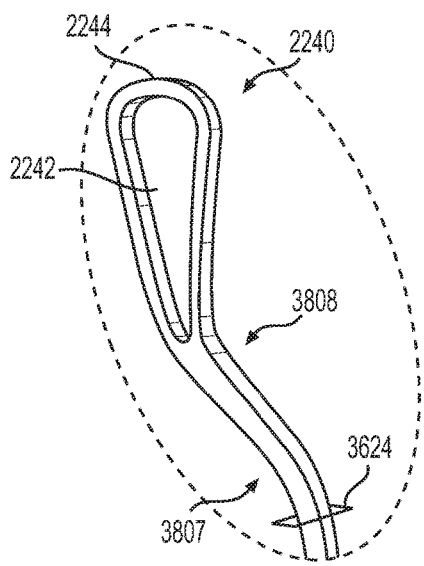
FIG. 3D illustrates an enlarged view of a ventricular anchoring leg of the exemplary outer frame of FIG. 3C, consistent with various embodiments of the present disclosure.

FIG. 3D illustrates an enlarged view of a portion of a ventricular anchoring leg 2240 of annular outer frame 2200. Ventricular anchoring leg 2240 may include a first, proximal curved portion 3807 and a second, distal curved portion 3808. In some embodiments, proximal curved portion 3807 may face radially outward. Additionally, or alternatively, distal curved portion 3808 may face radially inwards.

Figure 4B:
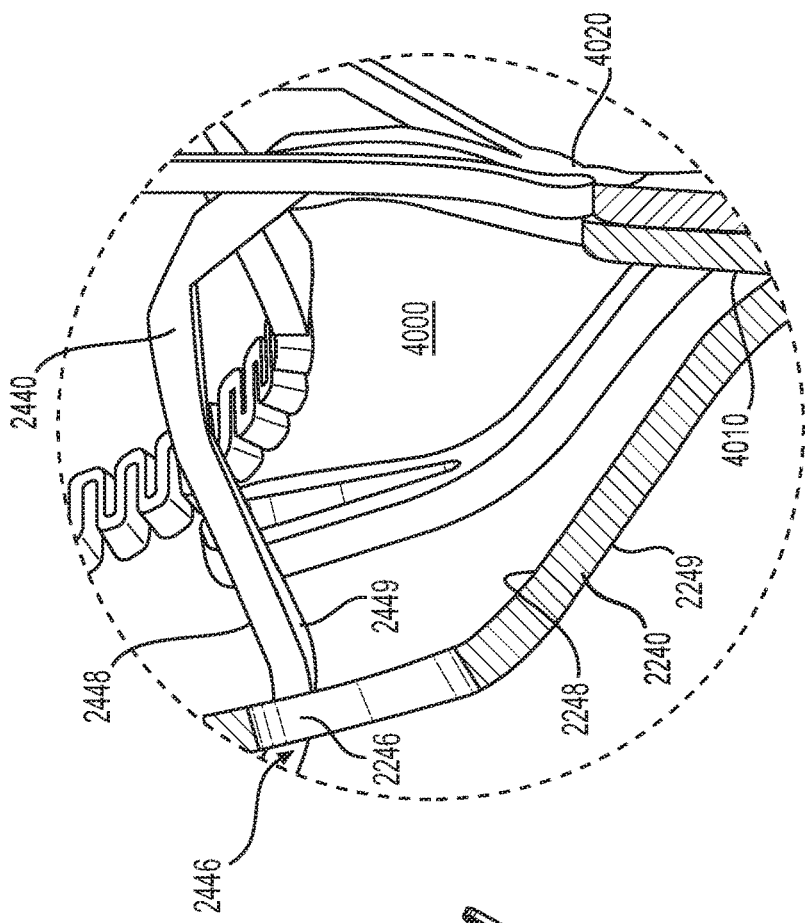
FIG. 4B illustrates an enlarged view of a volume between an atrial anchoring arm and a ventricular anchoring leg of the exemplary frame of FIG. 4A, consistent with various embodiments of the present disclosure.
Figure 4A:
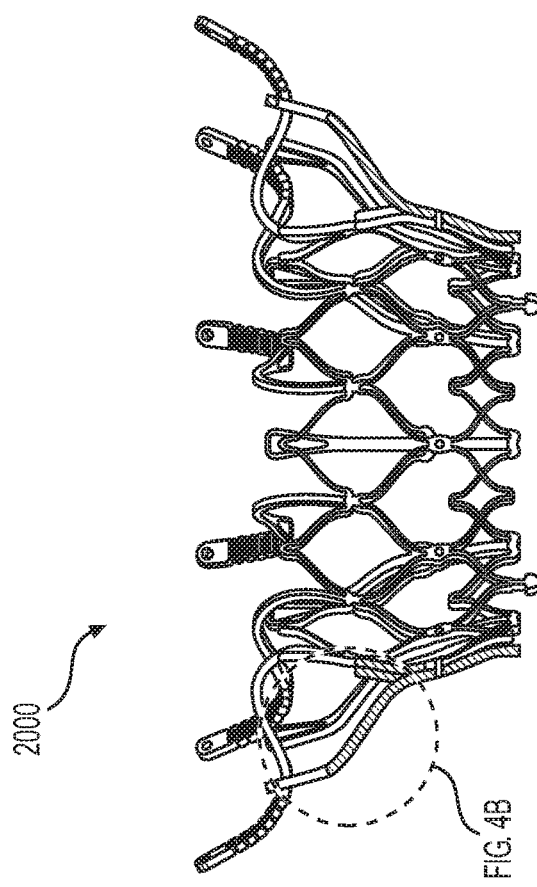
FIG. 4A illustrates a cross-sectional view of the exemplary frame of FIG. 2A, consistent with various embodiments of the present disclosure.

FIG. 4A illustrates a cross-sectional view of frame 2000, and FIG. 4B illustrates an enlarged view of a portion of FIG. 4A depicting a volume 4000 formed between the atrial anchoring arms 2440 and ventricular anchoring legs 2240. FIG. 4B also depicts an outer surface 4010 and inner surface 4020 of annular valve body 2020. In some embodiments, volume 4000 may be bounded by the ventricularly-facing surfaces 2449 of atrial anchoring arms 2440, by the inner, atrially-facing surfaces 2248 of ventricular anchoring legs 2240, and by the outer surface 4010 of the annular valve body 2020.

FIG. 5A illustrates a configuration of the exemplary prosthetic valve in which annular valve body 2020, atrial anchoring arms 2440, and ventricular anchoring legs 2240 are arranged in a radially-contracted configuration. In some embodiments, the configuration illustrated in FIG. 5A may constitute a radially-contracted configuration of the prosthetic valve.

FIG. 5B illustrates a configuration of the exemplary prosthetic valve in which annular valve body 2020 and atrial anchoring arms 2440 are arranged in a radially-contracted configuration. In the configuration of FIG. 5B, the ventricular anchoring legs 2240 may deflect radially outward away from annular valve body 2020, into a radially-expanded configuration of the ventricular anchoring legs 2240.

FIG. 5C illustrates a configuration of the exemplary prosthetic valve in which annular valve body 2020 and ventricular anchoring legs 2240 are arranged in a radially-contracted configuration. In the configuration of FIG. 5C, the atrial anchoring arms 2440 may deflect radially outward away from annular valve body 2020, into a radially-expanded configuration of the atrial anchoring arms 2440.

Figures 5D, 5E:
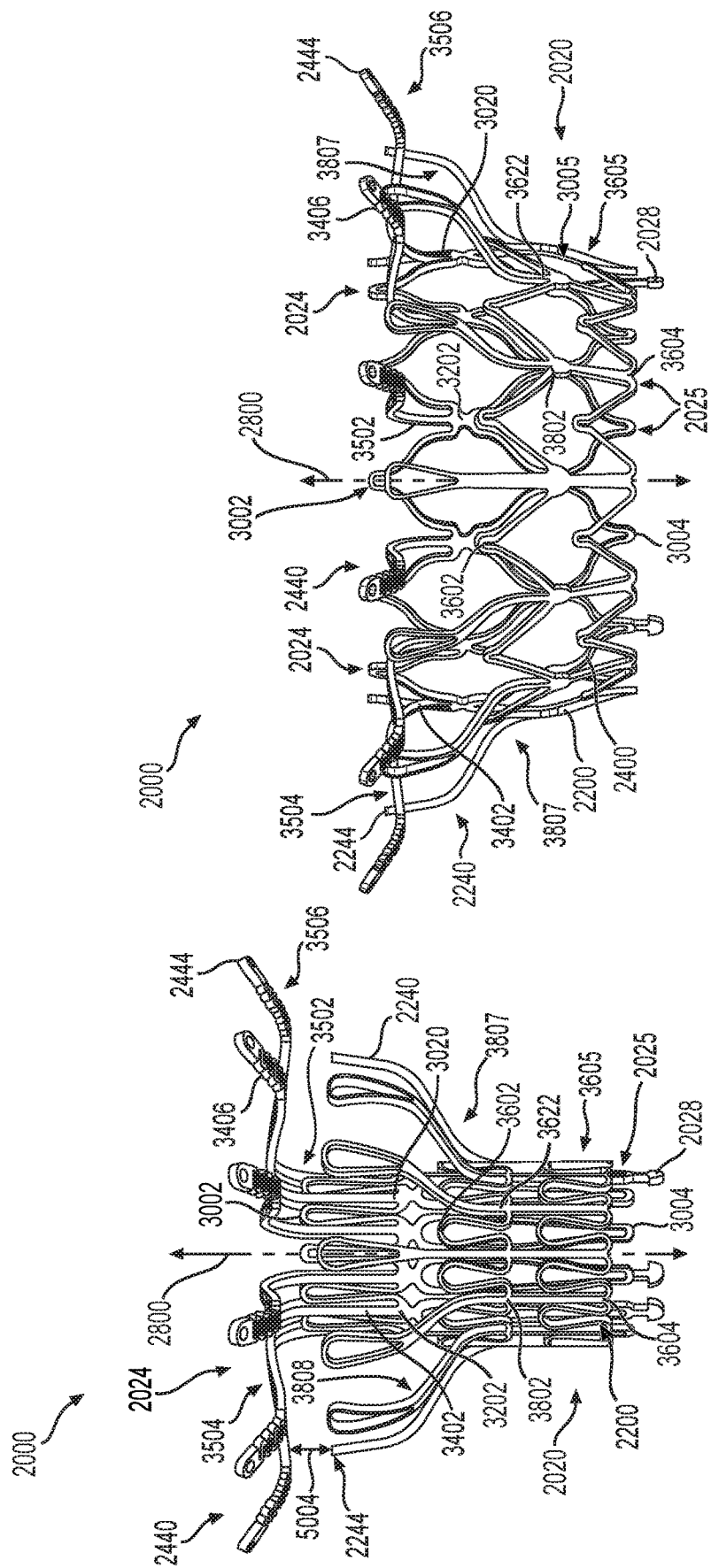

FIG. 5D illustrates a configuration of the exemplary prosthetic valve in which the atrial anchoring arms 2440 and ventricular anchoring legs 2240 may deflect radially outward away from annular valve body 2020 into their respective radially-expanded configurations, while annular valve body 2020 remains in a radially-contracted configuration. In the configuration of FIG. 5D, an axial distance 5004 may be formed between the atrial anchoring arms 2440 and the terminal ends 2244 of the ventricular anchoring legs 2240.

FIG. 5E illustrates a configuration of the exemplary prosthetic valve in which annular valve body 2020, atrial anchoring arms 2440, and ventricular anchoring legs 2240 are arranged in a radially-expanded configuration. In some embodiments, the configuration illustrated in FIG. 5E may constitute a radially-expanded configuration of the prosthetic valve.

Figure 6A:
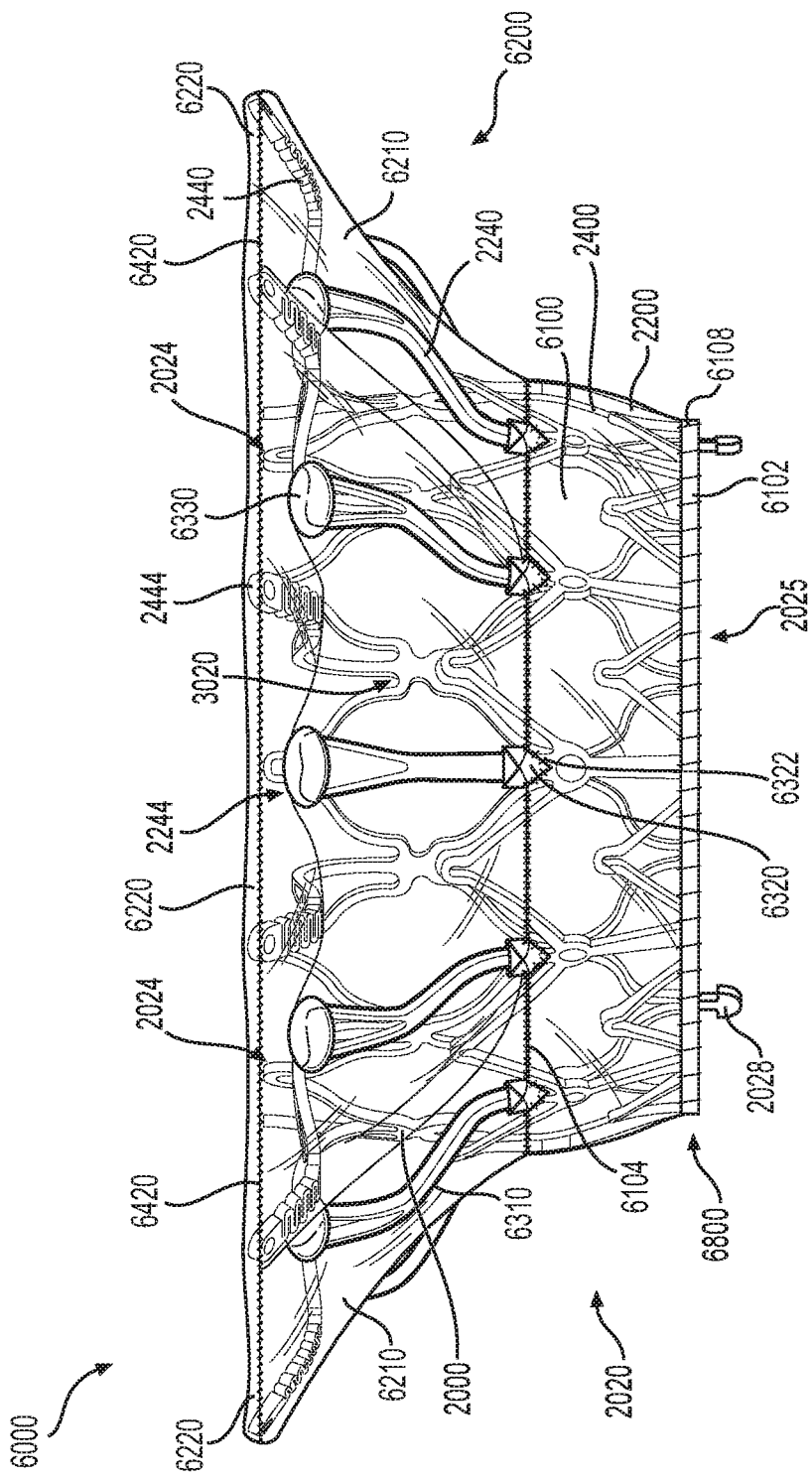
FIG. 6A illustrates a front elevation view of an exemplary prosthetic valve, consistent with various embodiments of the present disclosure.

FIG. 6A illustrates a front elevation view of prosthetic valve 6000. In some embodiments, prosthetic valve 6000 may be assembled upon frame 2000. Prosthetic valve 6000 may be configured for implantation within or near a native valve structure and may be configured to restore and/or replace the functionality of a native valve, such as a diseased or otherwise impaired native valve. Prosthetic valve 6000 may include valve frame 2000, including annular valve body 2020, the atrial anchoring arms 2440, and the ventricular anchoring legs 2240. Prosthetic valve 6000 may also include a skirt layer 6100 configured around an external surface of a portion of the annular valve body. Prosthetic valve 6000 may additionally include a first cuff sheet 6210, which may be connected to skirt layer 6100 via stitching 6104, as well as a second cuff sheet 6220, which may be connected to first cuff sheet 6210 via stitching 6420. In some embodiments, the first cuff sheet 6210 and second cuff sheet 6220 by extend around the terminal ends 2444 of the atrial anchoring arms 2440. Skirt layer 6100, first cuff sheet 6210, and second cuff sheet 6220 may be constructed of fluid-impermeable material and may accordingly be configured to prevent passage of blood or other fluids through portions of the prosthetic valve 6000 outside of the axial lumen 2022.

In some embodiments, prosthetic valve 6000 may additionally include a protective sleeve 6102 wrapped around the rim 6800 of the ventricular outlet opening of annular valve body 2020; protective sleeve 6102 may be secured to annular valve body 2020 by stitching 6108. Additionally, or alternatively, prosthetic valve 6000 may include at least one liner 6310 extending around an external surface of the ventricular anchoring legs 2240, with at least one protective layer 6330 positioned around the distal leg ends 2244 and at least one protective covering 6320 wrapped around the proximal leg ends 3622. In some embodiments, the at least one protective covering 6320 may be secured to the skirt layer 6100 via stitching 6322.

Figure 6B:
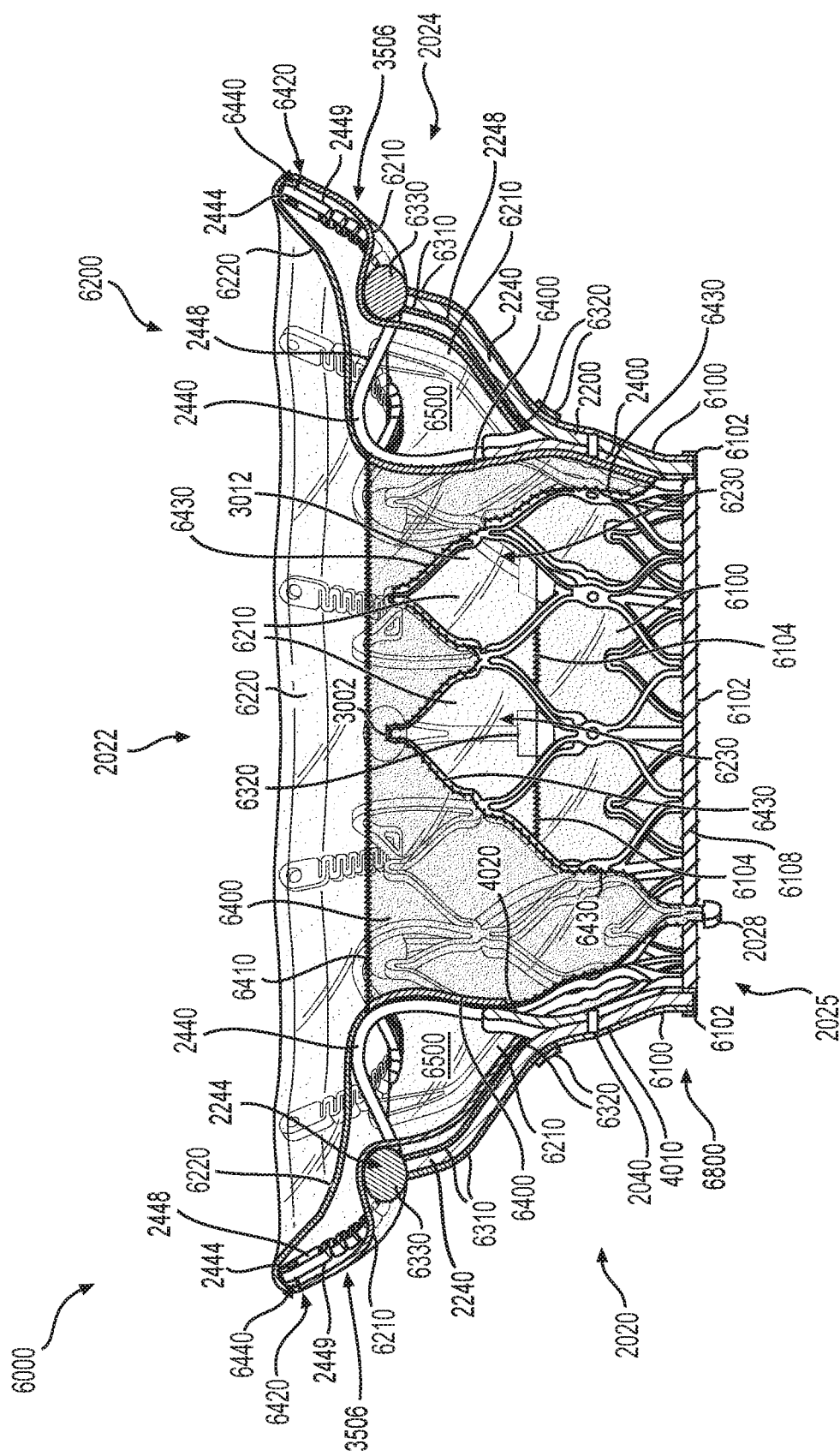
FIG. 6B illustrates a cross-sectional view of the exemplary prosthetic valve of FIG. 6A without leaflets, consistent with various embodiments of the present disclosure.

FIG. 6B illustrates a cross-sectional view of prosthetic valve 6000, without prosthetic leaflets situated within the axial lumen 2022. As illustrated in FIG. 6B, prosthetic valve 6000 may additionally include a liner 6400 covering at least a portion of the inner surface 4020 of the annular valve body 2020. Liner 6400 may be secured to the annular valve body 2020 via stitching 6430 and to the second cuff sheet 6220 via stitching 6410. First cuff sheet 6210, second cuff sheet 6220, and inner liner 6400 may together form an inflatable cuff 6200 having an interior volume 6500. In some embodiments, inflatable cuff 6200 may be secured to atrial anchoring arm 2440 via connector 6440. Blood may enter the cuff 6200 through openings 6230, causing the cuff 6200 to inflate radially outwards and axially in an atrial direction. In some embodiments, cuff 6200 may inflate radially outwards and press against tissue of the native valve. This engagement between the cuff and tissue of the native valve may form a barrier to flow of blood and other fluids around the outer circumference of the prosthetic valve 6000.

Figure 6C:
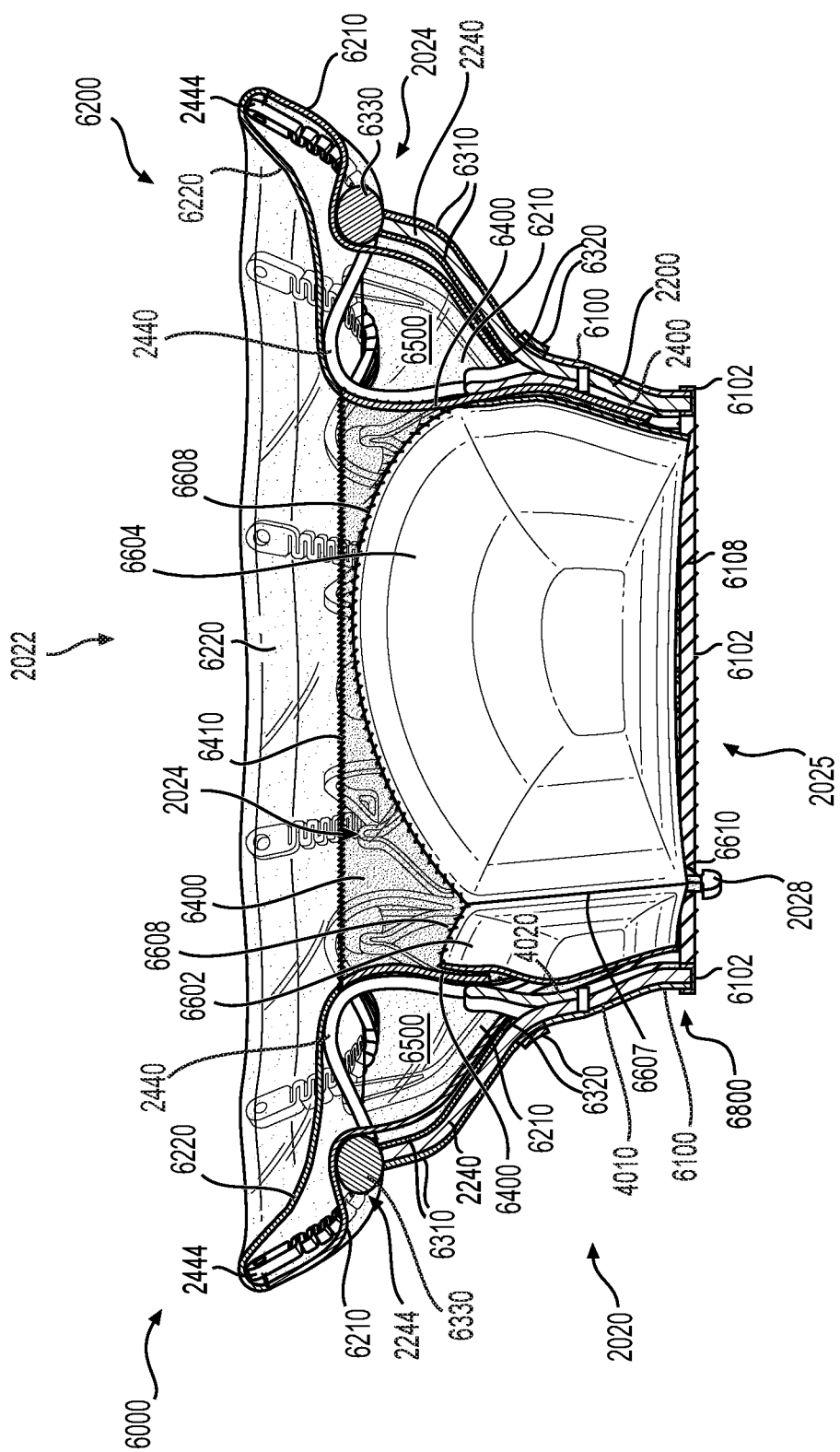
FIG. 6C illustrates a cross-sectional view of the exemplary prosthetic valve of FIG. 6A with leaflets, consistent with various embodiments of the present disclosure.

FIG. 6C illustrates a cross-sectional view of prosthetic valve 6000 with prosthetic leaflets 6602 and 6604 situated within the axial lumen 2022. In some embodiments, prosthetic valve 6000 may also include a third prosthetic leaflet 6606, which may not be visible in the view of FIG. 6C. The leaflets 6602, 6604, and 6606 may be secured to inner liner 6400 via stitching 6608 and may include a connector 6610 wrapping around the ventricular end delivery posts 2028 to secure the leaflets 6602, 6604, and 6606 to the valve frame 2000.

Figure 6D:
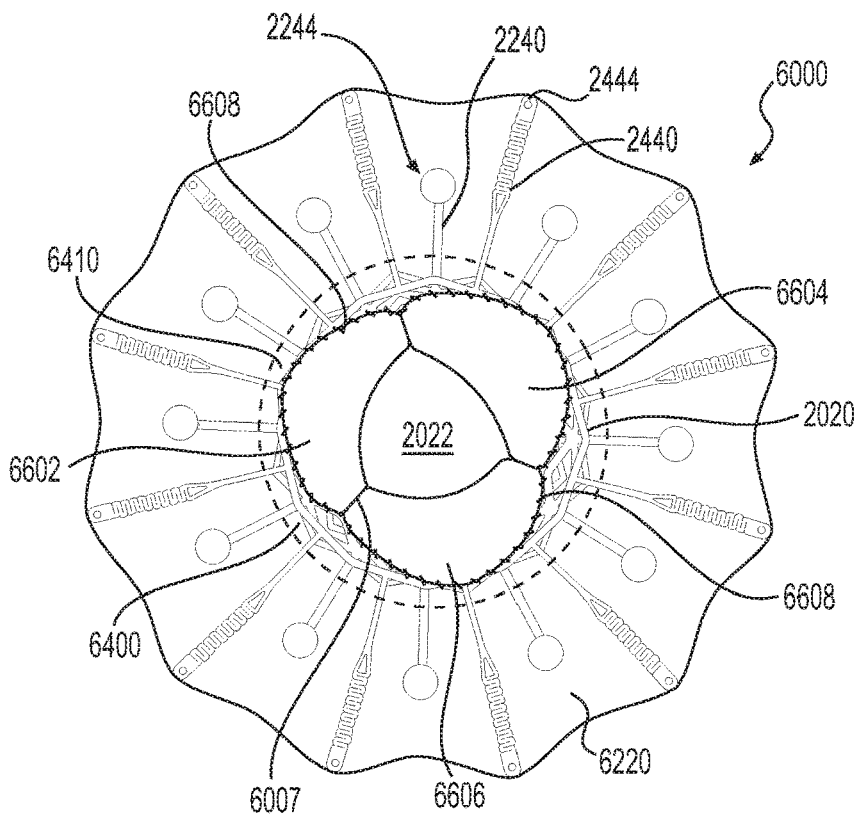
FIG. 6D illustrates a top plan view of the exemplary prosthetic valve of FIG. 6A with uninflated leaflets, consistent with various embodiments of the present disclosure.
Figure 6E:
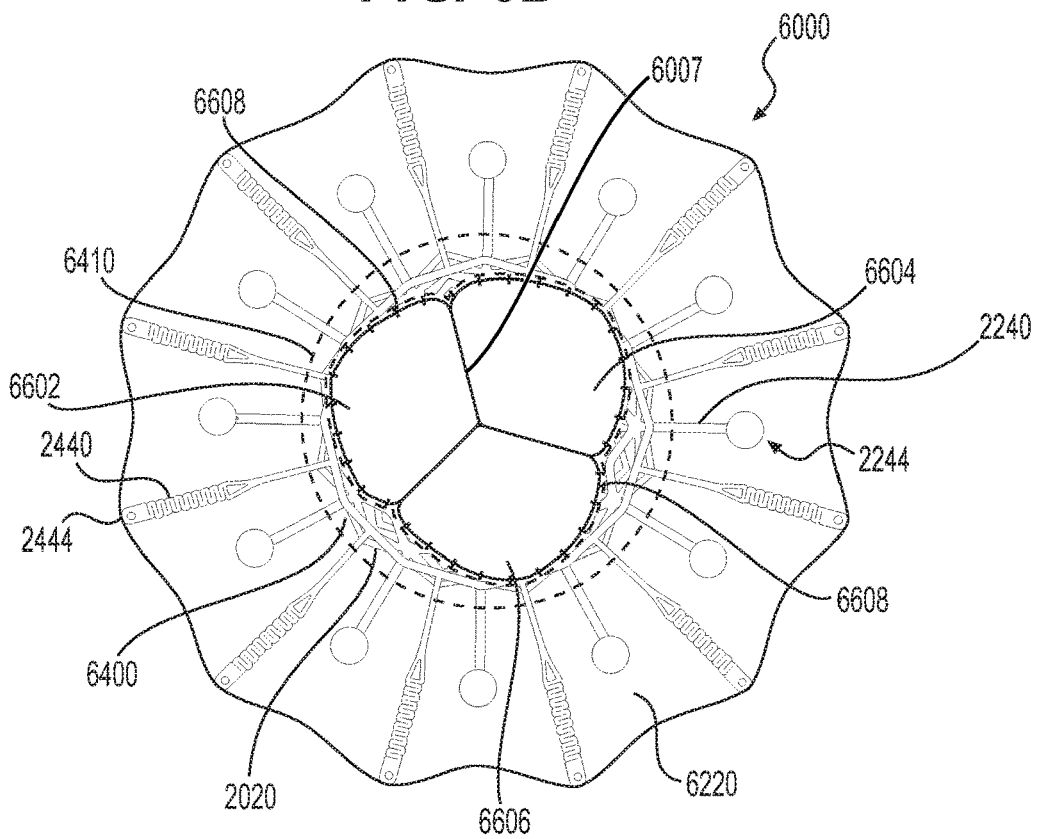
FIG. 6E illustrates a top plan view of the exemplary prosthetic valve of FIG. 6A with inflated leaflets, consistent with various embodiments of the present disclosure.

FIG. 6D illustrates a top plan view of prosthetic valve 6000, with leaflets 6602, 6604, and 6606 arranged in an open, uninflated configuration. In the open configuration, a space may be formed in the middle of the leaflets, permitting fluid to pass through the axial lumen 2022 of the prosthetic valve 6000. FIG. 6E illustrates a top plan view of prosthetic valve 6000, with leaflets 6602, 6604, and 6606 arranged in a closed, coapted configuration. In the closed configuration, the leaflets may press together such that the opening between them is closed. For example, the point of contact 6007 between two adjacent leaflets may extend to the center of the axial lumen; as a result, the leaflets may block fluid passage through the axial lumen 2022 of the prosthetic valve 6000.

Figure 7A:
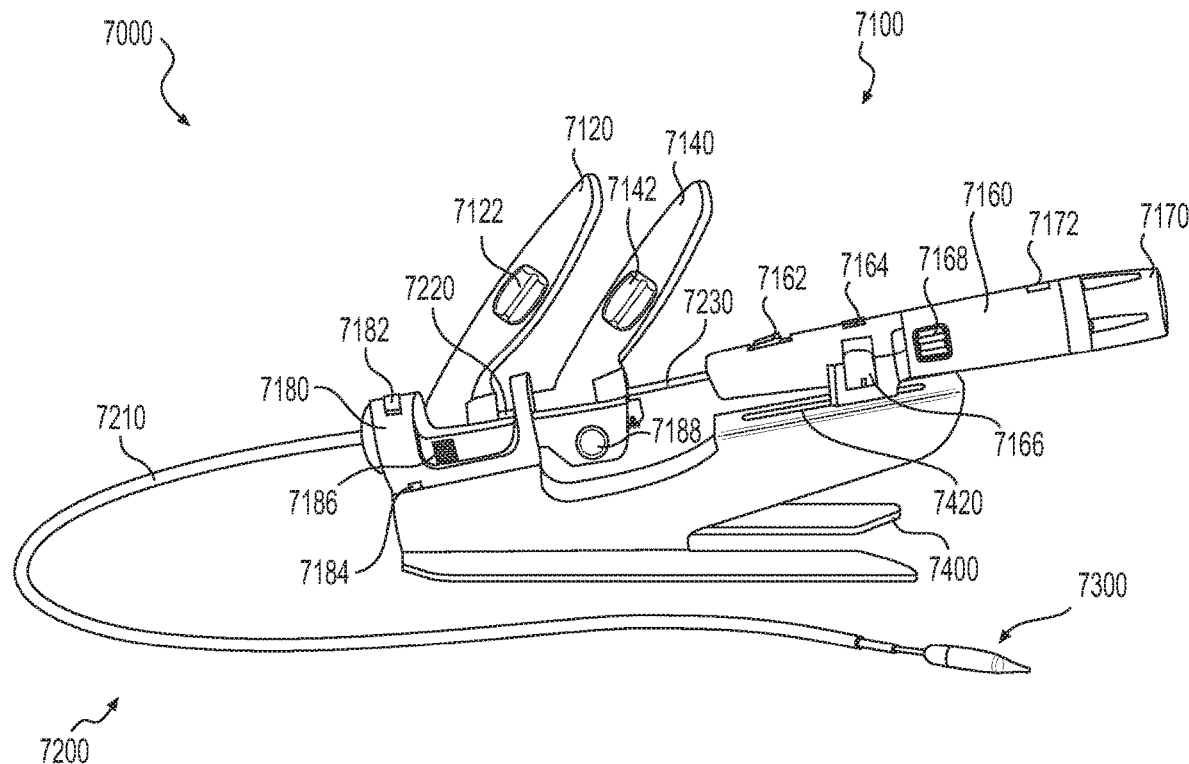
FIG. 7A illustrates an exemplary prosthetic valve delivery system, consistent with various embodiments of the present disclosure.

FIG. 7A illustrates a prosthetic valve delivery system 7000. Delivery system 7000 may be configured to deliver an implant prosthetic valve 6000 within a native valve, such as a native mitral valve. Prosthetic valve delivery system 7000 may include a control handle assembly 7100, a telescoping catheter assembly 7200, a delivery capsule 7300 configured to retain a prosthetic valve (e.g. valve 6000), and, optionally, a stand 7400.

Control handle assembly 7100 may include an outer sheath control handle 7120 having a steering knob 7122 configured to steer an outer sheath 7210 of the telescoping catheter assembly 7200. Control handle assembly 7100 may also include a guide catheter control handle 7140 having a steering knob 7142 configured to steer a guide catheter 7220 of the telescoping catheter assembly 7200.

Control handle assembly 7100 may also include an implant catheter control handle 7160 having a steering knob 7168 configured to steer an implant catheter 8100 of the telescoping catheter assembly 7200. Implant catheter control handle 7160 may also include a proximal capsule portion slider 7162, a distal capsule portion knob 7170, and a distal capsule portion knob lock 7172 configured to control release of the prosthetic valve 6000 from within delivery capsule 7300. Implant catheter control handle 7160 may also include a slide lock 7166 configured to lock the implant catheter control handle 7160 at a position within track 7420 of stand 7400.

Control handle assembly 7100 may also include a cradle 7180, which may be secured to stand 7400 via a locking mechanism that can be released by actuated of release button 7184. Cradle 7180 may include a rotation knob 7182 configured to control rotation of the outer sheath 7210 and guide catheter 7220. Cradle 7180 may also include a rotation knob 7186 configured to control rotation of the implant catheter 8100. Cradle 7180 may also include a knob 7188 configured to control relative axial movement between outer sheath control handle 7120 (which may be secured to outer sheath 7210) and guide catheter control handle 7140 (which may be secured to guide catheter 7220).

Figure 7B:
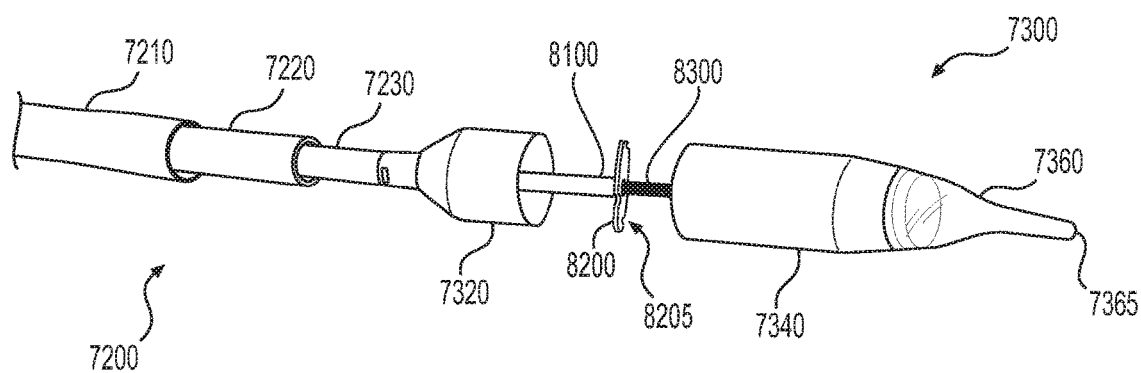
FIG. 7B illustrates an enlarged view of a delivery capsule of the exemplary prosthetic valve delivery system of FIG. 7A, consistent with various embodiments of the present disclosure.

FIG. 7B illustrates an enlarged view of delivery capsule 7300 of prosthetic valve delivery system 7000. Delivery capsule 7300 may include a proximal capsule portion 7320 and a distal capsule portion 7340 with a nose cone 7360 secured to the distal capsule portion 7340. A nose cone distal tip 7365 may form the distal end of the delivery capsule 7300. The telescoping catheter assembly 7200 may include a capsule shaft 7230 secured to, and configured to control movement of, the proximal capsule portion 7320 (e.g., due to connection 8400 between the capsule shaft 7230 and proximal capsule portion 7320, as illustrated in FIG. 8C). Implant catheter 8100 may extend within proximal capsule portion 7320 and may have a valve anchor disc 8200 connected to the distal end of the implant catheter 8100. A torque shaft 8300 may extend from the implant catheter 8100 and may be connected to distal capsule portion 7340; accordingly, torque shaft 8300 may be configured to control axial movement of the distal capsule portion 7340 relative to the implant catheter 8100 and valve anchor disc 8200. The proximal capsule portion 7320 and a distal capsule portion 7340 may be configured to retain prosthetic valve 6000, with the prosthetic valve 6000 secured against axial movement by valve anchor disc 8200. Control handle assembly 7100 may be configured to control movement of the proximal capsule portion 7320 and a distal capsule portion 7340, and thus may also control release of the prosthetic valve 6000 from within the delivery capsule 7300.

Figure 7D:
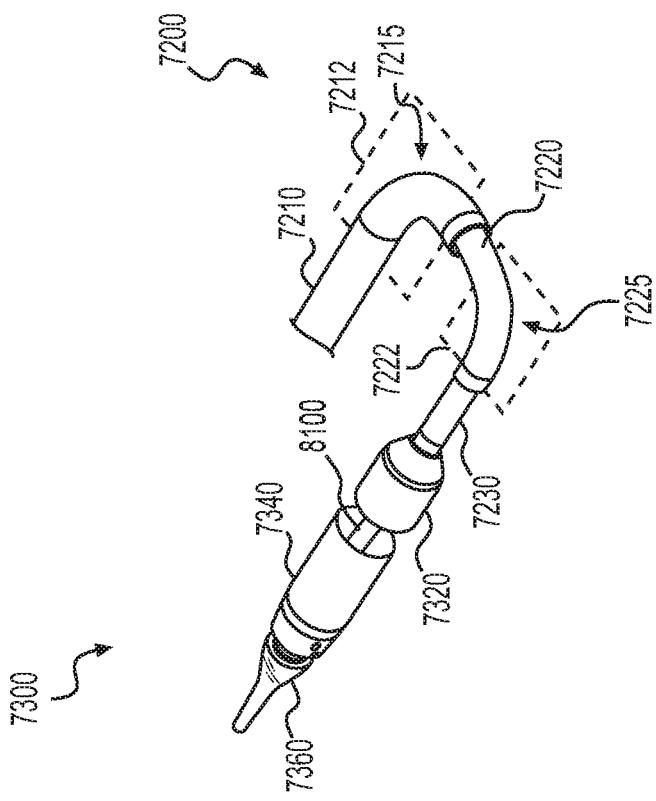
FIG. 7D illustrates another exemplary configuration of the telescoping catheter assembly and delivery capsule of FIG. 7C, consistent with various embodiments of the present disclosure.
Figure 7C:
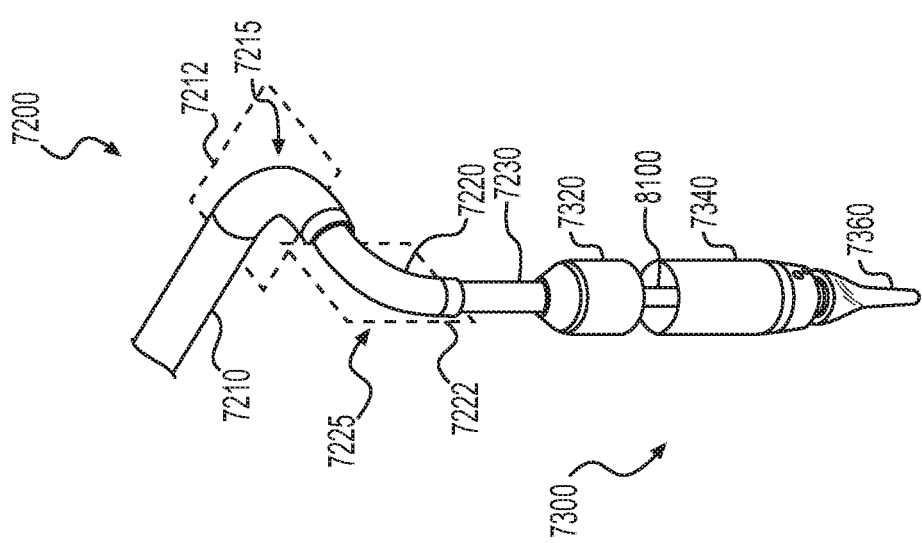
FIG. 7C illustrates an exemplary configuration of a telescoping catheter assembly and the delivery capsule of the exemplary prosthetic valve delivery system of FIG. 7A, consistent with various embodiments of the present disclosure.

FIGS. 7C and 7D illustrate exemplary configurations of the telescoping catheter assembly 7200. Outer sheath 7210 and guide catheter 7220 may include respective bending portions 7215 and 7225, at which the outer sheath 7210 and guide catheter 7220 may be configured to bend within their respective steering planes 7212 and 7222. In some embodiments, bending of the outer sheath 7210 within the first steering plane 7212 may be controlled by the outer sheath steering knob 7122 of the control handle assembly 7100. Additionally, or alternatively, bending of the guide catheter 7220 within the second steering plane 7222 may be controlled by the guide catheter steering knob 7142 of the control handle assembly 7100. In some embodiments, under control of the control handle assembly 7100, the outer sheath 7210, guide catheter 7220, and implant catheter 8100 may be steered so as to correctly position the delivery capsule 7300 within a native valve for implantation of the prosthetic valve.

Figure 8A:
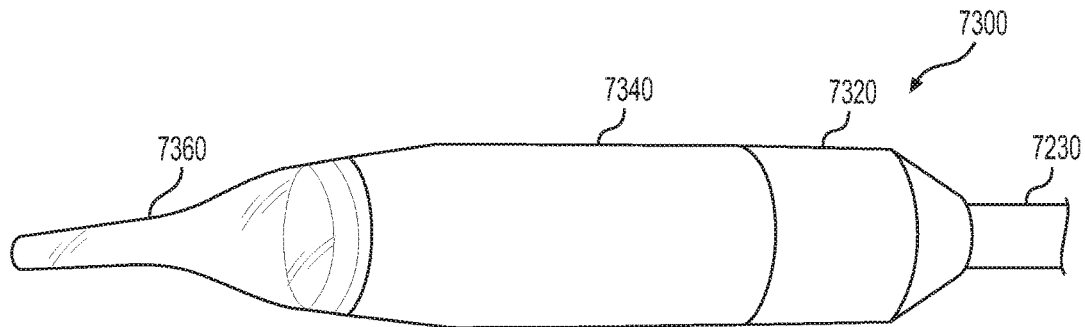
FIG. 8A illustrates another enlarged view of the exemplary delivery capsule of the prosthetic valve delivery system of FIG. 7A in a closed configuration, consistent with various embodiments of the present disclosure.
Figure 8B:
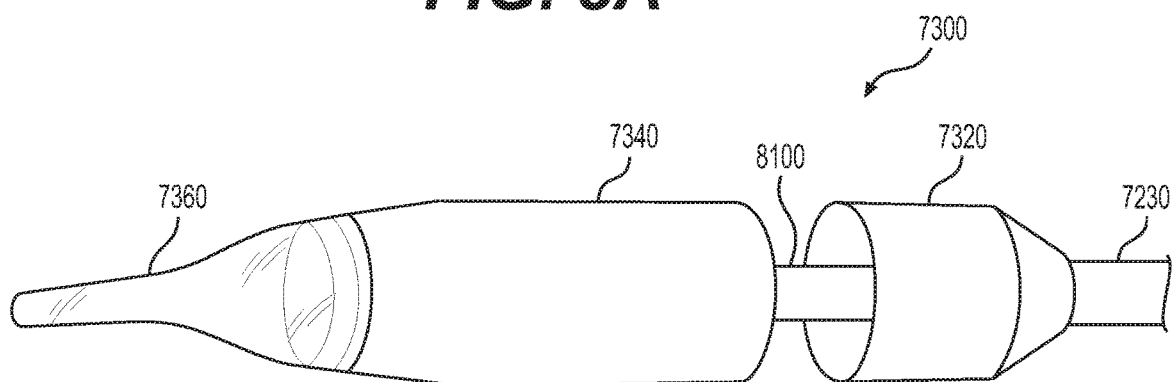
FIG. 8B illustrates the exemplary delivery capsule of FIG. 8A in an open configuration, consistent with various embodiments of the present disclosure.
Figure 8C:
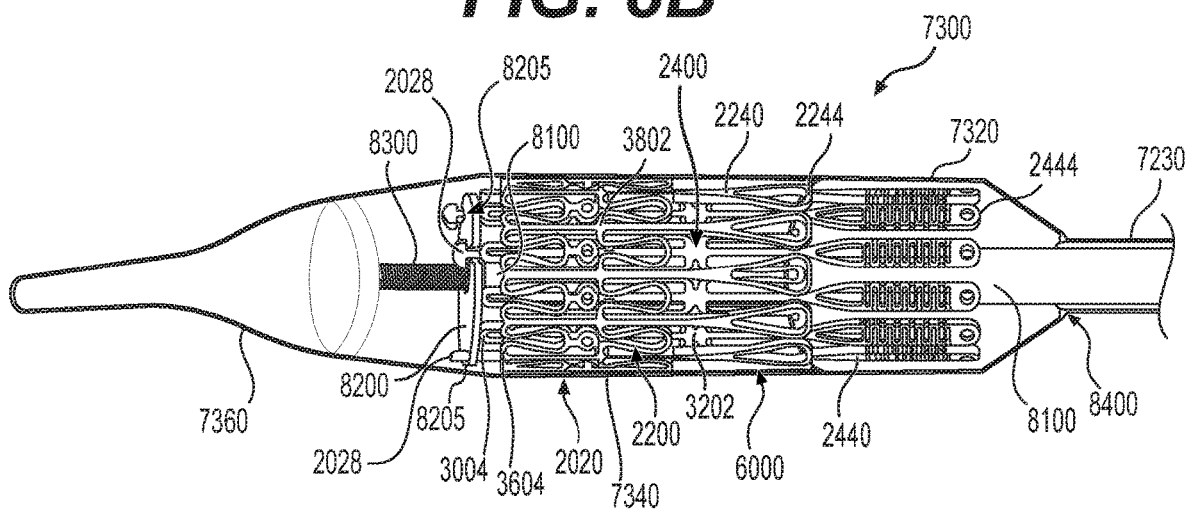
FIG. 8C illustrates an interior view of the exemplary delivery capsule of FIG. 8A in the closed configuration, consistent with various embodiments of the present disclosure.

FIG. 8A illustrates an enlarged view of delivery capsule 7300 in a closed configuration, while FIG. 8B illustrates an enlarged view of delivery capsule 7300 in an open configuration. In the closed configuration of FIG. 8A, the distal capsule portion 7340 and proximal capsule portion 7320 may be brought together to form an enclosed compartment in which prosthetic valve 6000 may be retained. In the open configuration of FIG. 8B, the distal capsule portion 7340 and proximal capsule portion 7320 may be drawn apart. In some embodiments, the delivery capsule 7300 may be configured such that the distal capsule portion 7340 and proximal capsule portion 7320 are moved apart from each other, the prosthetic valve 6000 may be sequentially deployed from within the delivery capsule and implanted within a native valve.

FIG. 8C illustrates an interior view of delivery capsule 7300 with prosthetic valve 6000 retained within the delivery capsule. Although only the valve frame 2000 of the prosthetic valve 6000 is illustrated in FIG. 8C, one of ordinary skill will understand that the entire prosthetic valve 6000 depicted in FIGS. 6A-6E may be retained within delivery capsule 7300 in the configuration illustrated in FIG. 8C.

In the embodiment illustrated in FIG. 8C, at least a portion of the annular valve body 2020 and ventricular anchoring legs 2240 of the prosthetic valve 6000 may be retained within the distal capsule portion. Additionally, or alternatively, at least a portion of atrial anchoring arms 2440 may be retained within proximal capsule portion 7320. In some embodiments, valve anchor disc 8200 may include a number of recesses 8205 configured to receive and retain the ventricular end delivery posts 2028 of the prosthetic valve 6000. For example, the valve anchor disc 8200 may include at least the same number of recesses 8205 as there are delivery posts 2028 of the prosthetic valve 6000. In some embodiments, the delivery posts 2028 may be retained within the recesses 8205 so long as the annular valve body 2020 remains in a radially-contracted configuration; the engagement between the valve anchor disc 8200 and delivery posts 2028 may secure the prosthetic valve 6000 against axial movement. Upon radial expansion of the annular valve body 2020, the delivery posts 2028 may slide or expand out of the recesses 8205, freeing the prosthetic valve 6000 from engagement with the valve anchor disc 8200.

Figure 9:
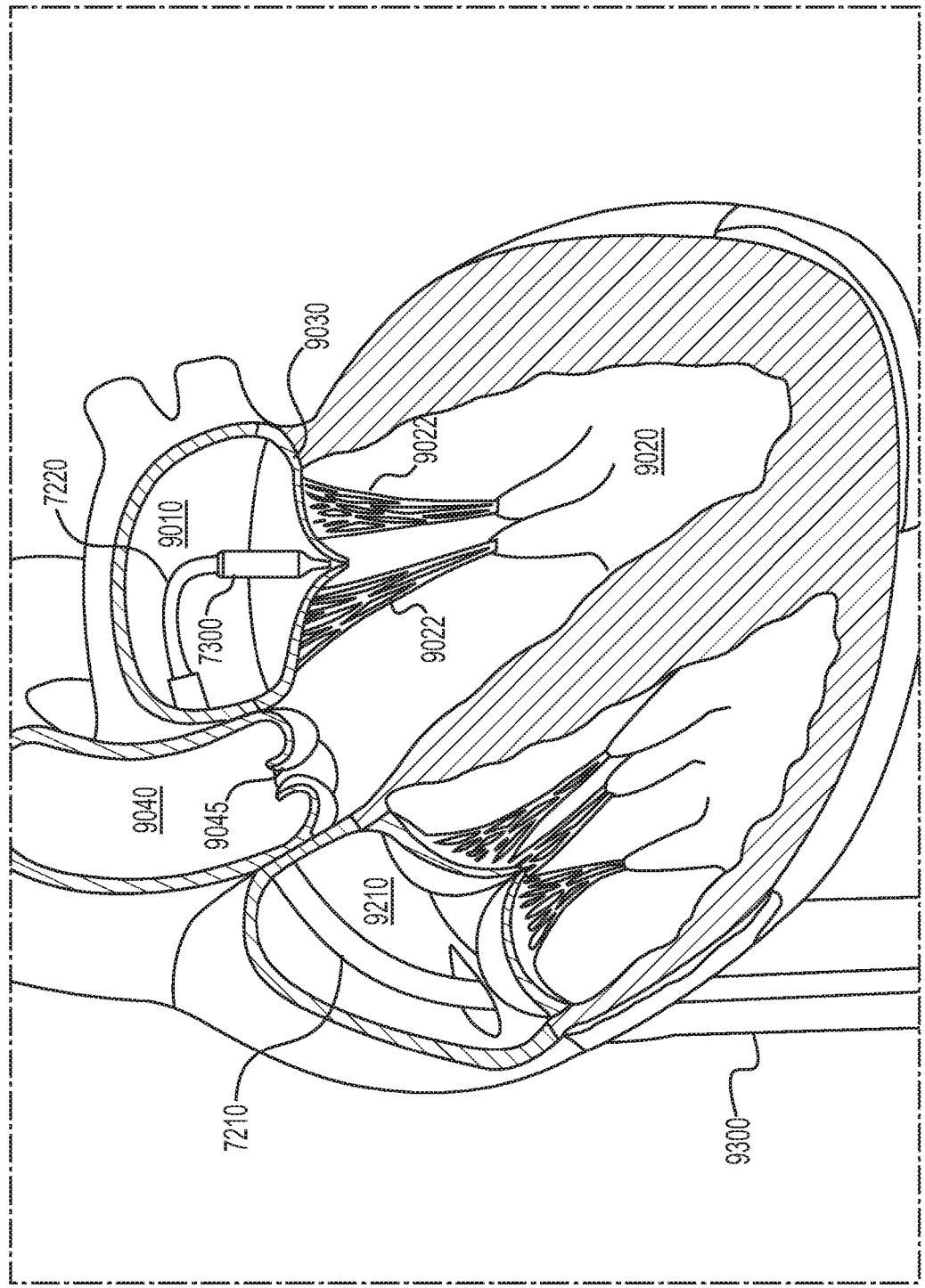
FIG. 9 illustrates advancement of the exemplary prosthetic valve delivery system of FIG. 7A into the left atrium, consistent with various embodiments of the present disclosure.

FIG. 9 illustrates one exemplary advancement route of the delivery capsule 7300 to the left atrium. In the example illustrated in FIG. 9, the delivery capsule 7300 may be steered through the vena cava into the right atrium 9210 and may pierce the interatrial septum and enter the left atrium 9010. Alternatively, the delivery capsule may be delivered to the heart by other routes. FIG. 9 also depicts the left ventricle 9020, the mitral valve 9030, the chordae tendineae 9022, the aortic valve 9045, and the aorta 9040.

Figure 10B:
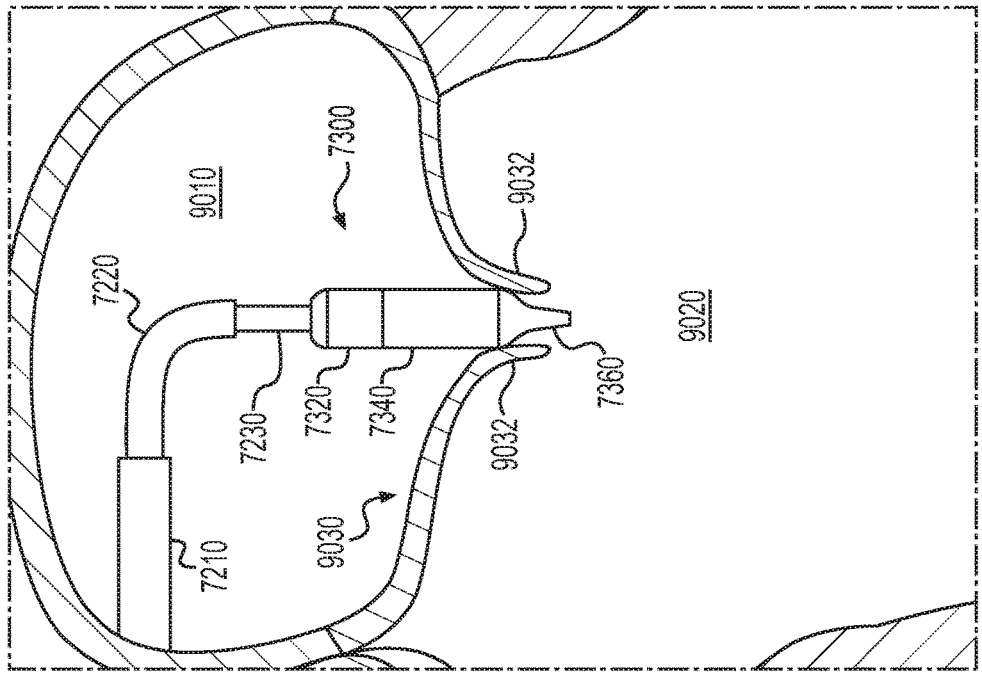
FIGS. 10A-10H depict implantation of the prosthetic valve of FIGS. 6A-6E within a native mitral valve by the exemplary prosthetic valve delivery system of FIG. 7A, consistent with various embodiments of the present disclosure.
Figure 10A:
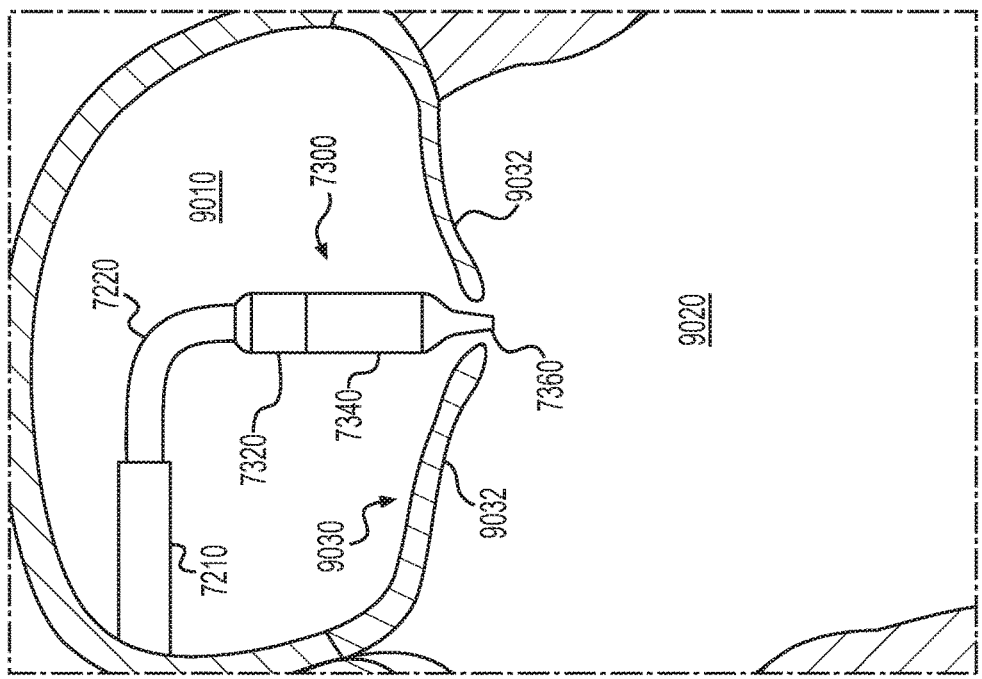
Figure 10D:
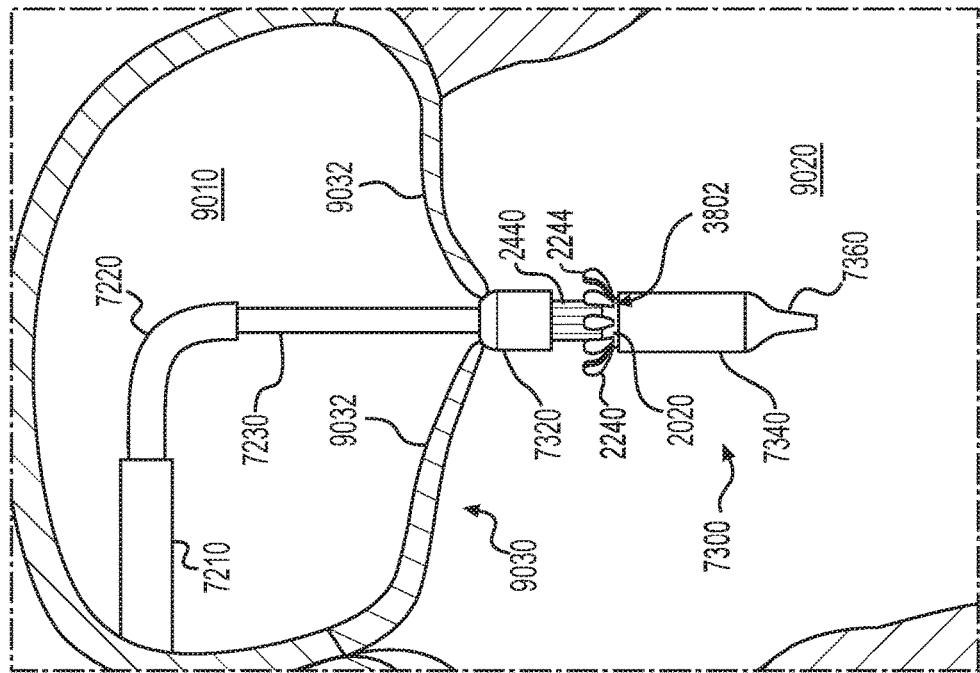
Figure 10C:
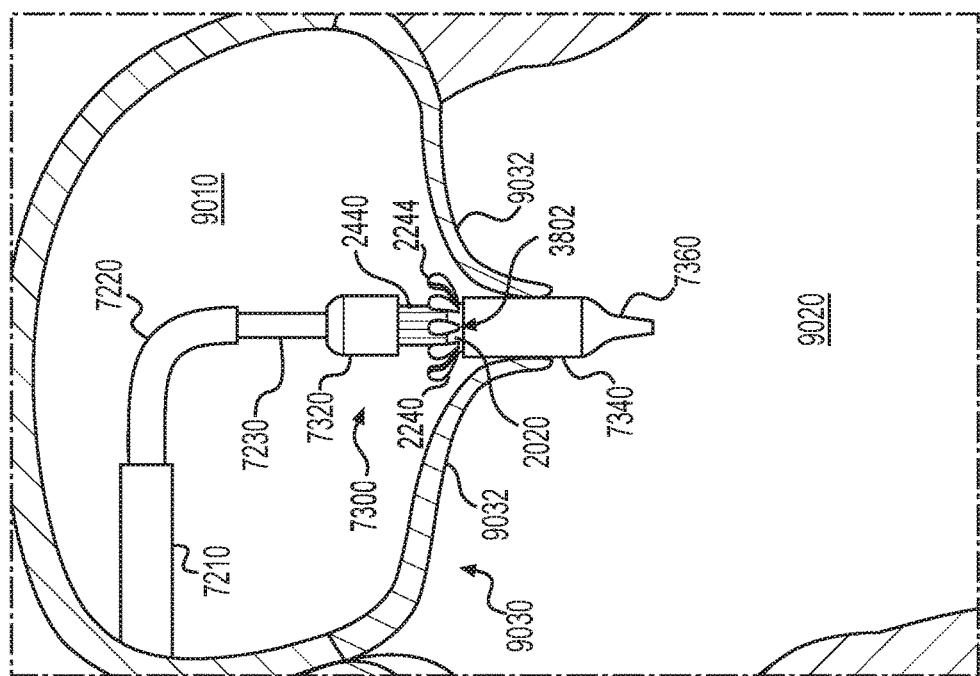

FIGS. 10A-10H depict an exemplary implantation method of prosthetic valve 6000 within a mitral valve 9030. In FIG. 10A, the delivery capsule 7300 may be coaxially aligned with the mitral valve 9030. In some embodiments, the prosthetic valve 6000 may be held within the delivery capsule 7300 while the prosthetic valve is arranged in the configuration of FIG. 5A. In FIG. 10B, the delivery capsule 7300 may be distally advanced into the mitral valve 9030. In FIG. 10C, the distal capsule portion 7340 may be distally advanced relative to the rest of the delivery capsule 7300. This may release the ventricular anchoring legs 2240 from the distal capsule portion 7340, while the atrial anchoring arms 2440 and annular valve body 2020 remain constrained within the delivery capsule. In the example shown in FIG. 10C, the ventricular anchoring legs 2240 may be released from the delivery capsule 7300 within the atrium 9010. In some embodiments, the prosthetic valve 6000 may assume the configuration of FIG. 5B when the ventricular anchoring legs 2240 are released in the step depicted in FIG. 10C.

Figure 10F:
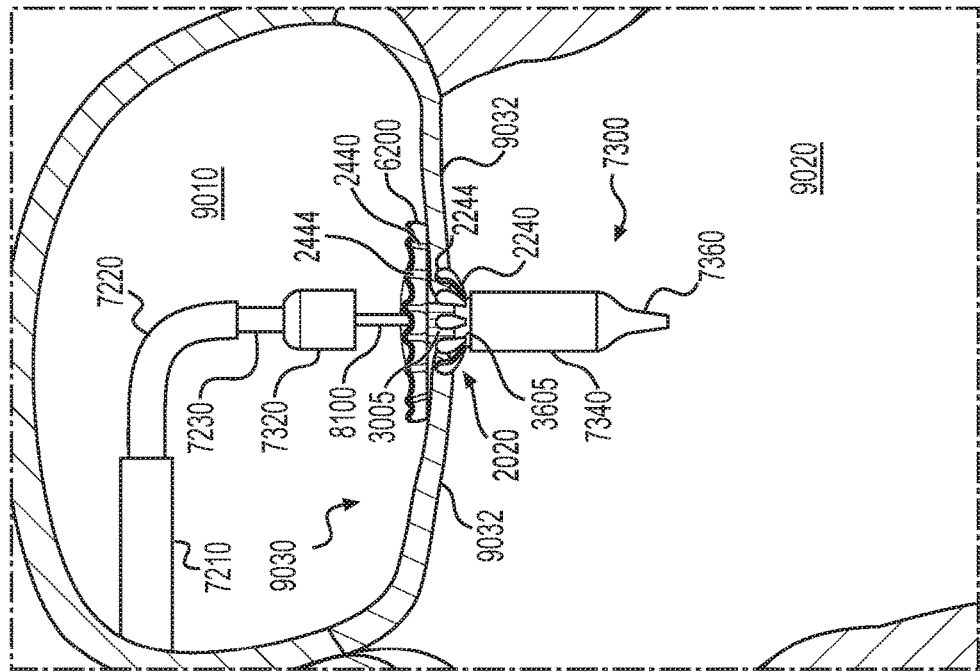
Figure 10E:
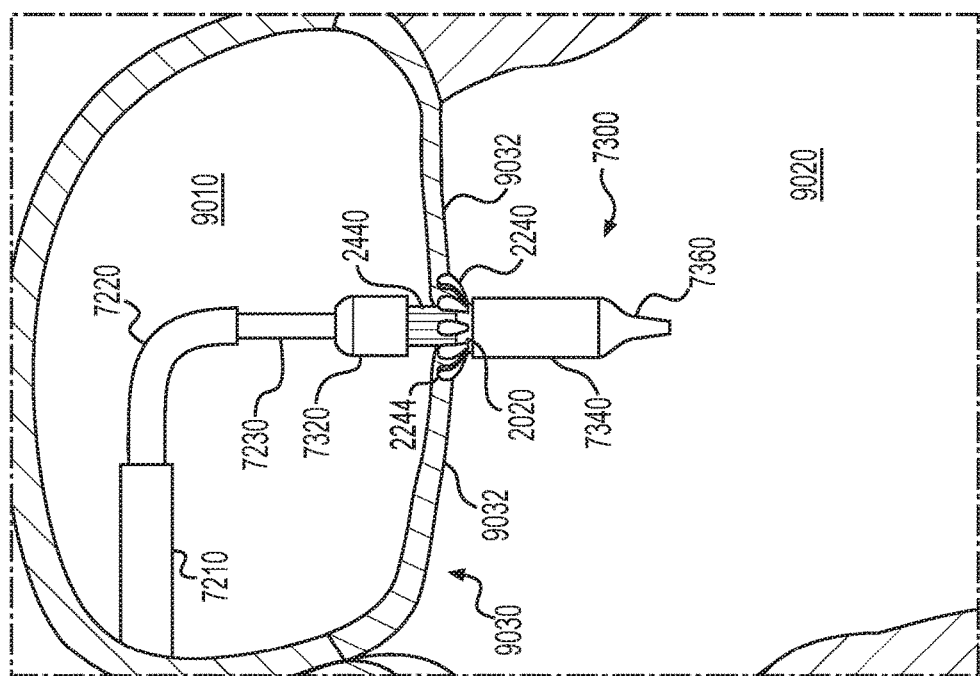

In FIG. 10D, the released ventricular anchoring legs 2240 may be passed through the mitral valve 9030 and into the left ventricle 9020. In FIG. 10E, the released legs 2240 may be proximally retracted until the ventricular anchoring legs come into contact with the ventricular tissue of the mitral valve 9030. In FIG. 10F, the proximal capsule portion 7320 may be retracted proximally, thus releasing the atrial anchoring arms 2440 within atrium 9010 while the annular valve body 2020 remains radially constrained within the distal capsule portion 7340. In some embodiments, the prosthetic valve 6000 may assume the configuration of FIG. 5D when the atrial anchoring arms 2440 are released in the step of FIG. 10F.

Figure 10H:
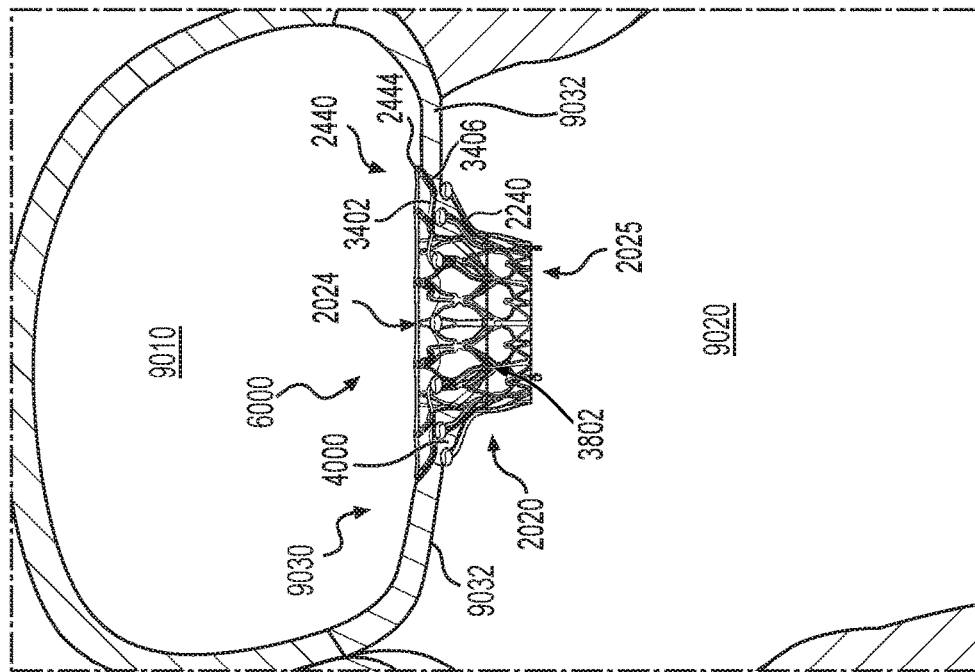
Figure 10G:
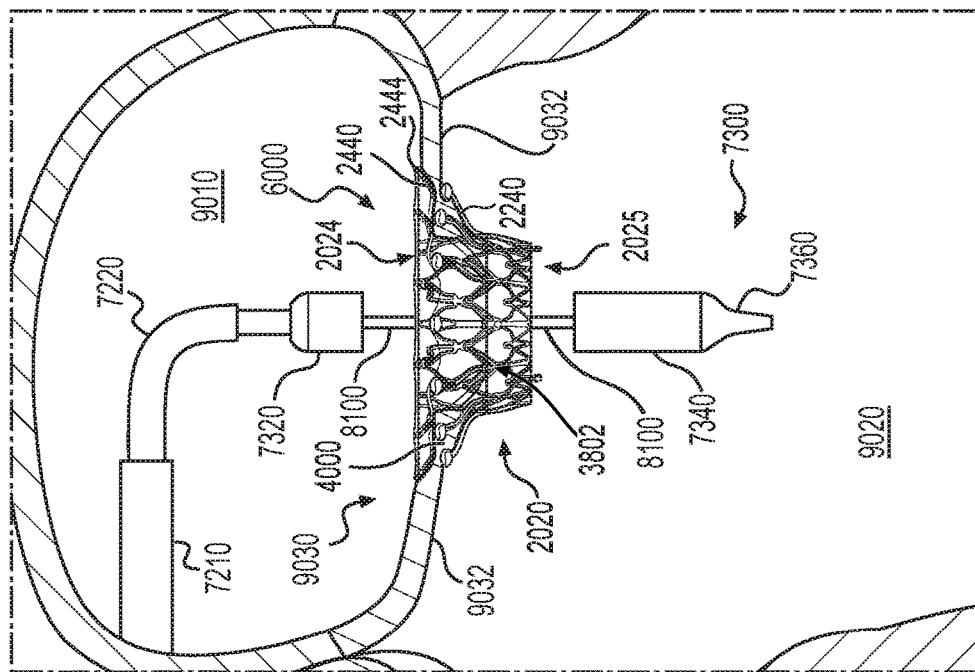

In FIG. 10G, the distal capsule portion 7340 may be advanced further until the annular valve body 2020 is released from the capsule and allowed to radially expand. Radial expansion of the annular valve body 2020 may allow the prosthetic valve to assume the fully-expanded configuration illustrated in FIG. 5E. At this stage, prosthetic valve 6000 may be securely implanted within mitral valve 9030. In FIG. 10H, the delivery system 7000, including capsule 7300, may be removed.

Various embodiments of the present disclosure relate to prosthetic valve delivery systems. While the present disclosure provides examples of prosthetic heart valve delivery systems, it should be noted that aspects of the disclosure in their broadest sense, are not limited to prosthetic heart valve delivery systems. Rather, it is contemplated that aspects of the present disclosure may be applied to delivery systems for other prosthetic or implantable devices as well and are not limited to delivery systems for prosthetic valves or heart valves. Prosthetic valve delivery system 7000 illustrated in FIG. 7A is one example of a prosthetic valve delivery system in accordance with this disclosure.

An exemplary prosthetic valve delivery system in accordance with the present disclosure may include one or more catheters configured to approach the heart transfemorally, transapically, transatrially, transseptally, or transjugularly. The one or more catheters may be configured to position the prosthetic valve, which may be retained within the delivery system, in or near the native valve orifice such that the prosthetic valve may be released from the delivery system within or near the native valve. As used herein, the term "catheter" may denote an elongated, tubular structure that may be selectively flexible along a length of the elongated structure. The one or more catheters can be manufactured from a variety of suitable, biocompatible materials, some non-limiting examples including silicone Pebax, rubber, nylon, polyurethane, polyethylene terephthalate (PET), latex, thermoplastic elastomers, silicone, and polyimides. The one or more catheters may be sufficiently flexible such that they may be configured to pass through tortuous anatomy (e.g., blood vessels and heart chambers) without sustaining damage or injuring the native tissue during delivery of the catheter to the implantation site. The one or more catheters of the exemplary prosthetic valve delivery system may be at least long enough to extend from a location outside of a patient's body to a site within the heart. The one or more catheters may be configured as a one-size-fits all, a range of sizes depending on the size of the patient or may be fully customizable. Exemplary sizes of the one or more catheters may include between 6 French (Fr) and 40 Fr, between 20 Fr and 35 Fr, between 27 Fr and 33 Fr. The one or more catheters may have any appropriate length, for example between 1 millimeter (mm) and 1 meter (m), between 1 mm and 2 m, between 1 mm and 3 m, or longer, such the one or more catheters are at least long enough to extend from a location outside of the patient's body to a site within the heart.

In some embodiments, the one or more catheters of the exemplary prosthetic valve delivery system may include a first catheter. In some embodiments, the first catheter may be the outer-most catheter of the delivery system. Alternatively, the first catheter may be received within another catheter or tubular structure. Outer sheath 7210 illustrated in FIG. 7B is one example of a first catheter of delivery system 7000, in accordance with this disclosure. Outer sheath 7210 may form a portion of telescoping catheter assembly 7200 of delivery system 7000. As illustrated in FIG. 7A, telescoping catheter assembly 7200 may extend between control handle assembly 7100 and capsule 7300 and may include a plurality of telescoping catheters (including outer sheath 7210).

An exemplary prosthetic valve delivery system may include a first steering mechanism configured to bend the first catheter within a first steering plane. As used herein, the term "bend" may refer to the shaping or forcing the first catheter from a straight configuration into a curved or angled configuration, or from a curved or angled configuration back to a straight configuration or into a different curved or angled configuration. In some embodiments, the first steering mechanism may be actuated by a user to effect bending of the first catheter within the first steering plane. For example, the first steering mechanism may be incorporated within a control handle assembly (e.g., control handle assembly 7100 depicted in FIG. 7A), which may be operated by a user to control different components of the prosthetic valve delivery system. The first steering mechanism may include any appropriate steering mechanism, examples of which include, but are not limited to, a rotatable knob, a wheel, a handle, a joystick, a touchpad, and combinations thereof, among other steering mechanisms capable of effecting bending of the first catheter within the first steering plane.

In some embodiments, the first catheter may include at least one portion configured to bend relative to the rest of the first catheter within the first steering plane, under the control of the first steering mechanism. Bending portion 7215 illustrated in FIGS. 7C and 7D is one example of a bending portion of an exemplary first catheter, in accordance with the present disclosure. In some embodiments, the bending portion of the first catheter may be configured to bend in a single direction from the straight configuration thereof (e.g., from a straight configuration of the bending portion towards a left-hand side, but not towards a right-hand side; referred to hereafter as "unidirectional bending"). In other embodiments, the bending portion of the first catheter may be configured to bend in two opposite directions from the straight configuration thereof (e.g., both to the left-hand side and the right-hand side from the straight configuration; referred to hereafter as "bidirectional bending"). For example, a bending control device, such as one or more pull wires, may extend between the first steering mechanism and the bending portion of the first catheter, such that the first steering mechanism may be configured to control bending of the first catheter within the first steering plane. In some further embodiments, the first catheter may include two or more bending portions, each of which may be configured for unidirectional bending or bidirectional bending. The first steering mechanism may be configured to control bending of the two or more bending portions of the first catheter within the first steering plane. In some yet further embodiments, the first steering mechanism may be configured to bend the entire length of the first catheter within the first steering plane. For example, outer sheath steering knob 7122 depicted in FIG. 7A may be configured to bend outer sheath 7210 (i.e. the exemplary first catheter) within a first steering plane. For example, one or more pull wires may extend between knob 7122 and first bending portion 7215, such that knob 7122 may control the bending of outer sheath 7210 within first steering plane 7212. Accordingly, outer sheath steering knob 7122 may be considered a first steering mechanism of delivery system 7000 in some embodiments.

As discussed above, an exemplary prosthetic valve delivery system in accordance with the present disclosure may include one or more catheters. In some embodiments, the prosthetic valve delivery system may include a second catheter coaxially arranged within the first catheter. The second catheter may be situated at least partially within the first catheter and may be configured for axial movement relative to the first catheter. In some embodiments, the second catheter may be the inner-most catheter of the prosthetic valve delivery system. Alternatively, one or more tubular structures may be situated at least partially within the second catheter. FIG. 7B, for example, illustrates exemplary prosthetic valve delivery system 7000, which may include a guide catheter 7220 coaxially arranged within the outer sheath 7210 (i.e. the exemplary first catheter), as part of the telescoping catheter assembly 7200. Accordingly, guide catheter 7220 may constitute a second catheter of prosthetic valve delivery system 7000.

An exemplary prosthetic valve delivery system may include a second steering mechanism configured to bend the second catheter within a second steering plane different from the first steering plane. In some embodiments, the second steering mechanism may be actuated by a user to effect bending of the second catheter within the second steering plane. For example, the second steering mechanism may be incorporated within a control handle assembly (e.g., control handle assembly 7100 depicted in FIG. 7A), which may be operated by a user to control different components of the prosthetic valve delivery system. The second steering mechanism may include any appropriate steering mechanism, examples of which include, but are not limited to, a rotatable knob, a wheel, a handle, a joystick, a touchpad, and combinations thereof, among other steering mechanisms capable of effecting bending of the second catheter within the second steering plane.

In some embodiments, the second catheter may include at least one portion configured to bend relative to the rest of the second catheter within the second steering plane, under the control of the second steering mechanism. Bending portion 7225 illustrated in FIGS. 7C and 7D is one example of a bending portion of an exemplary second catheter, in accordance with the present disclosure. In some embodiments, the bending portion of the second catheter may be configured for unidirectional bending and/or for bidirectional bending. For example, a bending control device, such as one or more pull wires, may extend between the second steering mechanism and the bending portion of the second catheter, such that the second steering mechanism may be configured to control bending of the second catheter within the second steering plane. In some further embodiments, the second catheter may include two or more bending portions, each of which may be configured for unidirectional bending or bidirectional bending. The second steering mechanism may be configured to control bending of the two or more bending portions of the second catheter within the second steering plane. In some yet further embodiments, the second steering mechanism may be configured to bend the entire length of the second catheter within the second steering plane. For example, guide catheter steering knob 7142 depicted in FIG. 7A may be configured to bend guide catheter 7220 (i.e. the second catheter of delivery system 7000) within a second steering plane. For example, one or more pull wires may extend between knob 7142 and second bending portion 7225, such that knob 7142 may control the bending of guide catheter 7220 within second steering plane 7222. Accordingly, guide catheter steering knob 7142 may be considered a second steering mechanism of delivery system 7000 in some embodiments.

In some embodiments, an exemplary prosthetic valve delivery system may include a capsule positioned distal to both the first catheter and the second catheter. A proximal end of the prosthetic valve delivery system may refer to a point or a location along the length of the delivery system closer to a physician or a medical practitioner. A distal end of the prosthetic valve delivery system may refer to a point or a location along the length of the delivery system closer to an implantation or treatment site in the body of a patient during implantation of a prosthetic valve. The capsule may be a hollow structure, such as a vessel, container, receptacle, or the like, which can be configured to hold the prosthetic valve at least partially therein. The capsule may have multiple parts configured to move relative to each other so as to selectively retain and release the valve. In some embodiments, the capsule may be positioned distal to the distal ends of the first and second catheters. The capsule may be configured to retain a prosthetic valve therein and to deliver the prosthetic valve through the anatomy (e.g., vasculature) to the prosthetic valve implantation site. That is, the capsule may be configured to retain the prosthetic valve therein during transvascular advancement of the capsule. In some embodiments, the capsule may be configured to retain the prosthetic valve in a radially-contracted configuration, such that the prosthetic valve may easily pass through the anatomy during delivery to the implantation site. In the example depicted in FIG. 7B, an exemplary capsule 7300 may be positioned distal to the outer sheath 7210 (i.e., the exemplary first catheter) and the guide catheter 7220 (i.e., the exemplary second catheter). Capsule 7300 may include multiple capsule portions, including proximal capsule portion 7320, distal capsule portion 7340, and a nose cone 7360. As illustrated in FIG. 8C, an exemplary valve prosthesis 6000 may be held in a radially-contracted configuration within exemplary capsule 7300. For the sake of illustration, only heart valve frame 2000 of FIG. 2A is illustrated in FIG. 8C; however, one of ordinary skill will understand that the entirety of prosthetic valve 6000 may be held within capsule 7300 in the manner illustrated in FIG. 8C. The exemplary capsule 7300 is further illustrated in FIGS. 7C and 7D positioned at the distal end of the outer sheath 7210 and the guide catheter 7220.

In some exemplary prosthetic valve delivery systems, the first and second catheters may be configured such that the first steering plane may be orthogonal to the second steering plane. "Orthogonal" may mean of or involving right angles. Accordingly, the first steering plane and the second steering plane can be positioned at right angles with respect to each other. Additionally, or alternatively, the first steering plane and the second steering plane can be positioned at acute angles with respect to each other (e.g., angles less than 90°). For example, in some embodiments, the first steering plane may be configured to be positioned at an angle of between 30° and 89°, relative to the second steering plane. Furthermore, the first steering plane and the second steering plane can be positioned at obtuse angles with respect to each other (e.g., angles greater than 90°. FIG. 7C shows an exemplary embodiment where first steering plane 7212 may be positioned orthogonal to second steering plane 7222. In some embodiments, the first and second catheters may be maneuverable such that the first and second steering planes may be the same plane or parallel planes. For example, in FIG. 7D, outer sheath 7210 (i.e. the exemplary first catheter) and guide catheter 7220 (i.e., the exemplary second catheter) may be arranged such that first steering plane 7212 and second steering plane 7222 are the same plane. In some embodiments, the first and second catheters may be configured such that the angle between the first and second steering planes may be controllably varied (e.g., between 30° and 90°), such as by a rotation mechanism configured to rotate the second catheter relative to the first catheter, such as a rotatable knob, a wheel, a handle, a joystick, a touchpad, or any other suitable rotation mechanism. Additionally, or alternatively, the first and second catheters may be manually rotated to achieve the desired angle between the first and second steering planes.

In some exemplary embodiments, the first catheter may be configured to remain substantially straightened while the second catheter bends within the second steering plane. In some embodiments, the bending portion of the second catheter can extend beyond the distal end of the first catheter, where bending of the bending portion of the second catheter does not cause bending of the bending portion of the first catheter. The phrase "substantially straightened" may refer to a configuration of the first catheter in which the entire length of the first catheter, including bending portion(s) thereof, may be straight and unbent. In some embodiments, the bending portion of the second catheter can remain substantially straightened while the bending portion of the first catheter is bent. For example, bending portion 7225 of the guide catheter 7220 (i.e., the exemplary second catheter) may be positioned distal to or outside of the outer sheath 7210 (i.e. the exemplary first catheter).

As described above, the first and second catheters may be flexible, and the first and second steering mechanisms may be configured to selectively bend the first and second catheters respectively at a range of angles as desired. In some exemplary embodiments, the first catheter and the second catheter may each be configured to bend (e.g., within the first and second steering planes) out of the straight configurations thereof by an angle greater than 90°. In some exemplary embodiments, the first catheter and the second catheter may each be configured to bend (e.g., within the first and second steering planes) out of the straight configurations thereof by an angle no greater than 120° (that is, an angle equal to or less than 120°). In some embodiments, one or more of the first catheter and second catheter may be configured for unidirectional bending out of the straight configurations thereof. Additionally, or alternatively, one or more of the first catheter and second catheter may be configured for bidirectional bending out of the straight configurations thereof.

In some embodiments, an exemplary prosthetic valve delivery system may include a third catheter coaxially arranged within the second catheter. The third catheter may be situated at least partially within the second catheter and may be configured for axial movement relative to the first catheter and the second catheter. In some embodiments, the third catheter may be the inner-most catheter of the prosthetic valve delivery system. For example, one or more tubular structures may be situated between the second catheter and the third catheter. Alternatively, one or more tubular structures may be situated at least partially within the third catheter. FIG. 7B, for example, illustrates a portion of an exemplary prosthetic valve delivery system 7000, which may include an implant catheter 8100 coaxially arranged within the guide catheter 7220 (i.e., the exemplary second catheter), as part of the telescoping catheter assembly 7200. Accordingly, implant catheter 8100 may constitute a third catheter of prosthetic valve delivery system 7000.

In some embodiments, the third catheter may include a third steering mechanism configured to bend the third catheter within a third steering plane, different from the first and second steering planes. In some embodiments, the third steering mechanism may be actuated by a user to effect bending of the third catheter within the third steering plane. For example, in FIG. 7A, implant catheter steering knob 7168 may be configured to control bending of the implant catheter 8100 (i.e., the exemplary third catheter), and may thus be considered a third steering mechanism in some embodiments. The third steering mechanism may include any appropriate steering mechanism, examples of which include, but are not limited to a rotatable knob, a wheel, a joystick, a touchpad, and combinations thereof, among other steering mechanisms capable of effecting bending of the third catheter within the third steering plane. In some embodiments, a bending control device, such as one or more pull wires, may extend between the third steering mechanism and the bending portion(s) of the third catheter, such that the third steering mechanism may be configured to control bending of the third catheter within the third steering plane. Additionally, or alternatively, the third catheter may include a rotation mechanism configured to rotate the third catheter about the longitudinal axis of the third catheter. In some embodiments, the third catheter may be rotated independently of the first catheter and second catheter. For example, in FIG. 7A, the control handle assembly 7100 may include a rotation knob 7186 configured to rotate implant catheter 8100 (i.e., the exemplary third catheter) about the longitudinal axis of the implant catheter. In some embodiments, implant catheter 8100 may be secured against rotation actuated by rotation knob 7182, which may be configured to rotate the outer sheath 7210 (i.e., the exemplary first catheter) and the guide catheter 7220 (i.e., the exemplary second catheter).

In some embodiments of the prosthetic valve delivery system, at least a portion of the capsule may be configured for longitudinal movement relative to the first catheter, second catheter, and third catheter. The term "longitudinal movement" may refer to axial translation of the portion of the capsule relative to the first, second, and third catheters and may constitute movement away from and/or towards the first, second, and third catheters. For example, the prosthetic valve delivery system may include a capsule shaft, which may be connected to a proximal capsule portion of the delivery capsule and configured for axial movement relative to the first, second, and third catheters. Accordingly, the proximal capsule portion may be configured for axial movement relative to the first, second, and third catheters via movement of the capsule shaft relative to the first, second, and third catheters. In some embodiments, the capsule shaft may be included within the telescoping catheter assembly and may be situated within the second catheter. Additionally, or alternatively, the third catheter may, in turn, be situated within the capsule shaft. For example, as illustrated in FIG. 7B, exemplary delivery system 7000 may include capsule shaft 7230, which may be connected (e.g. at connection 8400 shown in FIG. 8C) to the proximal capsule portion 7320. The connection between the capsule shaft and the proximal capsule portion can be any mechanical or electromechanical connection mechanisms such as a weld, an adhesive, an interference fit, threads, barbs, clamp(s), overmolding, magnetic connection, and other suitable mechanical or electromechanical connection mechanisms.

In an exemplary prosthetic valve delivery system, the first catheter, the second catheter, and the third catheter may all be configured for relative longitudinal movement. Accordingly, each catheter may be configured to move independently in a proximal and/or distal direction, regardless of the movement or stationary nature of the other catheters, which may allow for independent control of the longitudinal position of each catheter. For example, the second catheter may be configured to move longitudinally while the first and third catheter remain in their respective longitudinal position with respect to the second catheter. That is, the second catheter may translate proximally or distally while the first catheter and the third catheter remain in their respective longitudinal positions. For example, FIGS. 10F and 10G illustrate an exemplary embodiment in which the outer sheath 7210 (i.e. the exemplary first catheter), the guide catheter 7220 (i.e., the exemplary second catheter), and the implant catheter 8100 (i.e., the exemplary third catheter) are positioned at longitudinal positions with respect to one another, in which implant catheter 8100 moves distally while the outer sheath 7210 and the guide catheter 7220 remain stationary.

As described above, the first steering mechanism and the second steering mechanism can be configured to cause the first catheter and second catheter, respectively, to bend. In some embodiments, the first and second steering mechanisms may be configured to actuate bending of the first and second catheters, respectively, within desired first and second steering planes to allow correct placement of the prosthetic valve at the implantation site. FIGS. 10A-10G illustrate an example in which outer sheath 7210 (i.e., the exemplary first catheter) and guide catheter 7220 (i.e., the exemplary second catheter) each bend at a specific point as actuated by the first and second steering mechanisms, respectively. In some embodiments, if the delivery capsule 7300 is angled away from the mitral valve, the outer sheath 7210 and guide catheter 7220 may be rotated (e.g., by actuation of rotation knob 7182) to angle the delivery capsule towards the mitral valve. Due to bending of the first and second catheters by the first and second steering mechanisms, respectively, and well as rotation of the first and second catheters (if needed), capsule 7300 may be aligned with mitral valve 9030, and the capsule shaft 7230 and implant catheter 8100 (i.e., the exemplary third catheter) may move capsule 7300 through the mitral valve 9030 until the nose cone 7360 is within the ventricle 9020, which may provide correct placement of the prosthetic valve at the implantation site. In some embodiments the first catheter may have the prosthetic valve and one or more catheters nested therein, including the second catheter and the third catheter, and may be advanced by a desired route into the heart of the patient. For example, as depicted in FIG. 9, the first catheter may be advanced via a transfemoral route through the vena cava 9300 into the right atrium 9210, may cross the fossa ovalis, and may enter the left atrium (e.g., atrium 9010) of the patient's heart.

In some embodiments, the first catheter and features nested therein (including the second catheter and third catheter) may be delivered to the heart and into the left atrium over a guide wire. For example, once the distal end of the outer sheath 7210 (i.e. the exemplary first catheter) is situated within the left atrium 9010, the first steering mechanism 7122 may be actuated to bend the outer sheath 7210 within the first steering plane 7212 until the capsule 7300 is positioned directly upstream of the native mitral valve 9030. The guide catheter 7220 (i.e., the exemplary second catheter) may be bent within the second steering plane 7222 by the second steering mechanism 7142, as well as axially extended from and/or retracted into the outer sheath 7210 (if needed), until the capsule 7300 is co-linearly aligned with the native mitral valve 9030 (as illustrated in FIG. 10A). The capsule may then be delivered distally into the mitral valve. In some embodiments, the first and second catheters may be configured for rotation, so as to rotationally align the first and second catheters (and thus, the delivery capsule) with the mitral valve orifice. For example, in some embodiments, outer sheath rotation knob 7182 illustrated in FIG. 7A may be configured to rotate the outer sheath 7210 and guide catheter 7220 about their respective longitudinal axes.

In some embodiments of the prosthetic valve delivery system, the first catheter and the second catheter may be configured to bend the third catheter by an angle greater than 180°, relative to a straight configuration of the third catheter. For example, the first and second catheters can each be bent by more than 90° in the same plane, resulting in bending of the third catheter by more than 180° due to the fact that the third catheter may be bent by bending of the first catheter and of the second catheter. An example of this is illustrated in FIG. 7D, where implant catheter 8100 (i.e., the exemplary third catheter) may be bent at an angle equal to or greater than 180° due to the at least 90° bend in bending portion 7215 of outer sheath 7210 (i.e. the exemplary first catheter) and the at least 90° bend in bending portion 7225 of guide catheter 7220. The third catheter may also bend in two or more different directions, relative to the straight configuration of the third catheter. FIG. 7C illustrates an example where outer sheath 7210 bends at bending portion 7215 to the right, and guide catheter 7220 bends at bending portion 7225 in a downward direction. As a result, the distal end of implant catheter 8100 may be bent in multiple directions (that is, both to the right and downwards) relative to the proximal end (not shown) of implant catheter 8100. In another example, the outer sheath 7210 and the guide catheter 7220 may be configured to bend the implant catheter 8100 by an angle greater than 180°.

In some embodiments of the prosthetic valve delivery system, an exemplary capsule may include multiple portions, including a distal capsule portion and a proximal capsule portion. The distal capsule portion may be positioned distal to the proximal capsule portion. The distal and proximal capsule portions may each be hollow structures and may include at least one opening therein. In some embodiments, the distal and proximal capsule sections may be drawn together to form the receptacle in which the prosthetic valve may be held. For example, the openings of the distal and proximal capsule portions may be drawn together, thus forming an enclosed and optionally airtight capsule. The distal capsule portion and the proximal capsule portion may be configured for movement in opposing directions, such as opposing longitudinal directions. For example, the opposing directions may be distally and proximally. In such an example, one of the distal and proximal capsule portions can be configured to move proximally while the other capsule portion can be configured to move distally. In some embodiments, the capsule portions may be configured such that their relative movement may selectively release a prosthetic valve enclosed therein. FIGS. 8A-8B show an exemplary capsule 7300, with a distal capsule portion 7340 and a proximal capsule portion 7320. FIG. 8A shows the capsule portions 7320, 7340 drawn together such that the capsule may be configured in a closed position. In the closed position, the capsule may be devoid of openings and may optionally be airtight. FIG. 8B illustrates an example of the capsule 7300 with distal capsule portion 7340 and proximal capsule portion 7320 positioned apart such that the capsule may be configured in an open position, in which distal capsule portion 7340 and nose cone 7360 of capsule 7300 may be positioned apart from proximal capsule portion 7320 and the implant catheter 8100 (i.e., the exemplary third catheter). In the open position, an interior volume of the capsule 7300 (delimited by capsule portions 7320, 7340) may be open to the surrounding environment.

In some embodiments, the distal capsule portion may be configured to retain a ventricular portion of the prosthetic valve therein, and the proximal capsule portion may be configured to retain an atrial portion of the prosthetic valve therein. The "ventricular portion" of the prosthetic valve may refer to a portion of the prosthetic valve that includes the end of the prosthetic valve configured to be situated at a location within the ventricle that is furthest from the atrium when the prosthetic valve is implanted. Similarly, the "atrial portion" of the prosthetic valve may refer to a portion of the prosthetic valve that includes the end of the prosthetic valve configured to be situated at a location within the atrium that is furthest from the ventricle when the prosthetic valve is implanted. In some embodiments, the distal capsule portion may be configured such that longitudinal movement thereof may release the ventricular portion of the prosthetic valve from retention therein. Additionally, or alternatively, the proximal capsule portion may be configured such that longitudinal movement thereof may release the atrial portion of the prosthetic valve from retention therein. In reference to exemplary prosthetic valve 6000, depicted, for example, in FIG. 6A, terminal arm ends 2444 may constitute the atrial portion of the prosthetic valve and may thus be retained within the proximal capsule portion. In some embodiments, ventricular end 2025 of annular valve body 2020 may constitute the ventricular portion of the prosthetic valve and may thus be retained within the distal capsule portion. Alternatively, in some embodiments prosthetic valve frame 2000 may include ventricular end delivery posts 2028 at the ventricular end thereof. In such embodiments, delivery posts 2028 may constitute the ventricular portion of the prosthetic valve and may thus be retained within the distal capsule portion.

In some embodiments, an axial length of the ventricular capsule portion may be at least twice as long as an axial length of the atrial capsule portion. In some embodiments, the axial length of the ventricular capsule portion may include the axial length of a flexible protective feature secured to the distal end of the ventricular capsule portion (such as nose cone 7360 illustrated in FIG. 7B). In some alternative embodiments, the axial length of the ventricular capsule portion may refer to the axial length of the portions of the ventricular capsule portion which form the receptacle configured to retain the prosthetic valve; in such embodiments, the axial length of a flexible, protective feature such as nose cone 7360 does not contribute to the axial length of the ventricular capsule portion. In some embodiments, the ventricular capsule portion may have an axial length of between 35 mm and 60 mm. In some embodiments, the ventricular capsule portion may have an axial length of between 38 mm and 42 mm. For example, and without limitation, the ventricular capsule portion may have an axial length of 38 mm, 39 mm, 40 mm, 41 mm, 42 mm, or any other suitable axial length. In such embodiments, the axial length of the ventricular capsule portion may not include the axial length of a flexible, distal feature (such as a nose cone 7360). In some alternative embodiments, the ventricular capsule portion may have an axial length of between 50 and 55 mm. For example, and without limitation, the ventricular capsule portion may have an axial length of 50 mm, 51 mm, 52 mm, 52.5 mm, 53 mm, 53.1 mm, 53.2 mm, 53.3 mm, 53.4 mm, 53.5 mm, 53.6 mm, 53.7 mm, 53.8 mm, 53.9 mm, 54 mm, 54.5 mm, 55 mm, or any other suitable axial length. In such embodiments, the axial length of the ventricular capsule portion may include the entire axial length of the ventricular capsule portion, including any flexible distal features secured to the ventricular capsule portion (such as a nose cone 7360). In some embodiments, the atrial capsule portion may have an axial length between 12 mm and 20 mm. For example, and without limitation, the atrial capsule portion may have an axial length of 12 mm, 13 mm, 14 mm, 14.5 mm, 15 mm, 15.5 mm, 16 mm, 16.1 mm, 16.2 mm, 16.3 mm, 16.4 mm, 16.5 mm, 16.6 mm, 16.7 mm, 16.8 mm, 16.9 mm, 17 mm, 17.5 mm, 18 mm, 19 mm, 20 mm, or any other suitable axial length.

In some embodiments, the exemplary distal capsule portion may be configured to retain an annular valve body of the prosthetic valve therein. The annular valve body may be a ring-shaped structure of the prosthetic valve having at least one opening therein. The at least one opening may extend longitudinally along the entire length of the annular valve body. For example, annular valve body 2020 illustrated in FIG. 2B may include an axial lumen 2022 extending longitudinally therethrough. In some embodiments, the annular valve body may be sized and configured to be seated within the orifice of a native valve when the prosthetic valve is implanted therein, and may include a flow control device, such as one or more leaflets, within the opening thereof. In some embodiments, the entire annular valve body may be retained within the distal capsule portion. Alternatively, a portion of the annular valve body may be retained within the distal capsule portion. In the example depicted in FIG. 8C, prosthetic valve 6000 may include annular valve body 2020, the entire length of which may be retained within the distal capsule portion 7340.

In some embodiments, the distal capsule portion may additionally or alternatively be configured to retain a plurality of ventricular anchoring legs of the prosthetic valve therein. In some embodiments, the ventricular anchoring legs may be configured to engage ventricular tissue of a native atrioventricular valve (e.g., a mitral valve) to anchor the prosthetic valve therein. For example, FIG. 10E depicts ventricular anchoring legs 2240 situated within ventricle 9020 and engaging the ventricular side of native mitral valve 9030, so as to anchor prosthetic valve 6000 therein. In some embodiments, the ventricular anchoring legs may be configured to minimize or prevent migration of the prosthetic valve in an atrial direction, due to the engagement of the legs with mitral valve tissue. Additionally, or alternatively, the ventricular anchoring legs may be configured to grasp tissue of the native valve to further anchor the prosthetic valve in place. In some embodiments, the ventricular anchoring legs may extend from or otherwise be connected to the annular valve body of the prosthetic valve. The prosthetic valve may include any suitable number of ventricular anchoring legs. For example, exemplary prosthetic valve 6000 may include twelve ventricular anchoring legs 2240. In some embodiments, some or all of the ventricular anchoring legs may be entirely retained within the distal capsule portion. Alternatively, one or more ventricular anchoring legs may be so configured such that a portion thereof may be retained within the distal capsule portion. In the example depicted in FIG. 8C, prosthetic valve 6000 may include a plurality of ventricular anchoring legs 2240, each of which may be entirely retained within the distal capsule portion 7340.

In some embodiments, the proximal capsule portion may be configured to retain a plurality of atrial anchoring arms of the prosthetic valve therein. Exemplary atrial anchoring arms may be configured to engage atrial tissue of a native atrioventricular valve (e.g., a mitral valve) to anchor the prosthetic valve therein. For example, FIGS. 10F-10H depict atrial anchoring arms 2440 situated within atrium 9010 and engaging the atrial side of native mitral valve 9030, so as to anchor prosthetic valve 6000 therein. In some embodiments, the atrial anchoring arms may be configured to minimize or prevent migration of the prosthetic valve in a ventricular direction, due to the engagement of the arms with mitral valve tissue. Additionally, or alternatively, the atrial anchoring arms may be configured to grasp tissue of the native valve to further anchor the prosthetic valve in place. In some embodiments, the atrial anchoring arms may extend from or otherwise be connected to the annular valve body of the prosthetic valve. The prosthetic valve may include any suitable number of atrial anchoring arms. For example, exemplary prosthetic valve 6000 may include twelve atrial anchoring arms 2440. In some embodiments, some or all of the atrial anchoring arms may be entirely retained within the proximal capsule portion. Alternatively, one or more atrial anchoring arms may be so configured such that a portion thereof may be retained within the proximal capsule portion. In the example depicted in FIG. 8C, prosthetic valve 6000 may include a plurality of atrial anchoring arms 2440. As shown in FIG. 8C, a portion of each exemplary atrial anchoring arm 2440 may be retained within the proximal capsule portion 7320, including the distal arm ends 2444, while the remainder may be retained within the distal capsule portion 7340, including connection locations 3202. In some embodiments, the exemplary distal capsule portion may be configured to release the ventricular anchoring legs while the annular valve body remains retained therein. That is, the distal capsule portion may be configured to release the ventricular anchoring legs therefrom while continuing to retain the annular valve body therein. In some embodiments, the annular valve body and ventricular anchoring legs may be retained within the distal capsule portion such that the terminal ends of the ventricular anchoring legs may be situated in closer proximity to the open, proximal end of the distal capsule portion than is the annular valve body. The distal capsule portion may be configured for longitudinal movement relative to the ventricular anchoring legs and distal capsule portion. The distal capsule portion may be configured for movement in the distal direction until the terminal ends of the legs are no longer retained therein. As the legs emerge from the distal capsule portion, they may be free from radially-constraining forces and may deflect radially outward (e.g., due to their shape-memory properties). The distal capsule portion may be moved distally until the entire length of the ventricular anchoring legs are no longer contained within the distal capsule portion, allowing the ventricular anchoring legs to deflect radially outwards. However, at least a portion of the annular valve body remains retained within the distal capsule portion at this longitudinal position of the distal capsule portion. Accordingly, the annular valve body remains radially-constrained by the distal capsule portion and may be prevented from radially expanding. The distal capsule portion may be further moved in the distal direction until the annular valve body is no longer contained within the distal capsule portion. At such a point, the annular valve body may be free from radially-constraining forces and may expand radially outward (e.g., due to its shape-memory properties).

An example of such a configuration is depicted in FIGS. 10C and 10G. Annular valve body 2020 and ventricular anchoring legs 2240 may be retained within distal capsule portion 7340. As FIG. 10C shows, distal capsule portion 7340 may be moved distally (i.e. towards ventricle 9020) until the ventricular anchoring legs 2240 are not retained therein, at which point the legs may deflect radially outward. As FIG. 10C also shows, the annular valve body 2020 may remain retained within the distal capsule portion 7340 in this position of the distal capsule portion. As FIG. 10G shows, the distal capsule portion 7340 may be further moved distally until annular valve body 2020 is no longer retained therein. At this position, the annular valve body 2020 may radially expand.

In some embodiments, a capsule of the exemplary prosthetic valve delivery system may include a valve anchor configured to secure the prosthetic valve during movement of one or more of the distal capsule portion and the proximal capsule portion. The valve anchor may be located within the capsule (e.g., within the distal capsule portion) and may selectively prevent longitudinal movement of the prosthetic valve relative thereto. In some embodiments, the valve anchor may directly engage the prosthetic valve to secure the valve against longitudinal movement. In some embodiments, the valve anchor may be positioned inside of the capsule, and in other embodiments, the valve anchor may be positioned outside of the capsule. The valve anchor may have one or more recesses that are configured to receive one or more ventricular end delivery posts of the prosthetic valve. The one or more recesses may selectively prevent longitudinal movement of the prosthetic valve. The recesses may secure the prosthetic valve to the valve anchor until the annular body of the prosthetic valve expands radially outward, thus releasing the prosthetic valve from the valve anchor. The recesses in the valve anchor may include slots, holes, hooks, openings, or any suitable receptacle configured to receive at least a portion of the prosthetic valve, such as one or more ventricular end delivery posts of the prosthetic valve. The ventricular end delivery posts may be positioned on or near the ventricular end of the prosthetic valve and may take a number of forms and shapes including D-shaped, tapered, threaded, barbed, keyed, among others, so as to secure the posts to the recesses in the valve anchor.

FIG. 8C illustrates an exemplary embodiment in which the capsule includes a valve anchor disc 8200 configured to secure the prosthetic valve against longitudinal movement during movement of one or more of the distal capsule portion 7340 and the proximal capsule portion 7320. Accordingly, valve anchor disc 8200 may be considered the valve anchor in some embodiments. In this example, ventricular end delivery posts 2028 may be D-shaped and be secured to valve anchor disc 8200 via a matching number of recesses positioned around the circumference of the valve anchor disc 8200. Ventricular end delivery posts 2028 may extend through the recesses 8205 in valve anchor disc 8200 and the D-shape may provide a tension-based interference fit to allow the valve anchor disc 8200 to secure the prosthetic valve 6000 during movement of one or more of the distal capsule portion and the proximal capsule portion. As illustrated in FIG. 8C, the diameter of valve anchor disc 8200 may be configured such that the recesses 8205 may be substantially aligned with the ventricular end delivery posts 2028 when the annular valve body 2020 is in a radially-contracted configuration. As a result, radial expansion of the annular valve body 2020 may cause movement of the delivery posts 2028 out of the recesses 8205, thus releasing the prosthetic valve from anchoring engagement with valve anchor disc 8200 and allowing longitudinal movement of the prosthetic valve.

An exemplary prosthetic valve delivery system may include a first capsule actuator configured to effect longitudinal movement of the distal capsule portion relative to the valve anchor. For example, in exemplary prosthetic valve delivery system 7000, distal capsule portion knob 7170 may be configured to effect longitudinal movement of distal capsule portion 7340 relative to the valve anchor disc 8200 (i.e., the exemplary valve anchor), and may thus be considered a first capsule actuator. The first capsule actuator may be configured to effect proximal and/or distal movement of the distal capsule portion relative to the valve anchor. In some embodiments, the first capsule actuator may be incorporated within a control handle assembly, which may be operated by a user to control different components of the prosthetic valve delivery system. Alternatively, the first capsule actuator may be incorporated within an independent control system. The first capsule actuator may include any appropriate mechanism, examples of which include, but are not limited to, a rotatable knob, a wheel, a handle, a lever, a joystick, a touchpad, and combinations thereof, among other mechanisms suitable for effecting longitudinal movement of the distal capsule portion relative to the valve anchor. In some embodiments, the first capsule actuator may be configured to effect distal movement of the distal capsule portion so as to release the ventricular anchoring legs and the annular valve body therefrom.

In some embodiments, the exemplary first capsule actuator may be configured to move the distal capsule portion to a first position in which a portion (e.g. the ventricular anchoring legs) of the prosthetic valve may be released from the capsule while the prosthetic valve remains secured relative to the capsule. Additionally, or alternatively, the first capsule actuator may be configured to move the distal capsule portion to a second position in which the prosthetic valve may be released from the capsule. In some embodiments, the first position may be a position of the distal capsule portion in which at least a portion of the ventricular anchoring legs extend out of the distal capsule portion, but in which at least a portion of the annular valve body remains radially constrained within the distal capsule portion and secured against longitudinal movement relative to at least a portion of the capsule. For example, the annular valve body may remain engaged with the valve anchor while the distal capsule portion is located at the first position thereof. In some embodiments, a portion of each ventricular anchoring leg may extend out of the distal capsule portion when the distal capsule portion is situated at the first position. Alternatively, the entirety of each ventricular anchoring leg may extend out of the distal capsule portion when the distal capsule portion is situated at the first position. The first capsule actuator may move the distal capsule portion by twisting, translation, actuation, or other mechanisms so that the distal capsule portion can be moved to the first position thereof. An exemplary first position of the distal capsule portion is illustrated in FIG. 10D. Distal capsule portion knob 7170 may move distal capsule portion 7340 towards the ventricle 9020 until the first position (i.e., the position of FIG. 10D) is reached, at which point ventricular anchoring legs 2240 may be released from the distal capsule portion 7340 and may deflect radially outwards. Annular valve body 2020, including outer frame tubular portion 3605, may remain radially-constrained within distal capsule portion 7340. As a result, anchoring posts 2028 may remain engaged with recesses 8205 of valve anchor disc 8200 (as depicted in FIG. 8C), thus securing valve 6000 against longitudinal movement relative to valve anchor disc 8200.

In some embodiments, the second position of the distal capsule portion may be a position in which the entirety of the annular valve body may be removed from the distal capsule portion. At this position, the annular valve body may be configured to radially expand, so it is no longer constrained by the distal capsule portion. As a result, in some embodiments, the annular valve body may be freed from engagement with the valve anchor and the prosthetic valve may be configured for longitudinal movement relative to the valve anchor. An exemplary second position of the distal capsule portion is illustrated in FIG. 10G. Distal capsule portion knob 7170 may extend distal capsule portion 7340 towards the ventricle 9020 until the annular valve body 2020 is removed from the distal capsule portion 7340, allowing the annular valve body to radially expand. Expansion of the annular valve body may remove anchoring posts 2028 from recesses 8205 of valve anchor disc 8200 (i.e., the exemplary valve anchor), thus permitting valve 6000 to move longitudinally relative to valve anchor disc 8200.

In some embodiments, the atrial anchoring arms may be retained within the proximal capsule portion and may be released when the proximal capsule portion is translated proximally by a second capsule actuator (discussed further below), creating a gap between the distal capsule portion and the proximal capsule portion that allows the anchoring arms to be released from the proximal capsule portion. The proximal capsule portion may be configured to translate independently of the distal capsule portion. For example, the proximal capsule portion may be moved longitudinally until the atrial anchoring arms are released, while the ventricular anchoring legs and the annular valve body may remain in a radially-contracted configuration within the distal capsule portion.

The prosthetic valve delivery system may additionally or alternatively include a second capsule actuator configured to effect longitudinal movement of the proximal capsule portion relative to the valve anchor. For example, in exemplary prosthetic valve delivery system 7000, proximal capsule portion slider 7162 may be configured to effect longitudinal movement of the proximal capsule portion 7320 relative to the valve anchor disc 8200 (i.e., the exemplary valve anchor), and may thus be considered a second capsule actuator. The second capsule actuator may be configured to effect proximal and distal movement of the proximal capsule portion relative to the valve anchor and the distal capsule portion. In some embodiments, the second capsule actuator may be incorporated within a control handle assembly, which may be operated by a user to control different components of the prosthetic valve delivery system. Alternatively, the second capsule actuator may be incorporated within an independent control system. Although the second capsule actuator is depicted as a slider 7162 in the example depicted in FIG. 7A, the second capsule actuator may alternatively include any appropriate mechanism, examples of which include, but are not limited to, a rotatable knob, a wheel, a handle, a lever, a joystick, a touchpad, and combinations thereof, among other mechanisms suitable for effecting longitudinal movement of the proximal capsule portion relative to the valve anchor. In some embodiments, the second capsule actuator may be configured to effect distal movement of the proximal capsule portion so as to release the atrial anchoring arms therefrom. FIG. 7A illustrates an exemplary prosthetic valve delivery system 7000 that includes a first capsule actuator 7170 configured to effect longitudinal movement of the distal capsule portion 7340 relative to the valve anchor disc 8200, and a second capsule actuator 7162 configured to effect longitudinal movement of the proximal capsule portion 7320 relative to the valve anchor. In some embodiments, the first capsule actuator 7170 and the second capsule actuator 7162 may be separate knobs, wheels, or any actuators suitable for a user to interface with to effect longitudinal movement in both the distal and proximal directions of the distal capsule portion 7340 and the proximal capsule portion 7320, respectively, relative to the valve anchor disc 8200. In some embodiments, the first capsule actuator 7170 and the second capsule actuator 7162 may be separately rotated or otherwise actuated by the user to effect longitudinal movement of the distal capsule portion 7340 and the proximal capsule portion 7320, respectively. The first capsule actuator 7170 and the second capsule actuator 7162 may operate simultaneously, and the first capsule actuator 7170 and the second capsule actuator 7162 may be may be configured to operate independently, where one actuator may be in operation and the other is stationary.

An exemplary prosthetic valve delivery system may include a handle configured to enable rotation of the first catheter and the second catheter. The handle may include any manual control mechanism, including a knob, lever, rotatable cuff, slider, or any other suitable structure capable of causing rotation of the first catheter and the second catheter. The handle may be incorporated within an exemplary control handle assembly, which may be operated by a user to control different components of the prosthetic valve delivery system. In some embodiments, the handle may be mechanically connected to the first catheter and the second catheter via one or more suitable mechanical connections, such as welding, adhesive, interference fit, over molding, threading, or barbs, such that actuation (e.g. rotation) of the handle may translate to rotational movement of the first catheter and second catheter. In some embodiments, the connection between the handle and the first catheter and the second catheter may be replaceable or disposable, so that after each use of the prosthetic valve delivery system, the first and second catheters can be replaced. In some embodiments, the handle may be incorporated within an independent control system. FIG. 7A illustrates an exemplary prosthetic valve delivery system 7000, which may include a handle 7100 configured to effect rotation (by outer sheath rotation knob 7182) of the outer sheath 7210 (i.e. the exemplary first catheter) and the guide catheter 7220 (i.e., the exemplary second catheter). In some embodiments, outer sheath rotation knob 7182 of handle 7100 may also be configured to effect rotation of the implant catheter 8100 (i.e., the exemplary third catheter). Alternatively, delivery system 7000 may include a implant catheter rotation knob 7186 (e.g., within cradle 7180) which may be configured to rotate implant catheter 8100 independently of the rotation of the first and second catheters.

An exemplary prosthetic valve delivery system may include a first catheter actuator configured to effect bending of the first catheter within the first steering plane. In some embodiments, the first catheter actuator may be configured to effect longitudinal movement of the first catheter. Additionally, or alternatively, the prosthetic valve delivery system may include a second catheter actuator configured to effect longitudinal movement of the second catheter and bending of the second catheter within the second steering plane. The term "actuator" can include any manual control mechanism, including a knob, lever, rotatable cuff, slider, or any other structure capable of causing longitudinal movement and bending. The first catheter actuator and second catheter actuator may be any manual control mechanism, and the first catheter actuator and second catheter actuator may be different manual control mechanisms. The first catheter actuator and the second catheter actuator may be connected to or associated with one or more pull wires connected to the first catheter and the second catheter. Accordingly, the first catheter actuator and the second catheter actuator may be connected to or integral with the first steering mechanism and the second steering mechanism that may control the one or more pull wires. In some embodiments, the first catheter and the second catheter can each have at least one pull wire connected thereto at a position along the length of the first catheter and the second catheter. For example, a pull wire may be connected directly to or near the distal end of the first catheter and a pull wire may be connected directly to or near the distal end of the second catheter. Additionally, or alternatively, the first catheter and the second catheter may have additional pull wires connected at various proximal locations in each catheter. The first catheter actuator and the second catheter actuator may provide control of the first steering mechanism and the second steering mechanism, which may pull on the one or more pull wires to effect bending of the first catheter and the second catheter. In some embodiments, the first catheter actuator and the second catheter actuator may additionally, or alternatively, include other mechanisms suitable for effecting catheter bending. In some embodiments, the first catheter actuator and second catheter actuator may be incorporated within an exemplary control handle assembly (e.g., prosthetic valve delivery system 7000), which may be operated by a user to control different components of the prosthetic valve delivery system. Alternatively, the first catheter actuator and second catheter actuator may each be incorporated within an independent control handle assembly.

FIG. 7A illustrates an exemplary prosthetic valve delivery system 7000, which may include a first catheter actuator 7120 configured to effect bending of the first catheter (via outer sheath steering knob 7122) within the first steering plane 7212; and a second catheter actuator 7140 configured to effect longitudinal movement of the second catheter (via engagement with axial movement knob 7188) and bending of the second catheter (via guide catheter steering knob 7142) within the second steering plane 7222. The first catheter actuator 7120 may be a handle extending from control handle assembly 7100 that may be mechanically connected to the outer sheath 7210 (i.e. the exemplary first catheter) to effect bending of the first catheter within the first steering plane. In some embodiments, first catheter actuator 7120 may be secured to stand 7400 of control handle assembly 7100 (for example, via a locking arrangement with cradle 7180 which may be released by button 7184). Alternatively, the first catheter actuator 7120 may be configured to translate proximally and distally with respect to the remainder of the control handle assembly 7100, and the proximal or distal translation of the first catheter actuator 7120 may control the longitudinal movement of the outer sheath 7210.

Outer sheath steering knob 7122 may be connected to or integral with the first catheter actuator 7120. Outer sheath steering knob 7122 is shown as a rotatable knob, but may alternatively be a wheel, a handle, a joystick, a touchpad, and combinations thereof, among other steering mechanisms capable of effecting bending of the first catheter within the first steering plane. For example, outer sheath steering knob 7122 may be connected to a pull wire connected to the first catheter to effect bending thereof.

In some embodiments, the second catheter actuator 7140 may be a handle extending from control handle assembly 7100 that may be mechanically connected to the second catheter to effect longitudinal movement of the second catheter and bending of the second catheter within the second steering plane. The second catheter actuator 7140 may be configured to translate proximally and distally with respect to the remainder of the control handle assembly 7100, and the proximal or distal translation of the second catheter actuator 7140 may control the longitudinal movement of the guide catheter 7220 (i.e., the exemplary second catheter). Guide catheter steering knob 7142 may be connected to or integral with the second catheter actuator 7140. Guide catheter steering knob 7142 is shown as a rotatable knob, but may alternatively be a wheel, a handle, a joystick, a touchpad, and combinations thereof, among other steering mechanisms capable of effecting bending of the second catheter within the second steering plane. For example, guide catheter steering knob 7142 may be connected to a pull wire connected to the second catheter to effect bending thereof. Guide catheter steering knob 7142 and second catheter actuator 7140 may be operated simultaneously or independently, that is, the second catheter can move longitudinally and bend at the same time or the second catheter can operate independently to move longitudinally or to bend.

In some embodiments, the first catheter actuator and second catheter actuator may be configured for relative longitudinal movement. In some embodiments, the first and second catheter actuators may both be configured for independent longitudinal movement. In alternative embodiments, one actuator may be secured against longitudinal movement (e.g., due to locking of the one actuator to an exemplary control handle assembly), while the other actuator may be configured to move longitudinally. Relative longitudinal movement between the first and second catheter actuators may effect relative longitudinal movement between the first and second catheters. In some embodiments, the first catheter actuator and the second catheter actuator may be connected to, or otherwise incorporated within, a control handle assembly and may be situated at different longitudinal positions within the control handle assembly. In some embodiments, the control handle assembly may be configured to guide the longitudinal movement of the first catheter actuator and/or the second catheter actuator. For example, one or both of the first catheter actuator and the second catheter actuator may be configured to move longitudinally on a slider, a rod, a rail, a track, or any suitable guide structure on the control handle assembly. Accordingly, the first catheter actuator and the second catheter actuator may be configured for relative longitudinal movement either towards or away from each other. FIG. 7A shows an example of the first catheter actuator 7120 and second catheter actuator 7140, which may be configured for relative longitudinal movement. In some embodiments, the first catheter actuator 7120 may be secured to the control handle assembly stand 7400, such that relative longitudinal movement between the first and second catheter actuators may be achieved by longitudinal movement of the second catheter actuator 7140 along the control handle assembly stand 7400 (for example, by rotation of axial movement knob 7188). In some alternative embodiments, the first catheter actuator 7120 may be configured to translate proximally and distally on the control handle assembly stand 7400, and the proximal or distal translation of the first catheter actuator 7120 may control the longitudinal movement of the outer sheath 7210 (i.e. the exemplary first catheter). The second catheter actuator 7140 may be configured to translate proximally and distally on the control handle assembly stand 7400, and the proximal or distal translation of the second catheter actuator 7140 may control the longitudinal movement of the guide catheter 7220 (i.e., the exemplary second catheter).

In some embodiments, the prosthetic valve delivery system may include a catheter lock configured to prevent relative longitudinal movement of the first catheter and the second catheter. In some embodiments, the catheter lock may secure the first catheter and the second catheter against any longitudinal movement, such as by locking one or both of the first and second catheters to an exemplary control handle assembly. In some alternative embodiments, the catheter lock may secure one or both of exemplary first and second catheter actuators (to which the first and second catheters, respectively, may be secured) to the exemplary control handle assembly. In further alternative embodiments, the catheter lock may secure the first and second catheters together such that they move longitudinally in tandem. The catheter lock may include any suitable locking mechanism, including a clip or friction fit, a threaded lock, a toothed gear lock, a snap fit lock, a spring-actuated lock, or any other structure capable of preventing relative longitudinal movement between the first catheter and the second catheter and, in some embodiments, securing one or both of the first and second catheters against any longitudinal movement. In some embodiments, the catheter lock may mechanically connect to the first catheter and the second catheter, or to elements secured thereto, and can secure the two catheters together so that relative movement cannot occur between the two catheters when the catheter lock is engaged.

For example, control handle assembly 7100 depicted in FIG. 7A may include a first catheter actuator 7120 and second catheter actuator 7140, which may be secured to outer sheath 7210 (i.e., the exemplary first catheter) and guide catheter 7220 (i.e., the exemplary second catheter), respectively. Actuators 7120 and 7140 may be mounted upon a cradle 7180, to which the first catheter actuator 7120 may be secured. Cradle 7180 may include a toothed gear configured to be rotated by rotation knob 7188. Second catheter actuator 7140 may include a toothed rack configured to engage the toothed gear. In some embodiments, rotation of the toothed gear due to rotation of knob 7188 may cause second catheter actuator 7140 to translate longitudinally relative to the cradle 7180 and to the first catheter actuator 7120 due to engagement of the toothed rack with the rotating toothed gear. This rack and gear arrangement may constitute the catheter lock because it may be configured to prevent relative longitudinal movement between the first and second catheter actuators unless knob 7188 is rotated; this, in turn, may prevent relative longitudinal movement between the first and second catheters.

In some embodiments, the first catheter and second catheter may be configured to advance the capsule through vasculature and across a fossa to position the prosthetic valve within a heart chamber. The first catheter and second catheter may be configured to approach the heart transfemorally, transapically, transatrially, or transseptally. Specifically, as in an example discussed above, the first catheter can cross the fossa ovalis and enter the left atrium of the patient's heart. In this example, the first steering plane may align with the fossa ovalis to ensure passage of the first catheter through the fossa ovalis. Once positioned in the left atrium, the second catheter can translate from the distal end of the first catheter. The second catheter steering mechanism can align the second catheter steering plane with the native mitral valve plane such that the second catheter can position the capsule at a position co-linear with the native mitral plane. The "native mitral plane" refers to the plane corresponding to the passageway through the native mitral valve of the patient. FIGS. 10A-10H show an exemplary deployment sequence of the prosthetic valve and the cardiac delivery system where the outer sheath 7210 (i.e. the exemplary first catheter) and guide catheter 7220 (i.e., the exemplary second catheter) may be configured to advance the capsule 7300 through vasculature and across a fossa to position the prosthetic valve within a heart chamber (e.g. an atrium 9010).

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A prosthetic valve delivery system, comprising:
   a first catheter;
   a first steering mechanism connected to a first pull wire that is configured to bend the first catheter within a first steering plane;
   a second catheter coaxially arranged within the first catheter;
   a second steering mechanism connected to a second pull wire that is configured to bend the second catheter within a second steering plane, different from the first steering plane;
   a third catheter coaxially arranged within the second catheter;
   a third steering mechanism connected to a third pull wire that is configured to bend the third catheter within a third steering plane, different from the first and second steering planes; and
   a capsule positioned distal to both the first catheter and the second catheter and connected to the third catheter, the capsule configured for longitudinal movement relative to the first catheter and second catheter and configured to retain a prosthetic valve therein during transvascular advancement, the capsule comprising:
      a distal capsule portion and a proximal capsule portion, the distal capsule portion and the proximal capsule portion being configured for movement in opposing directions,
      wherein the distal capsule portion is configured to retain an annular valve body of the prosthetic valve and a plurality of ventricular anchoring legs of the prosthetic valve within the distal capsule portion,
      wherein the proximal capsule portion is configured to retain a plurality of atrial anchoring arms of the prosthetic valve within the proximal capsule portion, and
      wherein the distal capsule portion is configured to release the ventricular anchoring legs while the ventricular anchoring legs are situated within a heart atrium, while the annular valve body remains retained within the distal capsule portion, and while the plurality of atrial anchoring arms remain retained in the proximal capsule portion.

2. The delivery system of claim 1, wherein the first steering plane is orthogonal to the second steering plane.

3. The delivery system of claim 1, wherein the first catheter is configured to remain substantially straightened while the second catheter bends within the second steering plane.

4. The delivery system of claim 1, wherein the first catheter and the second catheter are each configured to bend by an angle greater than 90°.

5. The delivery system of claim 4, wherein the first catheter and the second catheter are each configured to bend by an angle no greater than 120°.

6. The delivery system of claim 1, wherein at least a portion of the capsule is configured for longitudinal movement relative to the third catheter.

7. The delivery system of claim 1, wherein the first catheter, the second catheter, and the third catheter are all configured for relative longitudinal movement.

8. The delivery system of claim 1, wherein the first catheter and the second catheter are configured to bend the third catheter by an angle greater than 180°.

9. The delivery system of claim 1,
   wherein the distal capsule portion is configured to retain a ventricular portion of the prosthetic valve therein, and
   wherein the proximal capsule portion is configured to retain an atrial portion of the prosthetic valve therein.

10. The delivery system of claim 1, wherein the capsule further includes a valve anchor configured to secure the prosthetic valve during movement of one or more of the distal capsule portion and the proximal capsule portion.

11. The delivery system of claim 10, further comprising:
    a first capsule actuator configured to effect longitudinal movement of the distal capsule portion relative to the valve anchor; and
    a second capsule actuator configured to effect longitudinal movement of the proximal capsule portion relative to the valve anchor.

12. The delivery system of claim 11, wherein the first capsule actuator is configured to:
    move the distal capsule portion to a first position in which a portion of the prosthetic valve is released from the capsule while the prosthetic valve remains secured relative to the capsule; and
    move the distal capsule portion to a second position in which the prosthetic valve is released from the capsule.

13. The delivery system of claim 1, further comprising:
    a control handle assembly including the first steering mechanism, the second steering mechanism, the third steering mechanism, and at least one control handle connected to the first catheter, second catheter, and third catheter,
    wherein the control handle assembly is configured to:
       enable rotation of the first catheter and the second catheter together, and
       independently bend the first catheter, the second catheter, and the third catheter within the first, second, and third steering planes, respectively, while at least one of the first catheter, the second catheter, or the third catheter is secured against longitudinal movement.

14. The delivery system of claim 1, further comprising:
a first catheter actuator configured to effect longitudinal movement of the first catheter; and
a second catheter actuator configured to effect longitudinal movement of the second catheter.

15. The delivery system of claim 14, wherein the first catheter actuator and second catheter actuator are configured for relative longitudinal movement.

16. The delivery system of claim 1, further comprising:
a catheter lock configured to prevent relative longitudinal movement of the first catheter and the second catheter.

17. The delivery system of claim 1, wherein the first catheter and second catheter are configured to advance the capsule through vasculature and across a fossa to position the prosthetic valve within a heart chamber.

18. The delivery system of claim 1, wherein the third catheter is connected to the proximal capsule portion and is configured to control longitudinal movement of the proximal capsule portion relative to the prosthetic valve.

19. The delivery system of claim 1, further comprising:
a control shaft extending from the third catheter and connected to the distal capsule portion, wherein the control shaft is configured to control longitudinal movement of the distal capsule portion relative to the prosthetic valve and the third catheter.

20. The delivery system of claim 1, further comprising:
a rotation mechanism configured to effect rotation of the first catheter and second catheter, so as to control an advancement direction of the capsule.

21. The delivery system of claim 20, wherein the third catheter is secured against rotation effected by the rotation mechanism.

* * * * *